United States Patent
Presnell et al.

(10) Patent No.: US 6,548,056 B2
(45) Date of Patent: Apr. 15, 2003

(54) MURINE INTERFERON-α

(75) Inventors: Scott R. Presnell, Tacoma, WA (US); Andrew L. Feldhaus, Lynnwood, WA (US); Zeren Gao, Redmond, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/951,843

(22) Filed: Sep. 12, 2001

(65) Prior Publication Data

US 2002/0168378 A1 Nov. 14, 2002

Related U.S. Application Data

(62) Division of application No. 09/528,760, filed on Mar. 17, 2000, now Pat. No. 6,312,924.

(60) Provisional application No. 60/125,045, filed on Mar. 18, 1999, and provisional application No. 60/155,739, filed on Sep. 23, 1999.

(51) Int. Cl.⁷ .................. A61K 38/21; C07K 17/00; C12P 21/04

(52) U.S. Cl. ............... 424/85.7; 424/85.4; 530/350; 530/351; 435/69.51

(58) Field of Search .................. 520/331, 350; 424/85.7, 85.4; 435/69.51

(56) References Cited

PUBLICATIONS

Soares, M.B., EST No. EST2244319 (GenBank Acc. No. AA998549).
Marra, M., EST No. EST1914655 (GenBank Acc. No. AI155872).
Lee, N.H., EST No. EST1941594 (GenBank Acc. No. AI179042).

*Primary Examiner*—Yvonne Eyler
*Assistant Examiner*—Janet L. Andres
(74) *Attorney, Agent, or Firm*—Brian J. Walsh; Philip B. C. Jones

(57) ABSTRACT

Interferons represent an important class of biopharmaceutical products, which have a proven track record in the treatment of a variety of medical conditions, including the treatment of certain autoimmune diseases, the treatment of particular cancers, and the enhancement of the immune response against infectious agents. The present invention provides a new form of murine interferon-α, which has applications in diagnosis and therapy.

7 Claims, No Drawings

MURINE INTERFERON-α

CROSS-REFERENCE TO RELATED APPLICATIONS

This is a divisional application of application Ser. No. 09/528,760, filed on Mar. 17, 2000 now U.S. Pat. No. 6,312,924.

This application claims the benefit of U.S. Provisional application Nos. 60/125,045 (filed Mar. 18, 1999), and 60/155,739 (filed Sep. 23, 1999), the contents of which are incorporated by reference.

TECHNICAL FIELD

The present invention relates generally to a new cytokine having diagnostic and therapeutic uses. In particular, the present invention relates to a novel murine interferon-α, and to nucleic acid molecules encoding interferon-α.

BACKGROUND OF THE INVENTION

Cellular differentiation of multicellular organisms is controlled by hormones and polypeptide growth factors. These diffusable molecules allow cells to communicate with each other and act in concert to form tissues and organs, and to repair and regenerate damaged tissue. Examples of hormones and growth factors include the steroid hormones, parathyroid hormone, follicle stimulating hormone, the interferons, the interleukins, platelet derived growth factor, epidermal growth factor, and granulocyte-macrophage colony stimulating factor, among others.

Hormones and growth factors influence cellular metabolism by binding to receptor proteins. Certain receptors are integral membrane proteins that bind with the hormone or growth factor outside the cell, and that are linked to signaling pathways within the cell, such as second messenger systems. Other classes of receptors are soluble intracellular molecules.

Of particular interest, from a therapeutic standpoint, are the interferons (reviews on interferons are provided by De Maeyer and De Maeyer-Guignard, "Interferons," in *The Cytokine Handbook 3rd Edition,* Thompson (ed.), pages 491–516 (Academic Press Ltd. 1998), and by Walsh, *Biopharmaceuticals: Biochemistry and Biotechnology,* pages 158–188 (John Wiley & Sons 1998)). Interferons exhibit a variety of biological activities, and are useful for the treatment of certain autoimmune diseases, particular cancers, and the enhancement of the immune response against infectious agents, including viruses, bacteria, fungi, and protozoa. To date, six forms of interferon have been identified, which have been classified into two major groups. The so-called "type I" interferons include interferon-α, interferon-β, interferon-ω, interferon-δ, and interferon-τ. Currently, interferon-γ and one subclass of interferon-α are the only type II interferons.

Type I interferons, which are thought to be derived from the same ancestral gene, have retained sufficient similar structure to act by the same cell surface receptor. The α-chain of the human interferon-α/β receptor comprises an extracellular N-terminal domain, which has the characteristics of a class II cytokine receptor. Interferon-γ does not share significant homology with the type I interferons or with the type II interferon-α subtype, but shares a number of biological activities with the type I interferons.

In humans, at least 16 non-allelic genes code for different subtypes of interferon-α, while interferons β and ω are encoded by single genes. Type I interferon genes are clustered in the short arm of chromosome 9. Unlike typical structural human genes, interferon-α, interferon-β, and interferon-ω lack introns. A single gene for human interferon-γ is localized on chromosome 12 and contains three introns. To date, interferon-τ has been described only in cattle and sheep, while interferon-δ has been described only in pigs.

At least 12 non-allelic murine interferon-α genes have been identified so far (for a review, see De Maeyer and De Maeyer-Guignard, "Interferons," in *The Cytokine Handbook 3rd Edition,* Thompson (ed.), pages 491–516 (Academic Press Ltd. 1998)). In general, the structure of murine interferon-α genes is similar to that of corresponding human genes. The mouse also appears to have a single interferon-β gene. Murine interferon-α and -β genes are clustered on chromosome 4, although the interferon-β gene is distal from the interferon-α cluster.

Clinicians are taking advantage of the multiple activities of interferons by using the proteins to treat a wide range of conditions. For example, one form of interferon-α has been approved for use in more than 50 countries for the treatment of medical conditions such as hairy cell leukemia, renal cell carcinoma, basal cell carcinoma, malignant melanoma, AIDS-related Kaposi's sarcoma, multiple myeloma, chronic myelogenous leukemia, non-Hodgkin's lymphoma, laryngeal papillomatosis, mycosis fungoides, condyloma acuminata, chronic hepatitis B, hepatitis C, chronic hepatitis D, and chronic non-A, non-B/C hepatitis. The U.S. Food and Drug Administration has approved the use of interferon-β to treat multiple sclerosis, a chronic disease of the nervous system. Interferon-γ is used to treat chronic granulomatous diseases, in which the interferon enhances the patient's immune response to destroy infectious bacterial, fungal, and protozoal pathogens. Clinical studies also indicate that interferon-γ may be useful in the treatment of AIDS, leishmaniasis, and lepromatous leprosy.

Although new uses of known interferons may be discovered, a need exists for the provision of new interferons for biopharmaceuticals.

BRIEF SUMMARY OF THE INVENTION

The present invention provides a novel murine interferon-α, designated "Zcyto13." The present invention also provides Zcyto13 polypeptides and Zcyto13 fusion proteins, as well as nucleic acid molecules encoding such polypeptides and proteins, and methods for using these nucleic acid molecules and amino acid sequences.

DETAILED DESCRIPTION OF THE INVENTION

1. Overview

A nucleic acid molecule containing a sequence that encodes murine interferon-α, initially designated as "Zcyto13," has the following nucleotide sequence:

ATACTAAGCA CCAGGGTTGA GAATGACTCC
AAAGTTTTTA TGGCTGGTGG CCCTTGTGGC
TCTATACATT CCGCCCATCC AATCTCTGAA
CTGTGTTTAC CTGGATGATA GCATCTTGGA
AAATGTGAAA CTTCTGGGCA GTACCATGAC
CGGCTITCCC TTAAGATGTC TAAAAGATAT
CACAGATTTT AAGTTTCCTA AAGAGATTTT
GCCATACATC CAGCATATGA AAAGGGAGAT
AAACGCCGTC TCCTATCGTA TATCCTCTCT
GGCACTAACT ATCTTCAATC TTAAAGGCTC
CATCCCTCCA GTGACAGAGG AACACTGGGA
ACGTATCAGA TCGGGACTTT TCAAACAAGT

GCGGCAAGCT CAAGAGTGCT TCATGGACGA
GGAGAAAGAG AACAGGGAAC ATCCTCACTC
CGAGGACTTC CTGACAGTCT ACCTGGAGTT
GGGCAAGTAT TTCTTCAGAA TCAAAAAGTT
CCTGATAAAT AAGAAATACA GTTTCTGTGC
ATGGAAGATR GTCACAGTGG AAATAAGAAG
ATGTTTCATT ATATTTTCCA AGTCCAGAAA
ACTACTCAAA ATGATATCAG AATCACCCAC
CTTCAAGCAA GAACTTAAAT AGAAGCTGCA
ATTGCTCAAA TGTCTCCAAG AACGCTTTAT
TCTAAAGCCA TTACCAGGAT GCTGCTAATG
CTACCTTCAG ATGCAAGACT TTTCAAGTTC
AGGGTTCAAG GCAGTGCAGT CAAAGAAAGT
CTTAAGCAAA AGATGAAC (SEQ ID NO:1).

The encoded polypeptide has the following amino acid sequence: MTPKFLWLVA LVALYIPPIQ SLNCVYLDDS ILENVKLLGS TMTGFPLRCL KDITDFKFPK EILPYIQHMK REINAVSYRI SSLALTIFNL KGSIPPV- TEE HWERIRSGLF KQVRQAQECF MDEEKENREH PHSEDFLTVY LELGKYFFRI KKFLINKKYS FCAWK- IVTVE IRRCFIIFSK SRKLLKMISE SPTFKQELK (SEQ ID NO:2). The Zcyto13 form of an interferon-α gene encodes a polypeptide of 199 amino acids, as shown in SEQ ID NO:2. The signal sequence for Zcyto13 can be predicted as comprising Met$^1$ through Ser$^{21}$ of SEQ ID NO:2. The mature peptide for Zcyto13 begins at Leu$^{22}$. Additional structural features of Zcyto13 are summarized in Table 4.

Hybridization analyses indicate that the Zcyto13 gene is strongly expressed in murine heart and liver tissue, and to a lesser extent, in murine brain, kidney, uterine, spleen, and seven-day embryo tissues. Zcyto13 RNA was also detected in lung, skeletal muscle, and testis tissues, as well as in the tissues of 11-, 15-, and 17-day embryos. Typically, Zcyto13 mRNA appeared as bands of about 2.8 and 6.6 kilobases. These results show that the interferon-α sequences can be used differentiate among various tissues.

Southern analyses revealed that a Zcyto13 probe bound with rat and mouse genomic DNA. When incubated with EcoRI-digested DNA, the probe hybridized with fragments of 4.8 and 5.65 kilobases in murine genomic DNA, and 2.1 and 5.2 kilobases in rat genomic DNA.

The Zcyto13 gene has been mapped to mouse chromosome 4 (framework marker D4Mit94, located at 4.6 centimorgans). The murine interferon-α/-β gene cluster is also located at chromosome 4.

As described below, the present invention provides isolated polypeptides having an amino acid sequence that is at least 70%, at least 80%, or at least 90% identical to either amino acid residues 22 to 199 of SEQ ID NO:2 or amino acid residues 1 to 199 of SEQ ID NO:2, wherein such isolated polypeptides can either (a) specifically bind with an antibody that specifically binds with a polypeptide consisting of the amino acid sequence of SEQ ID NO:2, or (b) exhibits anti-viral activity or anti-proliferative activity. An illustrative polypeptide is a polypeptide that comprises a first amino acid sequence consisting of amino acid residues 22 to 199 of SEQ ID NO:2, or a polypeptide that further comprises a signal secretory sequence that resides in an amino-terminal position relative to the first amino acid sequence, wherein the signal secretory sequence comprises amino acid residues 1 to 21 of the amino acid sequence of SEQ ID NO:2.

Other exemplary polypeptides includes polypeptides that comprise at least one of the following amino acid motifs: (a) the amino acid sequence [FSPN][PFG][LK][RSI][CN]L [KT][DY][IR][TQKA]DF[GK][FI]P (SEQ ID NO:16), wherein the sequence is further defined by at least one condition selected from the group consisting of: the first residue is F, (ii) the fourth residue is R, (iii) the ninth residue is I, and (iv) the tenth residue is T, or (b) the amino acid sequence [DVR][FY]L[IRK][NEKL][KM]K [YH][SN] [FPLS][CY]AW[KEM][IV][IV][TR][VA]E (SEQ ID NO:17), wherein the sequence is further defined by at least one condition selection from the group consisting of: (i) the first residue is K, (ii) the fourth residue is I, (iii) the fifth residue is N, (iv) the tenth residue is F, (v) the fourteenth residue eighteenth residue is V. Moreover, illustrative polypeptides comprise both motif (a) and motif (b).

Additional exemplary polypeptides include polypeptides comprising an amino acid sequence of 15, 20, or 30 contiguous amino acid residues of the following amino acid sequences within SEQ ID NO:2: amino acid residues 22 to 199, amino acid residues 22 to 188, amino acid residues 22 to 45, amino acid residues 46 to 64, amino acid residues 65 to 89, amino acid residues 99 to 124, amino acid residues 134 to 155, amino acid residues 22 to 89, and amino acid residues 161 to 181. Other illustrative polypeptides comprise an amino acid sequence selected from the group consisting of: amino acid residues 22 to 199 of SEQ ID NO:2, amino acid residues 22 to 188 of SEQ ID NO:2, amino acid residues 22 to 45 of SEQ ID NO:2, amino acid residues 46 to 64 of SEQ ID NO:2, amino acid residues 65 to 89 of SEQ ID NO:2, amino acid residues 99 to 124 of SEQ ID NO:2, amino acid residues 134 to 155 of SEQ ID NO:2, amino acid residues 22 to 89 of SEQ ID NO:2, and amino acid residues 161 to 181 of SEQ ID NO:2. Additional examples include polypeptides consisting of an amino acid sequence selected from the group consisting of: amino acid residues 22 to 199 of SEQ ID NO:2, amino acid residues 22 to 188 of SEQ ID NO:2, amino acid residues 22 to 45 of SEQ ID NO:2, amino acid residues 46 to 64 of SEQ ID NO:2, amino acid residues 65 to 89 of SEQ ID NO:2, amino acid residues 99 to 124 of SEQ ID NO:2, amino acid residues 134 to 155 of SEQ ID NO:2, amino acid residues 22 to 89 of SEQ ID NO:2, and amino acid residues 161 to 181 of SEQ ID NO:2.

The polypeptides described herein can further comprise an affinity tag.

The present invention further provides antibodies and antibody fragments that specifically bind with such polypeptides. Exemplary antibodies include polyclonal antibodies, murine monoclonal antibodies, humanized antibodies derived from murine monoclonal antibodies, and human monoclonal antibodies. Illustrative antibody fragments include F(ab')$_2$, F(ab)$_2$, Fab', Fab, Fv, scFv, and minimal recognition units. The present invention also includes anti-idiotype antibodies that specifically bind with such antibodies or antibody fragments. Certain anti-idiotype antibodies, or anti-idiotype antibody fragments, possesses anti-viral activity or anti-proliferative activity.

The present invention her includes compositions comprising a carrier and a peptide, polypeptide, antibody, or anti-idiotype antibody described herein. For example, the composition can be a pharmaceutical composition, and the carrier can be a pharmaceutically acceptable carrier.

The present invention also provides isolated nucleic acid molecules that encode a Zcyto13 polypeptide, wherein the nucleic acid molecule is selected from the group consisting of (a) a nucleic acid molecule comprising the nucleotide sequence of SEQ ID NO:3, (b) a nucleic acid molecule encoding the amino acid sequence of SEQ ID NO:2, and (c) a nucleic acid molecule that remains hybridized following stringent wash conditions to a nucleic acid molecule consisting of the nucleotide sequence of SEQ ID NO:1, or the complement of SEQ ID NO:1.

Illustrative nucleic acid molecules include those in which any difference between the amino acid sequence encoded by the nucleic acid molecule and the corresponding amino acid sequence of SEQ ID NO:2 is due to a conservative amino acid substitution. The present invention further contemplates isolated nucleic acid molecules that comprise a nucleotide sequence of nucleotides 86 to 619 of SEQ ID NO:1.

The present invention also includes vectors and expression vectors comprising such nucleic acid molecules. Such expression vectors may comprise a transcription promoter, and a transcription terminator, wherein the promoter is operably linked with the nucleic acid molecule, and wherein the nucleic acid molecule is operably linked with the transcription terminator. The present invention further includes recombinant host cells comprising these vectors and expression vectors. Illustrative host cells include bacterial, yeast, fungal, avian, insect, mammalian, and plant cells. Recombinant host cells comprising such expression vectors can be used to prepare Zcyto13 polypeptides by culturing such recombinant host cells that comprise the expression vector and that produce the Zcyto13 protein, and, optionally, isolating the Zcyto13 protein from the cultured recombinant host cells. In addition, the present invention provides pharmaceutical compositions comprising a pharmaceutically acceptable carrier and at least one of such an expression vector or recombinant virus comprising such expression vectors.

The present invention also contemplates methods for detecting the presence of Zcyto13 RNA in a biological sample, comprising the steps of (a) contacting a Zcyto13 nucleic acid probe under hybridizing conditions with either (i) test RNA molecules isolated from the biological sample, or (ii) nucleic acid molecules synthesized from the isolated RNA molecules, wherein the probe has a nucleotide sequence comprising a portion of the nucleotide sequence of SEQ ID NO:1, or its complement, and (b) detecting the formation of hybrids of the nucleic acid probe and either the test RNA molecules or the synthesized nucleic acid molecules, wherein the presence of the hybrids indicates the presence of Zcyto13 RNA in the biological sample.

The present invention further provides methods for detecting the presence of Zcyto13 polypeptide in a biological sample, comprising the steps of: (a) contacting the biological sample with an antibody or an antibody fragment that specifically binds with a polypeptide consisting of the amino acid sequence of SEQ ID NO:2, wherein the contacting is performed under conditions that allow the binding of the antibody or antibody fragment to the biological sample, and (b) detecting any of the bound antibody or bound antibody fragment. Such an antibody or antibody fragment may further comprise a detectable label selected from the group consisting of radioisotope, fluorescent label, chemiluminescent label, enzyme label, bioluminescent label, and colloidal gold.

The present invention also provides kits for performing these detection methods. For example, a kit for detection of Zcyto13 gene expression may comprise a container that comprises a nucleic acid molecule, wherein the nucleic acid molecule is selected from the group consisting of (a) a nucleic acid molecule comprising the nucleotide sequence of nucleotides 86 to 619 of SEQ ID NO:1, (b) a nucleic acid molecule comprising the complement of nucleotides 86 to 619 of the nucleotide sequence of SEQ ID NO:1, (c) a nucleic acid molecule that is a fragment of (a) consisting of at least eight nucleotides, and (d) a nucleic acid molecule that is a fragment of (b) consisting of at least eight nucleotides. Such a kit may also comprise a second container that comprises one or more reagents capable of indicating the presence of the nucleic acid molecule. On the other hand, a kit for detection of Zcyto13 protein may comprise a container that comprises an antibody, or an antibody fragment, that specifically binds with a polypeptide consisting of the amino acid sequence of SEQ ID NO:2.

The present invention also contemplates anti-idiotype antibodies, or anti-idiotype antibody fragments, that specifically bind an antibody or antibody fragment that specifically binds a polypeptide consisting of the amino acid sequence of SEQ ID NO:2, wherein the anti-idiotype antibody, or anti-idiotype antibody fragment, possesses anti-viral activity or anti-proliferative activity.

The present invention also provides isolated nucleic acid molecules comprising a nucleotide sequence that encodes a Zcyto13 secretion signal sequence and a nucleotide sequence that encodes a biologically active polypeptide, wherein the Zcyto13 secretion signal sequence comprises an amino acid sequence of residues 1 to 21 of SEQ ID NO:2. Illustrative biologically active polypeptides include Factor VIIa, proinsulin, insulin, follicle stimulating hormone, tissue type plasminogen activator, tumor necrosis factor, interleukin, colony stimulating factor, interferon, erytiropoietin, and thrombopoietin. Moreover, the present invention provides fusion proteins comprising a Zcyto13 secretion signal sequence and a polypeptide, wherein the Zcyto13 secretion signal sequence comprises an amino acid sequence of residues 1 to 21 of SEQ ID NO:2. Additional fusion proteins comprise a Zcyto13 moiety and an immunoglobulin moiety. An illustrative immunoglobulin moiety is an immunoglobulin heavy chain constant region, such as a human $F_c$ fragment. The present invention also includes isolated nucleic acid molecules that encode such fusion proteins.

The present invention further contemplates variant Zcyto13 polypeptides, wherein the amino acid sequence of the variant is characterized by at least one amino acid substitution within SEQ ID NO:2 selected from the group consisting of: (a) an alanine for glycine$^{39}$, (b) a valine for leucine$^{63}$, (c) a threonine for serine$^{81}$, (d) a valine for isoleucine$^{105}$, and (e) a leucine for valine$^{113}$. Other variant Zcyto13 polypeptides have an amino acid sequence that shares an identity with the amino acid sequence of SEQ ID NO:2 selected from the group consisting of at least 70% identity, at least 80% identity, at least 90% identity, at least 95% identity, or greater than 95% identity, and wherein any difference between the amino acid sequence of the variant polypeptide and the amino acid sequence of SEQ ID NO:2 is due to one or more conservative amino acid substitutions. The present invention also includes isolated polypeptides consisting of an amino acid sequence of amino acid residues 22–89 of SEQ ID NO:2.

The present invention further includes methods of inhibiting a viral infection of cells, comprising the step of administering a composition comprising Zcyto13 to the cells. For example, the composition can be a pharmaceutical composition, which is administered in a therapeutically effective amount to a subject, which has a viral infection. In vivo treatment of a viral infection can provide at least one physiological effect selected from the group consisting of decreased viral titer, decreased detectable viral antigen, and increased anti-viral antibody titer.

The present invention also includes methods of inhibiting the proliferation of tumor cells, comprising the step of administering a composition comprising Zcyto13 to the tumor cells. In an in vivo approach, the composition is a pharmaceutical composition, administered in a therapeutically effective amount to a subject, which has a tumor. Such in vivo administration can provide at least one physiological effect selected from the group consisting of decreased number of tumor cells, decreased metastasis, decreased size of a solid tumor, and increased necrosis of a tumor.

The present invention also provides fusion proteins comprising a Zcyto13 polypeptide moiety. Such fusion proteins can further comprise an immunoglobulin moiety. An exemplary immunoglobulin moiety is a human immunoglobulin heavy chain constant region.

These and other aspects of the invention will become evident upon reference to the following detailed description. In addition, various references are identified below and are incorporated by reference in their entirety.

2. Definitions

In the description that follows, a number of terms are used extensively. The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence. For example, the sequence 5' ATGCACGGG 3' (SEQ ID NO:18) is complementary to 5' CCCGTGCAT 3' (SEQ ID NO:19).

The term "contig" denotes a nucleic acid molecule that has a contiguous stretch of identical or complementary sequence to another nucleic acid molecule. Contiguous sequences are said to "overlap" a given stretch of a nucleic acid molecule either in their entirety or along a partial stretch of the nucleic acid molecule. For example, representative contigs to the polynucleotide sequence 5' ATGGAGCTT 3' (SEQ ID NO:20) are 5' AGCTTgagt 3' (SEQ ID NO:21) and 3' tcgacTACC 5' (SEQ ID NO:22).

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of MnRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551 (1993)), cyclic AMP response elements (CREs), serum response elements (SREs; Treisman, *Seminars in Cancer Biol.* 1:47 (1990)), glucocorticoid response elements (GREs), and binding sites for other transcription factors, such as CRE/ATF (O'Reilly et al., *J. Biol. Chem.* 267:19938 (1992)), AP2 (Ye et al., *J. Biol. Chem.* 269:25728 (1994)), SP1, cAMP response element binding protein (CREB; Loeken, *Gene Expr.* 3:253 (1993)) and octamer factors (see, in general, Watson et al., eds., *Molecular Biology of the Gene,* 4th ed. (The Benjamin/Cummings Publishing Company, Inc. 1987), and Lemaigre and Rousseau, *Biochem. J.* 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner. For example, the Zcyto13 regulatory element preferentially induces gene expression in heart, liver, brain, kidney, and spleen tissues, as opposed to lung, skeletal muscle, and testis tissues.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

An "integrated genetic element" is a segment of DNA that has been incorporated into a chromosome of a host cell after that element is introduced into the cell through human manipulation. Within the present invention, integrated genetic elements are most commonly derived from linearized plasmids that are introduced into the cells by electroporation or other techniques. Integrated genetic elements are passed from the original host cell to its progeny.

A "cloning vector" is a nucleic acid molecule, such as a plasmid, cosmid, or bacteriophage, that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces the Zcyto13 form of interferon-α from an expression vector. In contrast, Zcyto13 can be produced by a cell that is a "natural source" of Zcyto13, and that lacks an expression vector.

"Integrative transformants" are recombinant host cells, in which heterologous DNA has become integrated into the genomic DNA of the cells.

A "fusion protein" is a hybrid protein expressed by a nucleic acid molecule comprising nucleotide sequences of at least two genes. For example, a fusion protein can comprise at least part of a Zcyto13 polypeptide fused with a polypeptide that binds an affinity matrix. Such a fusion protein provides a means to isolate large quantities of Zcyto13 using affinity chromatography.

The term "receptor" denotes a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a polypeptide encoded by a splice variant of an mRNA transcribed from a gene.

As used herein, the term "immunomodulator" includes cytokines, stem cell growth factors, lymphotoxins, co-stimulatory molecules, hematopoietic factors, and synthetic analogs of these molecules.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9$ $M^{-1}$.

An "anti-idiotype antibody" is an antibody that binds with the variable region domain of an immunoglobulin. In the present context, an anti-idiotype antibody binds with the variable region of an anti-Zcyto13 antibody, and thus, an anti-idiotype antibody mimics an epitope of Zcyto113.

An "antibody fragment" is a portion of an antibody such as $F(ab')_2$, $F(ab)_2$, Fab', Fab, and the like. Regardless of structure, an antibody fragment binds with the same antigen that is recognized by the intact antibody. For example, an anti-Zcyto13 monoclonal antibody fragment binds with an epitope of Zcyto13.

The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A "chimeric antibody" is a recombinant protein that contains the variable domains and complementary determining regions derived from a rodent antibody, while the remainder of the antibody molecule is derived from a human antibody.

"Humanized antibodies" are recombinant proteins in which murine complementarity determining regions of a monoclonal antibody have been transferred from heavy and light variable chains of the murine immunoglobulin into a human variable domain.

As used herein, a "therapeutic agent" is a molecule or atom which is conjugated to an antibody moiety to produce a conjugate which is useful for therapy. Examples of therapeutic agents include drugs, toxins, immunomodulators, chelators, boron compounds, photoactive agents or dyes, and radioisotopes.

A "detectable label" is a molecule or atom, which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a polyhistidine tract, protein A (Nilsson et al., *EMBO J.* 4:1075 (1985); Nisson et al., *Methods Enzymol.* 198:3 (1991)), glutathione S transferase (Smith and Johnson, *Gene* 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). DNAs encoding affinity tags are available from commercial suppliers (e.g., Pharmacia Biotech, Piscataway, N.J.).

A "naked antibody" is an entire antibody, as opposed to an antibody fragment, which is not conjugated with a therapeutic agent. Naked antibodies include both polyclonal and monoclonal antibodies, as well as certain recombinant antibodies, such as chimeric and humanized antibodies.

As used herein, the term "antibody component" includes both an entire antibody and an antibody fragment.

An "immunoconjugate" is a conjugate of an antibody component with a therapeutic agent or a detectable label.

As used herein, the term "antibody fusion protein" refers to a recombinant molecule that comprises an antibody component and a therapeutic agent. Examples of therapeutic agents suitable for such fusion proteins include immunomodulators ("antibody-immunomodulator fusion protein") and toxins ("antibody-toxin fusion protein").

A "tumor associated antigen" is a protein normally not expressed, or expressed at lower levels, by a normal counterpart cell. Examples of tumor associated antigens include alpha-fetoprotein, carcinoembryonic antigen, and Her-2/neu. Many other illustrations of tumor associated antigens are known to those of skill in the art. See, for example, Urban et al., *Ann. Rev. Immunol.* 10:617 (1992).

As used herein, an "infectious agent" denotes both microbes and parasites. A "microbe" includes viruses, bacteria, rickettsia, mycoplasma, protozoa, fungi and like microorganisms. A "parasite" denotes infectious, generally microscopic or very small multicellular invertebrates, or ova or juvenile forms thereof, which are susceptible to immune-mediated clearance or lytic or phagocytic destruction, such as malarial parasites, spirochetes, and the like.

An "infectious agent antigen" is an antigen associated with an infectious agent.

A "target polypeptide" or a "target peptide" is an amino acid sequence that comprises at least one epitope, and that is expressed on a target cell, such as a tumor cell, or a cell that carries an infectious agent antigen. T cells recognize peptide epitopes presented by a major histocompatibility complex molecule to a target polypeptide or target peptide and typically lyse the target cell or recruit other immune cells to the site of the target cell, thereby killing the target cell.

An "antigenic peptide" is a peptide, which will bind a major histocompatibility complex molecule to form an MHC-peptide complex which is recognized by a T cell, thereby inducing a cytotoxic lymphocyte response upon presentation to the T cell. Thus, antigenic peptides are capable of binding to an appropriate major histocompatibility complex molecule and inducing a cytotoxic T cells response, such as cell lysis or specific cytokine release against the target cell which binds or expresses the antigen. The antigenic peptide can be bound in the context of a class I or class II major histocompatibility complex molecule, on an antigen presenting cell or on a target cell.

In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "anti-sense gene." Anti-sense RNA molecules are capable of binding to mRNA molecules, resulting in an inhibition of mRNA translation.

An "anti-sense oligonucleotide specific for Zcoyto13" or a "Zcyto13 anti-sense oligonucleotide" is an oligonucleotide having a sequence (a) capable of forming a stable triplex with a portion of the Zcyto13 gene, or (b) capable of forming a stable duplex with a portion of an mRNA transcript of the Zcyto13 gene.

A "ribozyme" is a nucleic acid molecule that contains a catalytic center. The term includes RNA enzymes, self-splicing RNAs, self-cleaving RNAs, and nucleic acid molecules that perform these catalytic functions. A nucleic acid molecule that encodes a ribozyme is termed a "ribozyme gene."

An "external guide sequence" is a nucleic acid molecule that directs the endogenous ribozyme, RNase P, to a particular species of intracellular mRNA, resulting in the cleavage of the mRNA by RNase P. A nucleic acid molecule that encodes an external guide sequence is termed an "external guide sequence gene."

The term "variant murine Zcyto13 gene" refers to nucleic acid molecules that encode a polypeptide having an amino acid sequence that is a modification of SEQ ID NO:2. Such variants include naturally-occurring polymorphisms of Zcyto13 genes, as well as synthetic genes that contain conservative amino acid substitutions of the amino acid sequence of SEQ ID NO:2. Additional variant forms of Zcyto13 genes are nucleic acid molecules that contain insertions or deletions of the nucleotide sequences described herein. A variant Zcyto13 gene can be identified by determining whether the gene hybridizes with a nucleic acid molecule having the nucleotide sequence of SEQ ID NO:1, or its complement, under stringent conditions.

Alternatively, variant Zcyto13 genes can be identified by sequence comparison. Two amino acid sequences have "100% amino acid sequence identity" if the amino acid residues of the two amino acid sequences are the same when aligned for maximal correspondence. Similarly, two nucleotide sequences have "100% nucleotide sequence identity" if the nucleotide residues of the two nucleotide sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art (see, for example, Peruski and Peruski, *The Internet and the New Biology: Tools for Genomic and Molecular Research* (ASM Press, Inc. 1997), Wu et al. (eds.), "Information Superhighway and Computer Databases of Nucleic Acids and Proteins," in *Methods in Gene Biotechnology*, pages 123–151 (CRC Press, Inc. 1997), and Bishop (ed.), *Guide to Human Genome Computing*, 2nd Edition (Academic Press, Inc. 1998)). Particular methods for determining sequence identity are described below.

Regardless of the particular method used to identify a variant Zcyto13 gene or variant Zcyto13 polypeptide, a variant gene or polypeptide encoded by a variant gene is functionally characterized by either its anti-viral or anti-proliferative activities, or by the ability to bind specifically to an anti-Zcyto13 antibody.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

The present invention includes functional fragments of Zcyto13 genes. Within the context of this invention, a "functional fragment" of a Zcyto13 gene refers to a nucleic acid molecule that encodes a portion of a Zcyto13 polypeptide, which either (1) possesses an anti-viral or anti-proliferative activity, or (2) specifically binds with an anti-Zcyto13 antibody. For example, a functional fragment of a Zcyto13 gene comprises a portion of the nucleotide sequence of SEQ ID NO:1, and encodes a polypeptide having either an anti-viral or anti-proliferative activity.

Due to the imprecision of standard analytical methods, molecular weights and lengths of polymers are understood to be approximate values. When such a value is expressed as "about" X or "approximately" X, the stated value of X will be understood to be accurate to ±10%.

3. Production of the Zcyto13 Gene

Nucleic acid molecules encoding a murine Zcyto13 gene can be obtained by screening a murine cDNA or genomic library using polynucleotide probes based upon SEQ ID NO:1. These techniques. are standard and well-established.

As an illustration, a nucleic acid molecule that encodes a murine Zcyto13 gene can be isolated from a murine cDNA library. In this case, the first step would be to prepare the cDNA library by isolating RNA from a tissue, such as uterine, heart, or liver tissue, using methods well-known to those of skill in the art. In general, RNA isolation techniques must provide a method for breaking cells, a means of inhibiting RNase-directed degradation of RNA, and a method of separating RNA from DNA, protein, and polysaccharide contaminants. For example, total RNA can be isolated by freezing tissue in liquid nitrogen, grinding the frozen tissue with a mortar and pestle to lyse the cells, extracting the ground tissue with a solution of phenol/chloroform to remove proteins, and separating RNA from the remaining impurities by selective precipitation with lithium chloride (see, for example, Ausubel et al. (eds.), *Short Protocols in Molecular Biology, 3rd Edition,* pages 4–1 to 4–6 (John Wiley & Sons 1995) ["Ausubel (1995)"]; Wu et al., *Methods in Gene Biotechnology,* pages 33–41 (CRC Press, Inc. 1997) ["Wu (1997)"]).

Alternatively, total RNA can be isolated from uterine tissue (or, heart tissue or liver tissue) by extracting ground tissue with guanidinium isothiocyanate, extracting with organic solvents, and separating RNA from contaminants using differential centrifugation (see, for example, Chirgwin et al., *Biochemistry* 18:52 (1979); Ausubel (1995) at pages 4–1 to 4–6; Wu (1997) at pages 33–41).

In order to construct a cDNA library, poly(A)+ RNA must be isolated from a total RNA preparation. Poly(A)+ RNA can be isolated from total RNA using the standard technique of oligo(dT)cellulose chromatography (see, for example, Aviv and Leder, *Proc. Nat'l Acad. Sci. USA* 69:1408 (1972); Ausubel (1995) at pages 4–11 to 4–12).

Double-stranded cDNA molecules are synthesized from poly(A)+ RNA using techniques well-known to those in the art. (see, for example, Wu (1997) at pages 41–46). Moreover, commercially available kits can be used to synthesize double-stranded cDNA molecules. For example, such kits are available from Life Technologies, Inc. (Gaithersburg, Md.), CLONTECH Laboratories, Inc. (Palo Alto, Calif.), Promega Corporation (Madison, Wis.) and STRATAGENE (La Jolla, Calif.).

Various cloning vectors are appropriate for the construction of a cDNA library. For example, a cDNA library can be prepared in a vector derived from bacteriophage, such as a λgt10 vector. See, for example, Huynh et al., "Constructing and Screening cDNA Libraries in λgt10 and λgt11," in *DNA Cloning: A Practical Approach Vol. I, Glover (ed.), page* 49 (IRL Press, 1985); Wu (1997) at pages 47–52.

Alternatively, double-stranded cDNA molecules can be inserted into a plasmid vector, such as a PBLUESCRIPT vector (STRATAGENE; La Jolla, Calif.), a LAMDAGEM-4 (Promega Corp.) or other commercially available vectors. Suitable cloning vectors also can be obtained from the American Type Culture Collection (Manassas, Va.).

To amplify the cloned cDNA molecules, the cDNA library is inserted into a prokaryotic host, using standard techniques. For example, a cDNA library can be introduced into competent *E. coli* DH5 cells, which can be obtained, for example, from Life Technologies, Inc. (Gaithersburg, Md.).

A murine genomic library can be prepared by means well-known in the art (see, for example, Ausubel (1995) at pages 5–1 to 5–6; Wu (1997) at pages 307–327). Genomic DNA can be isolated by lysing tissue with the detergent Sarkosyl, digesting the lysate with proteinase K, clearing insoluble debris from the lysate by centrifugation, precipitating nucleic acid from the lysate using isopropanol, and purifying resuspended DNA on a cesium chloride density gradient.

DNA fragments that are suitable for the production of a genomic library can be obtained by the random shearing of genomic DNA or by the partial digestion of genomic DNA with restriction endonucleases. Genomic DNA fragments can be inserted into a vector, such as a bacteriophage or cosmid vector, in accordance with conventional techniques, such as the use of restriction enzyme digestion to provide appropriate termini, the use of alkaline phosphatase treatment to avoid undesirable joining of DNA molecules, and ligation with appropriate ligases. Techniques for such manipulation are well-known in the art (see, for example, Ausubel (1995) at pages 5–1 to 5–6; Wu (1997) at pages 307–327).

Nucleic acid molecules that encode a murine Zcyto13 gene can also be obtained using the polymerase chain reaction (PCR) with oligonucleotide primers having nucleotide sequences that are based upon the nucleotide sequences of the Zcyto13 gene, as described herein. General methods for screening libraries with PCR are provided by, for example, Yu et al., "Use of the Polymerase Chain Reaction to Screen Phage Libraries," in *Methods in Molecular Biology, Vol.* 15: *PCR Protocols: Current Methods and Applications,* White (ed.), pages 211–215 (Humana Press, Inc. 1993). Moreover, techniques for using PCR to isolate related genes are described by, for example, Preston, "Use of Degenerate Oligonucleotide Primers and the Polymerase Chain Reaction to Clone Gene Family Members," in *Methods in Molecular Biology, Vol.* 15: *PCR Protocols: Current Methods and Applications,* White (ed.), pages 317–337 (Humana Press, Inc. 1993).

A library containing cDNA or genomic clones can be screened with one or more polynucleotide probes based upon SEQ ID NO:1, using standard methods (see, for example, Ausubel (1995) at pages 6–1 to 6–11).

Anti-Zcyto13 antibodies, produced as described below, can also be used to isolate DNA sequences that encode murine Zcyto13 genes from cDNA libraries. For example, the antibodies can be used to screen λgt11 expression libraries, or the antibodies can be used for immunoscreening following hybrid selection and translation (see, for example, Ausubel (1995) at pages 6–12 to 6–16; Margolis et al., "Screening λ expression libraries with antibody and protein probes," in *DNA Cloning* 2: *Expression Systems, 2nd Edition,* Glover et al. (eds.), pages 1–14 (Oxford University Press 1995)).

As an alternative, a Zcyto13 gene can be obtained by synthesizing nucleic acid molecules using mutually priming long oligonucleotides and the nucleotide sequences described herein (see, for example, Ausubel (1995) at pages 8–8 to 8–9). Established techniques using the polymerase chain reaction provide the ability to synthesize DNA molecules at least two kilobases in length (Adang et al., *Plant Molec. Biol.* 21:1131 (1993), Bambot et al., *PCR Methods and Applications* 2:266 (1993), Dillon et al., "Use of the Polymerase Chain Reaction for the Rapid Construction of Synthetic Genes," in *Methods in Molecular Biology, Vol.* 15: *PCR Protocols. Current Methods and Applications,* White (ed.), pages 263–268, (Humana Press, Inc. 1993), and Holowachuk et al., *PCR Methods Appl.* 4:299 (1995)).

The nucleic acid molecules of the present invention can also be synthesized with "gene machines" using protocols such as the phosphoramidate method. If chemically-synthesized double stranded DNA is required for an application such as the synthesis of a gene or a gene fragment, then each complementary strand is made separately. The production of short genes (60 to 80 base pairs) is technically straightforward and can be accomplished by synthesizing the complementary strands and then annealing them. For the production of longer genes (>300 base pairs), however, special strategies may be required, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. For reviews on polynucleotide synthesis, see, for example, Glick and Pasternak, *Molecular Biotechnology, Principles and Applications of Recombinant DNA* (ASM Press 1994), Itakura et al., *Annu. Rev. Biochem.* 53:323 (1984), and Climie et al, *Proc. Nat'l Acad. Sci. USA* 87:633 (1990).

The sequence of a Zcyto13 cDNA or Zcyto13 genomic fragment can be determined using standard methods. Zcyto13 polynucleotide sequences disclosed herein can also be used as probes or primers to clone 5' non-coding regions of a Zcyto13 gene. In view of the tissue-specific expression observed for Zcyto13 by northern blotting, this gene region is expected to provide for preferential expression in heart, liver, brain, kidney, and spleen tissues. Promoter elements from a Zcyto13 gene could thus be used to direct the tissue-specific expression of heterologous genes in, for example, transgenic animals or patients treated with gene therapy. The identification of genomic fragments containing a Zcyto13 promoter or regulatory element can be achieved using well-established techniques, such as deletion analysis (see, generally, Ausubel (1995)).

Cloning of 5' flanking sequences also facilitates production of Zcyto13 proteins by "gene activation," as disclosed in U.S. Pat. No. 5,641,670. Briefly, expression of an endogenous Zcyto13 gene in a cell is altered by introducing into the Zcyto13 locus a DNA construct comprising at least a targeting sequence, a regulatory sequence, an exon, and an unpaired splice donor site. The targeting sequence is a Zcyto13 5' non-coding sequence that permits homologous recombination of the construct with the endogenous Zcyto13 locus, whereby the sequences within the construct become operably linked with the endogenous Zcyto13 coding sequence. In this way, an endogenous Zcyto13 promoter can be replaced or supplemented with other regulatory sequences to provide enhanced, tissue-specific, or otherwise regulated expression.

4. Production of Zcyto13 Gene Variants

The present invention provides a variety of nucleic acid molecules, including DNA and RNA molecules, which encode the Zcyto13 polypeptides disclosed herein. Those skilled in the art will readily recognize that, in view of the degeneracy of the genetic code, considerable sequence variation is possible among these polynucleotide molecules. SEQ ID NO:3 is a degenerate nucleotide sequence that encompasses all nucleic acid molecules that encode the Zcyto13 polypeptide of SEQ ID NO:2. Those skilled in the art will recognize that the degenerate sequence of SEQ ID NO:3 also provides all RNA sequences encoding SEQ ID NO:2, by substituting U for T. Thus, the present invention contemplates Zcyto13 polypeptide-encoding nucleic acid molecules comprising nucleotide 86 to nucleotide 619 of SEQ ID NO:1, and their RNA equivalents.

Table 1 sets forth the one-letter codes used within SEQ ID NO:3 to denote degenerate nucleotide positions. "Resolutions" are the nucleotides denoted by a code letter. "Complement" indicates the code for the complementary nucleotide (s). For example, the code Y denotes either C or T, and its complement R denotes A or G, A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding an amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

Different species can exhibit "preferential codon usage." In general, see, Grantham et al., *Nuc. Acids Res.* 8:1893 (1980), Haas et al. *Curr. Biol.* 6:315 (1996), Wain-Hobson et al., *Gene* 13:355 (1981), Grosjean and Fiers, *Gene* 18:199 (1982), Holm, *Nuc. Acids Res.* 14:3075 (1986), Ikemura, *J. Mol. Biol.* 158:573 (1982), Sharp and Matassi, *Curr. Opin. Genet. Dev.* 4:851 (1994), Kane, *Curr. Opin. Biotechnol.* 6:494 (1995), and Makrides, *Microbiol. Rev.* 60:512 (1996). As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:3 serves as a template for optimizing expression of polynucleotides in various cell types and species commonly used in the art and disclosed herein. Sequences containing preferential codons can be tested and optimized for expression in various species, and tested for functionality as disclosed herein.

The present invention further provides variant polypeptides and nucleic acid molecules that represent counterparts from other species (orthologs). These species include, but are not limited to mammalian, avian, amphibian, reptile, fish, insect and other vertebrate and invertebrate species. Of particular interest are Zcyto13 polypeptides from other mammalian species, including human, porcine, ovine, bovine, canine, feline, equine, and other primate polypeptides. Orthologs of murine Zcyto13 can be cloned using information and compositions provided by the present invention in combination with conventional cloning techniques. For example, a Zcyto13 cDNA can be cloned using mRNA obtained from a tissue or cell type that expresses Zcyto13 as disclosed herein. Suitable sources of mRNA can be identified by probing northern blots with probes designed from the sequences disclosed herein. A library is then prepared from mRNA of a positive tissue or cell line.

A Zcoyto13-encoding cDNA can be isolated by a variety of methods, such as by probing with a complete or partial murine cDNA or with one or more sets of degenerate probes based on the disclosed sequences. A cDNA can also be cloned using the polymerase chain reaction with primers designed from the representative murine Zcyto13 sequences disclosed herein.

In addition, a cDNA library can be used to transform or transfect host cells, and expression of the cDNA of interest can be detected with an antibody to Zcyto13 polypeptide. Kawade et al., *Antiviral Res.* 1:167 (1981), have shown that α types of human and mouse interferon share an antigenic homology. Accordingly, anti-Zycto13 antibodies can be used to isolate human Zcyto13 from natural sources, and to isolate human Zcyto13 sequences from a library that expresses cloned DNA.

Those skilled in the art will recognize that the sequence disclosed in SEQ ID NO:1 represents a single allele of murine Zcyto13, and that allelic variation and alternative splicing are expected to occur. Allelic variants of this sequence can be cloned by probing cDNA or genomic libraries from different individuals according to standard procedures. Allelic variants of the nucleotide sequence shown in SEQ ID NO:1, including those containing silent mutations and those in which mutations result in amino acid sequence changes, are within the scope of the present invention, as are proteins which are allelic variants of SEQ ID NO:2. cDNA molecules generated from alternatively spliced mRNAs, which retain the properties of the Zcyto13 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

Within certain embodiments of the invention, isolated nucleic acid molecules that encode murine Zcyto13 can hybridize to nucleic acid molecules having the nucleotide sequence of SEQ ID NO:1, or a sequence complementary thereto, under "stringent conditions." In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

As an illustration, a nucleic acid molecule encoding a variant Zcyto13 polypeptide can be hybridized with a nucleic acid molecule having the nucleotide sequence of SEQ ID NO:1 (or its complement) at 42° C. overnight in a solution comprising 50% formamide, 5×SSC (1×SSC: 0.15 M sodium chloride and 15 mM sodium citrate), 50 mM sodium phosphate (pH 7.6), 5×Denhardt's solution (100× Denhardt's solution: 2% (w/v) Ficoll 400, 2% (w/v) polyvinylpyrrolidone, and 2% (w/v) bovine serum albumin), 10% dextran sulfate, and 20 μg/ml denatured, sheared salmon sperm DNA. One of skill in the art can devise variations of these hybridization conditions. For example, the hybridization mixture can be incubated at a higher temperature, such as about 65° C., in a solution that does not contain formamide. Moreover, premixed hybridization solutions are available (e.g, EXPRESSHYB Hybridization Solution from CLONTECH Laboratories, Inc.), and hybridization can be performed according to the manufacturer's instructions.

Following hybridization, the nucleic acid molecules can be washed to remove non-hybridized nucleic acid molecules under stringent conditions, or under highly stringent conditions. Typical stringent washing conditions include washing in a solution of 0.5×–2×SSC with 0.1% sodium dodecyl sulfate (SDS) at 55–65° C. That is, nucleic acid molecules encoding a variant Zcyto13 polypeptide remain hybridized with a nucleic acid molecule consisting of the nucleotide sequence of SEQ ID NO:1 (or its complement) following stringent washing conditions, in which the wash stringency is equivalent to 0.5×–2×SSC with 0.1% SDS at 55–65° C., including 0.5×SSC with 0.1% SDS at 55° C., or 2×SSC with 0.1% SDS at 65° C. One of skill in the art can readily devise equivalent conditions, for example, by substituting SSPE for SSC in the wash solution.

Typical highly stringent washing conditions include washing in a solution of 0.1×–0.2×SSC with 0.1% sodium dodecyl sulfate (SDS) at 50–65° C. In other words, nucleic acid molecules encoding a variant Zcyto13 polypeptide remain hybridized with a nucleic acid molecule consisting of the nucleotide sequence of SEQ ID NO:1 (or its complement) following highly stringent washing conditions, in which the wash stringency is equivalent to 0.1×–0.2×SSC with 0.1% SDS at 50–65° C., including 0.1×SSC with 0.1% SDS at 50° C., or 0.2×SSC with 0.1% SDS at 65° C.

The present invention also provides isolated Zcyto13 polypeptides that have a substantially similar sequence identity to the polypeptides of SEQ ID NO:2, or their orthologs. The term "substantially similar sequence identity" is used herein to denote polypeptides having at least 70%, at least 80%, at least 90%, at least 95% or greater than 95% sequence identity to the sequences shown in SEQ ID NO:2, or their orthologs.

The present invention also contemplates Zcyto13 variant nucleic acid molecules that can be identified using two criteria: a determination of the similarity between the encoded polypeptide with the amino acid sequence of SEQ ID NO:2, and a hybridization assay, as described above. Such Zcyto13 variants include nucleic acid molecules (1) that remain hybridized with a nucleic acid molecule consisting of the nucleotide sequence of nucleotides 86 to 619 of SEQ ID NO:1 (or its complement) following stringent washing conditions, in which the wash stringency is equivalent to 0.5x–2xSSC with 0.1% SDS at 55–65° C., and (2) that encode a polypeptide having at least 70%, at least 80%, at least 90%, at least 95% or greater than 95% sequence identity to the amino acid sequence of SEQ ID NO:2. Alternatively, certain Zcyto13 variants can be characterized as nucleic acid molecules (1) that remain hybridized with a nucleic acid molecule consisting of the nucleotide sequence of nucleotides 86 to 619 of SEQ ID NO:1 (or its complement) following highly stringent washing conditions, in which the wash stringency is equivalent to 0.1x–0.2xSSC with 0.1% SDS at 50–65° C., and (2) that encode a polypeptide having at least 70%, at least 80%, at least 90%, at least 95% or greater than 95% sequence identity to the amino acid sequence of SEQ ID NO:2.

Percent sequence identity is determined by conventional methods. See, for example, Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 3 (amino acids are indicated by the standard one-letter codes). The percent identity is then calculated as: ([Total number of identical matches]/[length of the longer sequence plus the number of gaps introduced into the longer sequence in order to align the two sequences])(100).

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative Zcyto13 variant. The FASTA algorithm is described by Pearson and Lipman, *Proc. Nat'l Acad. Sci. USA* 85:2444 (1988), and by Pearson, *Meth. Enzymol.* 183:63 (1990). Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from four to six.

The present invention includes nucleic acid molecules that encode a polypeptide having a conservative amino acid change, compared with the amino acid sequence of SEQ ID

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

NO:2. That is, variants can be obtained that contain one or more amino acid substitutions of SEQ ID NO:2, in which an alkyl amino acid is substituted for an alkyl amino acid in a Zcyto13 amino acid sequence, an aromatic amino acid is substituted for an aromatic amino acid in a Zcyto13 amino acid sequence, a sulfur-containing amino acid is substituted for a sulfur-containing amino acid in a Zcyto13 amino acid sequence, a hydroxy-containing amino acid is substituted for a hydroxy-containing amino acid in a Zcyto13 amino acid sequence, an acidic amino acid is substituted for an acidic amino acid in a Zcyto13 amino acid sequence, a basic amino acid is substituted for a basic amino acid in a Zcyto13 amino acid sequence, or a dibasic monocarboxylic amino acid is substituted for a dibasic monocarboxylic amino acid in a Zcyto13 amino acid sequence.

Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. For example, variant Zcyto13 polypeptides that have an amino acid sequence that differs from SEQ ID NO:2 can be obtained by substituting alanine for $glycine^{39}$, valine for $leucine^{63}$, threonine for $serine^{81}$, valine for $isoleucine^{105}$, or leucine for $valine^{113}$. Additional variants can be obtained by producing polypeptides having two or more of these amino acid substitutions.

The BLOSUM62 table is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" can refer to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Particular variants of murine Zcyto13 are characterized by having at least 70%, at least 80%, at least 90%, at least 95% or greater than 95% sequence identity to the corresponding amino acid sequence (i.e., SEQ ID NO:2), wherein the variation in amino acid sequence is due to one or more conservative amino acid substitutions.

Conservative amino acid changes in a Zcyto13 gene can be introduced by substituting nucleotides for the nucleotides recited in SEQ :ID NO:1 . Such "conservative amino acid" variants can be obtained, for example, by oligonucleotide-directed mutagenesis, linker-scanning mutagenesis, mutagenesis using the polymerase chain reaction, and the like (see Ausubel (1995) at pages 8–10 to 8–22; and McPherson (ed.), *Directed Mutagenesis: A Practical Approach* (IRL Press 1991)). The ability of such variants to promote anti-viral or anti-proliferative activity can be determined using a standard method, such as the assay described herein. Alternatively, a variant Zcyto13 polypeptide can be identified by the ability to specifically bind anti-Zcyto13 antibodies.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an *E. coli* S30 extract and commercially available enzymes and other reagents. Proteins are purified by chromatography. See, for example, Robertson et al., *J. Am. Chem. Soc.* 113:2722 (1991), Ellman et al., *Methods Enzymol.* 202:301 (1991), Chung et al., *Science* 259:806 (1993), and Chung et al., *Proc. Nat'l Acad. Sci. USA* 90:10145 (1993).

In a second method, translation is carried out in *Xenopus oocytes* by microinjection of mutated mRNA and chemically aminoacylated suppressor tRNAs (Turcatti et al., *J. Biol. Chem.* 271:19991 (1996)). Within a third method, *E. coli* cells are cultured in the absence of a natural amino acid that is to be replaced (e.g, phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470 (1994). Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395 (1993)).

A limited number of non-conservative amino acids, amino acids that are not encoded by the genetic code, non-naturally occurring amino acids, and unnatural amino acids may be substituted for Zcyto13 amino acid residues.

Essential amino acids in the polypeptides of the present invention can be identified according to procedures known in the art, such as site-directed mutagenesis or alanine-scanning mutagenesis (Cunningham and Wells, *Science* 244:1081 (1989), Bass et al., *Proc. Nat'l Acad. Sci. USA* 88:4498 (1991), Coombs and Corey, "Site-Directed Mutagenesis and Protein Engineering," in *Proteins: Analysis and Design,* Angeletti (ed.), pages 259–311 (Academic Press, Inc. 1998)). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699 (1996). The identities of essential amino acids can also be inferred from analysis of homologies with interferon-α, interferon-β, interferon-γ, interferon-δ, interferon-ω, and interferon-τ, and particularly, by analysis of the murine interferon-α family members.

Sequence analysis can also identify motifs that reside within murine interferon polypeptides. As an illustration, the following murine interferon sequences were analyzed for common amino acid sequence motifs: nine murine interferon-α polypeptides, interferon-β, interferon-δ, and Zcyto13. The results of this analysis revealed two motifs in the interferon sequences. One motif occurs at amino acid residues 45 to 59 of Zcyto13, and has the following sequence: [FSPN][PFG][LK][RSI][CN]L[KT][DY][IR] [TQKA]DF[GK][FI]P, wherein acceptable amino acids for a given position are indicated within square brackets ("murine interferon motif 1"). Zcyto13 can be distinguished from other murine interferons when the motif is further defined by the following conditions: (1) the first residue of the sequence is F, or (2) the fourth residue is R, or (3) the ninth residue is I, or (4) the tenth residue is T. Accordingly, the present invention includes polypeptides that comprise an amino acid motif having the sequence [FSPN][PFG][LK][RSI][CN]L[KT][DY][IR][TQKA]DF[GK][FI]P, wherein the sequence is further defined by at least one of the following conditions: the first residue is F, the fourth residue is R, the ninth residue is I, or the tenth residue is T.

A second motif occurs at amino acid residues 152 to 170 of Zcyto13, and has the following amino acid sequence: [KVR][FY]L[IRK][NEKL][KM]K[YH][SN][FPLS][CY]AW[KEM][IV][IV][TR][VA]E, wherein acceptable amino acids for a given position are indicated within square brackets ("murine interferon motif 2"). Zcyto13 can be distinguished from other murine interferons when the motif is further defined by one of the following conditions: (1) the first residue is K, or (2) the fourth residue is I, or (3) the fifth residue is N, or (4) the tenth residue is F, or (5) the fourteenth residue is K, or (6) the fifteenth residue is I, or (7) the seventeenth residue is T, or (8) the eighteenth residue is V. Thus, the present invention includes polypeptides that comprise an amino acid motif having the sequence: [KVR][FY]L[IRK][NEKL][KM]K[YH][SN][FPLS][CY]AW[KEM][IV][IV][TR][VA]E, wherein the sequence is further defined by at least one of the following conditions: the first residue is K, the fourth residue is I, the fifth residue is N, the tenth residue is F, the fourteenth residue is K, the fifteenth residue is I, the seventeenth residue is T, or the eighteenth residue is V. The present invention also includes polypeptides having both murine interferon motifs 1 and 2.

Although sequence analysis can be used to identify Zcyto13 receptor binding sites, the location of Zcyto13 receptor binding domains can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306 (1992), Smith et al., *J. Mol. Biol.* 224:899 (1992), and Wlodaver et al., *FEBS Lett.* 309:59 (1992). Moreover, Zcyto13 labeled with biotin or FITC can be used for expression cloning of Zcyto13 receptors.

To date, studies have identified two main receptor binding sites in Type I interferons: one at a high affinity responsible for the binding to the receptor, and another site at lower affinity involved in mediating signal transduction (see, for example, Viscomi, *Biotherapy* 10:59 (1997)). The first site engages Helices A and B, and Loop AB, while the second site engages Helices A and C and Loop DE. Accordingly, mutations can be introduced into Helix C or Loop DE to interfere with Zcyto13 receptor signaling. Such a mutant would be expected to bind a Zcyto13 receptor without producing a biological effect, and therefore, would have the properties of a Zcyto13 antagonist. As shown in Table 4, Helix C and Loop DE are represented by amino acids 99 to 124, and 156 to 160, respectively, of SEQ ID NO:2. Another form of Zcyto13 antagonist could consist of Helices A and B, and Loop AB of the Zcyto13 form described herein (i.e., amino acids 22 to 89 of SEQ ID NO:2).

TABLE 4

| Structural Feature of Zcyto13 | Amino Acid Residues of SEQ ID NO: 2 | Nucleotides of SEQ ID NO: 1 |
|---|---|---|
| Signal sequence | 1—21 | 23—85 |
| Helix A | 22—45 | 86—157 |
| AB Loop | 46—64 | 158—214 |
| Helix B | 65—89 | 215—289 |
| BC Loop | 90—98 | 290—316 |
| Helix C | 99—124 | 317—394 |
| CD Loop | 125—133 | 395—421 |
| Helix D | 134—155 | 422—487 |
| DE Loop | 156—160 | 488—502 |
| Helix E | 161—188 | 503—586 |

Multiple amino acid substitutions can be made and tested using known methods of mutagenesis and screening, such as those disclosed by Reidhaar-Olson and Sauer (*Science* 241:53 (1988)) or Bowie and Sauer (*Proc. Nat'l Acad. Sci. USA* 86:2152 (1989)). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832 (1991), Ladner et al., U.S. Pat. No. 5,223,409, Huse, international publication No. WO 92/06204, and region-directed mutagenesis (Derbyshire et al., *Gene* 46:145 (1986), and Ner et al., *DNA* 7:127, (1988)).

Variants of the disclosed Zcyto13 nucleotide and polypeptide sequences can also be generated through DNA shuffling as disclosed by Stemmer, *Nature* 370:389 (1994), Stemmer, *Proc. Nat'l Acad. Sci. USA* 91:10747 (1994), and international publication No. WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind with anti-Zcyto13 antibodies, can be recovered from the host cells and rapidly sequenced using modem equipment. These methods allow the rapid determination of the importance of individual amino acid residues in a polypeptide of interest, and can be applied to polypeptides of unknown structure.

The present invention also includes "functional fragments" of Zcyto13 polypeptides and nucleic acid molecules encoding such functional fragments. Routine deletion analyses of nucleic acid molecules can be performed to obtain functional fragments of a nucleic acid molecule that encodes a Zcyto13 polypeptide. As an illustration, DNA molecules having the nucleotide sequence of SEQ ID NO:1 can be digested with Bal31 nuclease to obtain a series of nested deletions. The fragments are then inserted into expression vectors in proper reading frame, and the expressed polypeptides are isolated and tested for anti-viral or antiproliferative activity, or for the ability to bind anti-Zcyto13 antibodies. One alternative to exonuclease digestion is to use oligonucleotide-directed mutagenesis to introduce deletions or stop codons to specify production of a desired fragment. Alternatively, particular fragments of a Zcyto13 gene can be synthesized using the polymerase chain reaction.

Studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993), Content et al., "Expression and preliminary deletion analysis of the 42 kDa 2–5A synthetase induced by human interferon," in *Biological Interferon Systems, Proceedings of ISIR-TNO Meeting on Interferon Systems,* Cantell (ed.), pages 65–72 (Nijhoff 1987), Herschman, "The EGF Receptor," in *Control of Animal Cell Proliferation, Vol. 1,* Boynton et al., (eds.) pages 169–199 (Academic Press 1985), Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995), and Meisel et al., *Plant Molec. Biol.* 30:1 (1996).

The present invention also contemplates functional fragments of a Zcyto13 gene that has amino acid changes, compared with the amino acid sequence of SEQ ID NO:2. A variant Zcyto13 gene can be identified on the basis of structure by determining the level of identity with nucleotide and amino acid sequence of SEQ ID NO:2, as discussed above. An alternative approach to identifying a variant gene on the basis of structure is to determine whether a nucleic acid molecule encoding a potential variant Zcyto13 gene can hybridize to a nucleic acid molecule having the nucleotide sequence of SEQ ID NO:1, as discussed above.

The present invention also provides polypeptide fragments or peptides comprising an epitope-bearing portion of a Zcyto13 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies that bind with the polypeptides described herein.

Antigenic epitope-bearing peptides and polypeptides can contain at least four to ten amino acids, at least ten to fifteen amino acids, or about 15 to about 30 amino acids of SEQ ID NO:2. Such epitope-bearing peptides and polypeptides can be produced by fragmenting a Zcyto13 polypeptide, or by chemical peptide synthesis, as described herein. Moreover, epitopes can be selected by phage display of random peptide libraries (see, for example, Lane and Stephen, *Curr. Opin. Immunol.* 5:268 (1993), and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology, Vol. 10,* Manson (ed.), pages 105–116 (The Humana Press, Inc. 1992), Price, "Production and Characterization of Synthetic Peptide-Derived Antibodies," in *Monoclonal Antibodies: Production, Engineering, and Clinical Application,* Ritter and Ladyman (eds.), pages 60–84 (Cambridge University Press 1995), and Coligan et al. (eds.), *Current Protocols in Immunology,* pages 9.3.1–9.3.5 and pages 9.4.1–9.4.11 (John Wiley & Sons 1997).

Regardless of the particular nucleotide sequence of a variant Zcyto13 gene, the gene encodes a polypeptide that is characterized by its anti-viral or anti-proliferative activity, or by the ability to bind specifically to an anti-Zcyto13 antibody. More specifically, variant murine Zcyto13 genes encode polypeptides, which exhibit at least 50%, or, greater than 70, 80, or 90%, of the activity of polypeptide encoded by the murine Zcyto13 gene described herein.

For any Zcyto13 polypeptide, including variants and fusion proteins, one of ordinary skill in the art can readily generate a fully degenerate polynucleotide sequence encoding that variant using the information set forth in Tables 1 and 2 above. Moreover, those of skill in the art can use standard software to devise Zcyto13 variants based upon the nucleotide and amino acid sequences described herein. Accordingly, the present invention includes a computer-readable medium encoded with a data structure that provides at least one of the following sequences: SEQ ID NO:1, SEQ ID NO:2, SEQ ID NO:3, SEQ ID NO:5, SEQ ID NO:6, SEQ ID NO:7, SEQ ID NO:8, SEQ ID NO:9, SEQ ID NO:10, and SEQ ID NO:11. Suitable forms of computer-readable media include magnetic media and optically-readable media. Examples of magnetic media include a hard or fixed drive, a random access memory (RAM) chip, a floppy disk, digital linear tape (DLT), a disk cache, and a ZIP disk. Optically readable media are exemplified by compact discs (e.g., CD-read only memory (ROM), CD-rewritable (RW), and CD-recordable), and digital versatile/video discs (DVD) (e.g., DVD-ROM, DVD-RAM, and DVD+RW).

5. Production of Zcyto13 Fusion Proteins and Conjugates

Fusion proteins of Zcyto13 can be used to express Zcyto13 in a recombinant host, and to isolate expressed Zcytol13. As described below, particular Zcyto13 fusion proteins also have uses in diagnosis and therapy.

One type of fusion protein comprises a peptide that guides a Zcyto13 polypeptide from a recombinant host cell. To direct a Zcyto13 polypeptide into the secretory pathway of a eukaryotic host cell, a secretory signal sequence (also known as a signal peptide, a leader sequence, prepro sequence or pre sequence) is provided in the Zcyto13 expression vector. While the secretory signal sequence may be derived from Zcyto13, a suitable signal sequence may also be derived from another secreted protein or synthesized de novo. The secretory signal sequence is operably linked to a Zcyto13-encoding sequence such that the two sequences are joined in the correct reading frame and positioned to direct the newly synthesized polypeptide into the secretory pathway of the host cell. Secretory signal sequences are commonly positioned 5' to the nucleotide sequence encoding the polypeptide of interest, although certain secretory signal sequences may be positioned elsewhere in the nucleotide sequence of interest (see, e.g., Welch et al., U.S. Pat. No. 5,037,743; Holland et al., U.S. Pat. No. 5,143,830).

Although the secretory signal sequence of Zcyto13 or another protein produced by mammalian cells (e.g., tissue-type plasminogen activator signal sequence, as described, for example, in U.S. Pat. No. 5,641,655) is useful for expression of Zcyto13 in recombinant mammalian hosts, a yeast signal sequence is preferred for expression in yeast cells. Examples of suitable yeast signal sequences are those derived from yeast mating phermone α-factor (encoded by the MFα1 gene), invertase (encoded by the SUC2 gene), or acid phosphatase (encoded by the PHO5 gene). See, for example, Romanos et al., "Expression of Cloned Genes in Yeast," in *DNA Cloning 2: A Practical Approach, 2$^{nd}$ Edition*, Glover and Hames (eds.), pages 123–167 (Oxford University Press 1995).

In bacterial cells, it is often desirable to express a heterologous protein as a fusion protein to decrease toxicity, increase stability, and to enhance recovery of the expressed protein. For example, Zcyto13 can be expressed as a fusion protein comprising a glutathione S-transferase polypeptide. Glutathione S-transferease fusion proteins are typically soluble, and easily purifiable from *E. coli* lysates on immobilized glutathione columns. In similar approaches, a Zcyto13 fusion protein comprising a maltose binding protein polypeptide can be isolated with an amylose resin column, while a fusion protein comprising the C-terminal end of a truncated Protein A gene can be purified using IgG-Sepharose. Established techniques for expressing a heterologous polypeptide as a fusion protein in a bacterial cell are described, for example, by Williams et al., "Expression of Foreign Proteins in *E. coli* Using Plasmid Vectors and Purification of Specific Polyclonal Antibodies," in *DNA Cloning 2: A Practical Approach*, 2nd Edition, Glover and Hames (Eds.), pages 15–58 (Oxford University Press 1995). In addition, commercially available expression systems are available. For example, the PINPOINT Xa protein purification system (Promega Corporation; Madison, Wis.) provides a method for isolating a fusion protein comprising a polypeptide that becomes biotinylated during expression with a resin that comprises avidin.

Peptide tags that are useful for isolating heterologous polypeptides expressed by either prokaryotic or eukaryotic cells include polyHistidine tags (which have an affinity for nickel-chelating resin), c-myc tags, calmodulin binding protein (isolated with calmodulin affinity chromatography), substance P, the RYIRS tag (which binds with anti-RYIRS antibodies), the Glu-Glu tag, and the FLAG tag (which binds with anti-FLAG antibodies). See, for example, Luo et al., *Arch. Biochem. Biophys.* 329:215 (1996), Morganti et al., *Biotechnol. Appl. Biochem.* 23:67 (1996), and Zheng et al., *Gene* 186:55 (1997). Nucleic acid molecules encoding such peptide tags are available, for example, from Sigma-Aldrich Corporation (St. Louis, Mo.).

The present invention also contemplates that the use of the secretory signal sequence contained in the Zcyto13 polypeptides of the present invention to direct other polypeptides into the secretory pathway. A signal fusion polypeptide can be made wherein a secretory signal sequence derived from amino acid residues 1 to 21 of SEQ ID NO:2 is operably linked to another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted: protein, such as a receptor. Such fusions may be used in a transgenic animal or in a cultured recombinant host to direct peptides through the secretory pathway. With regard to the latter, exemplary polypeptides include pharmaceutically active molecules such as Factor VIIa, proinsulin, insulin, follicle stimulating hormone, tissue type plasminogen activator, tumor necrosis factor, interleukins (e.g., interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, and IL-18), colony stimulating factors (e.g., granulocyte-colony stimulating factor (G-CSF) and granulocyte macrophage-colony stimulating factor (GM-CSF)), interferons (e.g., interferons-α, -β, -γ, -ω, -δ, -τ, and -ε), the stem cell growth factor designated "S1 factor," erythropoietin, and thrombopoietin. The Zcyto13 secretory signal sequence contained in the fusion polypeptides of the present invention is preferably fused amino-terminally to an additional peptide to direct the additional peptide into the secretory pathway. Fusion proteins comprising a Zcyto13 secretory signal sequence can be constructed using standard techniques.

Another form of fusion protein comprises a Zcyto13 polypeptide and an immunoglobulin heavy chain constant region, typically an $F_c$ fragment, which contains two or three constant region domains and a hinge region but lacks the variable region. As an illustration, Chang et al., U.S. Pat. No. 5,723,125, describe a fusion protein comprising a human interferon and a human immunoglobulin Fc fragment. The C-terminal of the interferon is linked to the N-terminal of the Fc fragment by a peptide linker moiety. An example of a peptide linker is a peptide comprising primarily a T cell inert sequence, which is immunologically inert. An exemplary peptide linker has the amino acid sequence: GGSGG SGGGG SGGGG S (SEQ ID NO:4). In this fusion protein, a preferred Fc moiety is a human γ4 chain, which is stable in solution and has little or no complement activating activity. Accordingly, the present invention contemplates a Zcyto13 fusion protein that comprises a Zcyto13 moiety and a human Fc fragment, wherein the C-terminus of the Zcyto13 moiety is attached to the N-terminus of the Fc fragment via a peptide linker, such as a peptide consisting of the amino acid sequence of SEQ ID NO:4. The Zcyto13 moiety can be a Zcyto13 molecule or a fragment thereof.

In another variation, a Zcyto13 fusion protein comprises an IgG sequence, a Zcyto13 moiety covalently joined to the aminoterminal end of the IgG sequence, and a signal peptide that is covalently joined to the aminoterminal of the Zcyto13 moiety, wherein the IgG sequence consists of the following elements in the following order: a hinge region, a $CH_2$ domain, and a $CH_3$ domain. Accordingly, the IgG sequence lacks a $CH_1$ domain. The Zcyto13 moiety displays a Zcyto13 activity, as described herein, such as the ability to bind with a Zcyto13 receptor. This general approach to producing fusion proteins that comprise both antibody and nonantibody portions has been described by LaRochelle et al., EP 742830 (WO 95/21258).

Fusion proteins comprising a Zcyto13 moiety and an Fc moiety can be used, for example, as an in vitro assay tool. For example, the presence of an Zcyto13 receptor in a biological sample can be detected using a Zcoyto13-immunoglobulin fusion protein, in which the Zcyto13 moiety is used to target the cognate receptor, and a macromolecule, such as Protein A or anti-Fc antibody, is used to detect the bound fusion protein-receptor complex. Moreover, such fusion proteins can be used to identify agonists and antagonists that interfere with the binding of Zcyto13 to its receptor.

In addition, antibody-Zcyto13 fusion proteins, comprising antibody variable domains, are useful as therapeutic proteins, in which the antibody moiety binds with a target antigen, such as a tumor associated antigen. Methods of making antibody-cytokine fusion proteins are known to those of skill in the art. For example, antibody fusion proteins comprising an interleukin-2 moiety are described by Boleti et al., *Ann. Oncol.* 6:945 (1995), Nicolet et al., *Cancer Gene Ther.* 2:161 (1995), Becker et al., *Proc. Nat'l Acad. Sci. USA* 93:7826 (1996), Hank et al., *Clin. Cancer Res.* 2:1951 (1996), and Hu et al., *Cancer Res.* 56:4998 (1996). Moreover, Yang et al., *Hum. Antibodies Hybridomas* 6:129 (1995), and Xiang et al., *J. Biotechnol.* 53:3 (1997), describe fusion proteins that include an F(ab')$_2$ fragment and a tumor necrosis factor alpha moiety. Additional cytokine-antibody fusion proteins include IL-8, IL-12, or interferon-τ as the cytokine moiety (Holzer et al., *Cytokine* 8:214 (1996); Gillies et al., *J. Immunol.* 160:6195 (1998); Xiang et al., *Hum. Antibodies Hybridomas* 7:2 (1996)). Also see, Gillies, U.S. Pat. No. 5,650,150.

Moreover, using methods described in the art, hybrid Zcyto13 proteins can be constructed using regions or domains of the inventive Zcyto13 in combination with those of other interferon family proteins (i.e., interferon-α, interferon-β, interferon-γ, interferon-δ, interferon-ω, and interferon-τ), or heterologous proteins (see, for example, Picard, *Cur. Opin. Biology* 5:511 (1994)). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptides of unknown structure. For example Horisberger and DiMarco, *Pharmac. Ther.* 66:507 (1995), describe the construction of fusion protein hybrids comprising different interferon-α subtypes, as well as hybrids comprising interferon-α domains from different species (also see, Van Heuvel et al., *J. Gen. Virol.* 67:2215 (1986)).

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. For example, part or all of a domain(s) conferring a biological function may be swapped between interferon-α of the present invention with the functionally equivalent domain(s) from another interferon-α, or from another family member, such as interferon-β, interferon-δ, interferon-γ, interferon-ω, or interferon-τ. Such domains include, but are not limited to, the secretory signal sequence, helices A, B, C, D, and E, and loops AB, BC, CD, and DE. Such fusion proteins would be expected to have a biological functional profile that is the same or similar to polypeptides of the present invention or other known interferon family proteins, depending on the fusion constructed. Moreover, such fusion proteins may exhibit other properties as disclosed herein. General methods for enzymatic and chemical cleavage of fusion proteins are described, for example, by Ausubel (1995) at pages 16–19 to 16–25.

The present invention also contemplates chemically modified Zcyto13 compositions, in which a Zcyto13 polypeptide is linked with a polymer. Typically, the polymer is water soluble so that the Zcyto13 conjugate does not precipitate in an aqueous environment, such as a physiological environment. An example of a suitable polymer is one that has been modified to have a single reactive group, such as an active ester for acylation, or an aldehyde for alkylation. In this way, the degree of polymerization can be controlled. An example of a reactive aldehyde is polyethylene glycol propionaldehyde, or mono-(C1–C10) alkoxy, or aryloxy derivatives thereof (see, for example, Harris, et al., U.S. Pat. No. 5,252,714). The polymer may be branched or unbranched. Moreover, a mixture of polymers can be used to produce Zcyto13 conjugates.

Zcyto13 conjugates used for therapy can comprise pharmaceutically acceptable water-soluble polymer moieties. Conjugation of interferons with water-soluble polymers has been shown to enhance the circulating half-life of the interferon, and to reduce the immunogenicity of the polypeptide (see, for example, Nieforth et al., *Clin. Pharmacol. Ther.* 59:636 (1996), and Monkarsh et al., *Anal. Biochem.* 247:434 (1997)).

Suitable water-soluble polymers include polyethylene glycol (PEG), monomethoxy-PEG, mono-(C1–C10)alkoxy-PEG, aryloxy-PEG, poly-p-vinyl pyrrolidone)PEG, tresyl monomethoxy PEG, PEG propionaldehyde, bis-succinimidyl carbonate PEG, propylene glycol homopolymers, a polypropylene oxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A Zcyto13 conjugate can also comprise a mixture of such water-soluble polymers.

One example of a Zcyto13 conjugate comprises a Zcyto13 moiety and a polyalkyl oxide moiety attached to the N-terminus of the Zcyto13 moiety. PEG is one suitable polyalkyl oxide. As an illustration, Zcyto13 can be modified with PEG, a process known as "PEGylation." PEGylation of Zcyto13 can be carried out by any of the PEGylation reactions known in the art (see, for example, EP 0 154 316, Delgado et al., *Critical Reviews in Therapeutic Drug Carrier Systems* 9:249 (1992), Duncan and Spreafico, *Clin. Pharmacokinet.* 27:290 (1994), and Francis et al., *Int J Hematol* 68:1 (1998)). For example, PEGylation can be performed by an acylation reaction or by an alkylation reaction with a reactive polyethylene glycol molecule. In an alternative approach, Zcyto13 conjugates are formed by condensing activated PEG, in which a terminal hydroxy or amino group of PEG has been replaced by an activated linker (see, for example, Karasiewicz et al., U.S. Pat. No. 5,382,657).

PEGylation by acylation typically requires reacting an active ester derivative of PEG with a Zcyto13 polypeptide. An example of an activated PEG ester is PEG esterified to N-hydroxysuccinimide. As used herein, the term "acylation" includes the following types of linkages between Zcyto13 and a water soluble polymer: amide, carbamate, urethane, and the like. Methods for preparing PEGylated Zcyto13 by acylation will typically comprise the steps of (a) reacting a Zcyto13 polypeptide with PEG (such as a reactive ester of an aldehyde derivative of PEG) under conditions whereby one or more PEG groups attach to Zcyto13, and (b) obtaining the reaction product(s). Generally, the optimal reaction conditions for acylation reactions will be determined based upon known parameters and desired results. For example, the larger the ratio of PEG:Zcyto13, the greater the percentage of polyPEGylated Zcyto13 product.

The product of PEGylation by acylation is typically a polyPEGylated Zcyto13 product, wherein the lysine ε-amino groups are PEGylated via an acyl linking group. An example of a connecting linkage is an amide. Typically, the resulting Zcyto13 will be at least 95% mono-, di-, or tri-pegylated, although some species with higher degrees of PEGylation may be formed depending upon the reaction conditions. PEGylated species can be separated from unconjugated Zcyto13 polypeptides using standard purification methods, such as dialysis, ultrafiltration, ion exchange chromatography, affinity chromatography, and the like.

PEGylation by alkylation generally involves reacting a terminal aldehyde derivative of PEG with Zcyto13 in the presence of a reducing agent. PEG groups are preferably attached to the polypeptide via a —CH$_2$—NH group.

Derivatization via reductive alkylation to produce a monoPEGylated product takes advantage of the differential reactivity of different types of primary amino groups available for derivatization. Typically, the reaction is performed at a pH that allows one to take advantage of the pKa differences between the ε-amino groups of the lysine residues and the α-amino group of the N-terminal residue of the protein. By such selective derivatization, attachment of a water-soluble polymer that contains a reactive group such as an aldehyde, to a protein is controlled. The conjugation with the polymer occurs predominantly at the N-terminus of the protein without significant modification of other reactive groups such as the lysine side chain amino groups. The present invention provides a substantially homogenous preparation of Zcyto13 monopolymer conjugates.

Reductive alkylation to produce a substantially homogenous population of monopolymer Zcyto13 conjugate molecule can comprise the steps of: (a) reacting a Zcyto13 polypeptide with a reactive PEG under reductive alkylation conditions at a pH suitable to permit selective modification of the α-amino group at the amino terminus of the Zcyto13, and (b) obtaining the reaction product(s). The reducing agent used for reductive alkylation should be stable in aqueous solution and preferably be able to reduce only the Schiff base formed in the initial process of reductive alkylation. Preferred reducing agents include sodium borohydride, sodium cyanoborohydride, dimethylamine borane, trimethylamine borane, and pyridine borane.

For a substantially homogenous population of monopolymer Zcyto13 conjugates, the reductive alkylation reaction conditions are those which permit the selective attachment of the water soluble polymer moiety to the N-terminus of Zcyto13. Such reaction conditions generally provide for pKa differences between the lysine amino groups and the α-amino group at the N-terminus. The pH also affects the ratio of polymer to protein to be used. In general, if the pH is lower, a larger excess of polymer to protein will be desired because the less reactive the N-terminal. α-group, the more polymer is needed to achieve optimal conditions. If the pH is higher, the polymer:Zcyto13 need not be as large because more reactive groups are available. Typically, the pH will fall within the range of 3–9, or 3–6.

Another factor to consider is the molecular weight of the water-soluble polymer. Generally, the higher the molecular weight of the polymer, the fewer number of polymer molecules which may be attached to the protein. For PEGylation reactions, the typical molecular weight is about 2 kDa to about 100 kDa, about 5 kDa to about 50 kDa, or about 12 kDa to about 25 kDa. The molar ratio of water-soluble polymer to Zcyto13 will generally be in the range of 1:1 to 100:1. Typically, the molar ratio of water-soluble polymer to Zcyto13 will be 1:1 to 20:1 for polyPEGylation, and 1:1 to 5:1 for monoPEGylation.

General methods for producing conjugates comprising interferon and water-soluble polymer moieties are known in the art. See, for example, Karasiewicz et al., U.S. Pat. No. 5,382,657, Greenwald et al., U.S. Pat. No. 5,738, 846, Nieforth et al., *Clin. Pharmacol. Ther.* 59:636 (1996), Monkarsh et al., *Anal. Biochem.* 247:434 (1997)).

The present invention contemplates compositions comprising a peptide or polypeptide described herein. Such compositions can further comprise a carrier. The carrier can be a conventional organic or inorganic carrier. Examples of carriers include water, buffer solution, alcohol, propylene glycol, macrogol, sesame oil, corn oil, and the like.

Peptides and polypeptides of the present invention comprise at least six, at least nine, or at least 15 contiguous amino acid residues of the following amino acid sequences within SEQ ID NO:2: amino acid residues 22 to 199, amino acid residues 22 to 188, amino acid residues 22 to 45, amino acid residues 46 to 64, amino acid residues 65 to 89, amino acid residues 90 to 98, amino acid residues 99 to 124, amino acid residues 125 to 133, amino acid residues 134 to 155, amino acid residues 22 to 89, and amino acid residues 161 to 181. Within certain embodiments of the invention, the polypeptides comprise 20, 30, 40, 50, 100, or more contiguous residues of these amino acid sequences. Nucleic acid molecules encoding such peptides and polypeptides are useful as polymerase chain reaction primers and probes.

6. Production of Zcyto13 Polypeptides in Cultured Cells

The polypeptides of the present invention, including full-length polypeptides, functional fragments, and fusion proteins, can be produced in recombinant host cells following conventional techniques. To express a Zcyto13 gene, a nucleic acid molecule encoding the polypeptide must be operably linked to regulatory sequences that control transcriptional expression in an expression vector and then, introduced into a host cell. In addition to transcriptional regulatory sequences, such as promoters and enhancers, expression vectors can include translational regulatory sequences and a marker gene, which is suitable for selection of cells that carry the expression vector.

Expression vectors that are suitable for production of a foreign protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. As discussed above, expression vectors can also include nucleotide sequences encoding a secretory sequence that directs the heterologous polypeptide into the secretory pathway of a host cell. For example, a Zcyto13 expression vector may comprise a Zcyto13 gene and a secretory sequence derived from a Zcyto13 gene or another secreted gene.

Zcyto13 proteins of the present invention may be expressed in mammalian cells. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44 [Chasin et al., *Som. Cell. Molec. Genet.* 12:555 (1986)]), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis.

Suitable eukaryotic promoters include the promoter of the mouse metallothionein I gene (Hamer et al., *J. Molec. Appl. Genet.* 1:273 (1982)), the TK promoter of Herpes virus (McKnight, *Cell* 31:355 (1982)), the SV40 early promoter (Benoist et al., *Nature* 290:304 (1981)), the Rous sarcoma virus promoter (Gorman et al., *Proc. Nat'l Acad. Sci. USA* 79:6777 (1982)), the cytomegalovirus promoter (Foecking et al., *Gene* 45:101 (1980)), and the mouse mammary tumor virus promoter (see, generally, Etcheverry, "Expression of Engineered Proteins in Mammalian Cell Culture," in *Protein Engineering: Principles and Practice,* Cleland et al. (eds.), pages 163–181 (John Wiley & Sons, Inc. 1996)).

Alternatively, a prokaryotic promoter, such as the bacteriophage T3 RNA polymerase promoter, can be used to control Zcyto13 gene expression in mammalian cells if the prokaryotic promoter is regulated by a eukaryotic promoter (Zhou et al., *Mol. Cell. Biol.* 10:4529 (1990), and Kaufman et al., *Nucl. Acids Res.* 19:4485 (1991)).

An expression vector can be introduced into host cells using a variety of standard techniques including calcium phosphate transfection, liposome-mediated transfection, microprojectile-mediated delivery, electroporation, and the like. The transfected cells can be selected and propagated to provide recombinant host cells that comprise the expression vector stably integrated in the host cell genome. Techniques for introducing vectors into eukaryotic cells and techniques for selecting such stable transformants using a dominant selectable marker are described, for example, by Ausubel (1995) and by Murray (ed.), *Gene Transfer and Expression Protocols* (Humana Press 1991).

For example, one suitable selectable marker is a gene that provides resistance to the antibiotic neomycin. In this case, selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A suitable amplifiable selectable marker is dihydrofolate reductase, which confers resistance to methotrexate. Other drug resistance genes (e.g., hygromycin resistance, multi-drug resistance, puromycin acetyltransferase) can also be used. Alternatively, markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Zcyto13 polypeptides can also be produced by cultured mammalian cells using a viral delivery system. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous nucleic acid (for a review, see Becker et al., *Meth. Cell Biol.* 43:161 (1994), and Douglas and Curiel, *Science & Medicine* 4:44 (1997)). Advantages of the adenovirus system include the accommodation of relatively large DNA inserts, the ability to grow to high-titer, the ability to infect a broad range of mammalian cell types, and flexibility that allows use with a large number of available vectors containing different promoters.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. An option is to delete the essential E1 gene from the viral vector, which results in the inability to replicate unless the E1 gene is provided by the host cell. A Adenovirus vector-infected human 293 cells (ATCC Nos. CRL-1573, 45504, 45505), for example, can be grown as adherent cells or in suspension culture at relatively high cell density to produce significant amounts of protein (see Gamier et al., *Cytotechnol.* 15:145 (1994)).

Zcyto13 may also be expressed in other higher eukaryotic cells, such as avian, fungal, insect, yeast, or plant cells. The baculovirus system provides an efficient means to introduce cloned Zcyto13 genes into insect cells. Suitable expression vectors are based upon the *Autographa californica* multiple nuclear polyhedrosis virus (AcMNPV), and contain well-known promoters such as Drosophila heat shock protein (hsp) 70 promoter, *Autographa californica* nuclear polyhedrosis virus immediate-early gene promoter (ie-1) and the delayed early 39K promoter, baculovirus p10 promoter, and the *Drosophila metallothionein* promoter. A second method of making recombinant baculovirus utilizes a transposon-based system described by Luckow (Luckow, et al., *J. Virol.* 67:4566 (1993)). This system, which utilizes transfer vectors, is sold in the BAC-to-BAC kit (Life Technologies, Rockville, Md.). This system utilizes a transfer vector, PFASTBAC (Life Technologies) containing a Tn7 transposon to move the DNA encoding the Zcyto13 polypeptide into a baculovirus genome maintained in *E. coli* as a large plasmid called a "bacmid." See, Hill-Perkins and Possee, *J. Gen. Virol.* 71:971 (1990), Bonning, et al., *J. Gen. Virol.* 75:1551 (1994), and Chazenbalk, and Rapoport, *J. Biol. Chem.* 270:1543 (1995). In addition, transfer vectors can include an in-frame fusion with DNA encoding an epitope tag at the C- or N-terminus of the expressed Zcyto13 polypeptide, for example, a Glu-Glu epitope tag (Grussenmeyer et al., *Proc. Nat'l Acad. Sci.* 82:7952 (1985)). Using a technique known in the art, a transfer vector containing a Zcyto13 gene is transformed into *E. coli,* and screened for bacmids which contain an interrupted lacZ gene indicative of recombinant baculovirus. The bacmid DNA containing the recombinant baculovirus genome is then isolated using common techniques.

The illustrative PFASTBAC vector can be modified to a considerable degree. For example, the polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins (see, for example, Hill-Perkins and Possee, *J. Gen. Virol.* 71:971 (1990), Bonning, et al., *J. Gen. Virol.* 75:1551 (1994), and Chazenbalk and Rapoport, *J. Biol. Chem.* 270:1543 (1995). In such transfer vector constructs, a short or long version of the basic protein promoter can be used. Moreover, transfer vectors can be constructed, which replace the native Zcyto13 secretory signal sequences with secretory signal sequences derived from insect proteins. For example, a secretory signal sequence from Ecdysteroid Glucosyltransferase (EGT), honey bee Melittin (Invitrogen Corporation; Carlsbad, Calif.), or baculovirus gp67 (PharMingen: San Diego, Calif.) can be used in constructs to replace the native Zcyto13 secretory signal sequence.

The recombinant virus or bacmid is used to transfect host cells. Suitable insect host cells include cell lines derived from IPLB-Sf-21, a *Spodoptera frugiperda* pupal ovarian cell line, such as Sf9 (ATCC CRL 1711), Sf21AE, and Sf21 (Invitrogen Corporation; San Diego, Calif.), as well as Drosophila Schneider-2 cells, and the HIGH FIVEO cell line (Invitrogen) derived from *Trichoplusia ni* (U.S. Pat. No. 5,300,435). Commercially available serum-free media can be used to grow and to maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. When recombinant virus is used, the cells are typically grown up from an inoculation density of approximately $2-5 \times 10^5$ cells to a density of $1-2 \times 10^6$ cells at which time a recombinant viral stock is added at a multiplicity of infection (MOI) of 0.1 to 10, more typically near 3.

Established techniques for producing recombinant proteins in baculovirus systems are provided by Bailey et al., "Manipulation of Baculovirus Vectors," in *Methods in Molecular Biology, Volume 7: Gene Transfer and Expression Protocols,* Murray (ed.), pages 147–168 (The Humana Press, Inc. 1991), by Patel et al., "The baculovirus expression system," in *DNA Cloning 2: Expression Systems, 2nd Edition,* Glover et al. (eds.), pages 205–244 (Oxford University Press 1995), by Ausubel (1995) at pages 16–37 to 16–57, by Richardson (ed.), *Baculovirus Expression Protocols* (The Humana Press, Inc. 1995), and by Lucknow, "Insect Cell Expression Technology," in *Protein Engineering: Principles and Practice,* Cleland et al. (eds.), pages 183–218 (John Wiley & Sons, Inc. 1996).

Fungal cells, including yeast cells, can also be used to express the genes described herein. Yeast species of particular interest in this regard include *Saccharomyces cerevisiae, Pichia pastoris,* and *Pichia methanolica.* Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available. These vectors include YIp-based vectors, such as YIp5, YRp vectors, such as YRp17, YEp vectors such as YEp13 and YCp vectors, such as YCp19. Methods for transforming *S. cerevisiae* cells with exogenous DNA and producing recombinant polypeptides therefrom are disclosed by, for example, Kawasaki, U.S. Pat. No. 4,599,311, Kawasaki et al., U.S. Pat. No. 4,931,373, Brake, U.S. Pat. No. 4,870,008, Welch et al., U.S. Pat. No. 5,037,743, and Murray et al., U.S. Pat. No. 4,845,075. Transformed cells are selected by phenotype determined by the selectable marker, conmmonly drug resistance or the ability to grow in the absence of a particular nutrient (e.g., leucine). A suitable vector system for use in *Saccharomyces cerevisiae* is the POT1 vector system disclosed by Kawasaki et al. (U.S. Pat. No. 4,931,373), which allows transformed cells to be selected by growth in glucose-containing media. Additional suitable promoters and terminators for use in yeast include those from glycolytic enzyme genes (see, e.g., Kawasaki, U.S. Pat. No. 4,599,311, Kingsman et al., U.S. Pat. No. 4,615,974, and Bitter, U.S. Pat. No. 4,977,092) and alcohol dehydrogenase genes. See also U.S. Pat. Nos. 4,990,446, 5,063,154, 5,139,936, and 4,661,454.

Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al.,*J. Gen. Microbiol.* 132:3459 (1986), and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

For example, the use of Pichia methanolica as host for the production of recombinant proteins is disclosed by Raymond, U.S. Pat. No. 5,716,808, Raymond, U.S. Pat. No. 5,736,383, Raymond et al., Yeast 14:11-23 (1998), and in international publication Nos. WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica,* it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A suitable selectable marker for use in *Pichia methanolica* is a *P. methanolica* ADE2 gene, which encodes phosphoribosyl-5-aminoimidazole carboxylase (AIRC; EC 4.1.1.21), and which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. *P. methanolica* cells can be transformed by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Expression vectors can also be introduced into plant protoplasts, intact plant tissues, or isolated plant cells. Methods for introducing expression vectors into plant tissue include the direct infection or co-cultivation of plant tissue with *Agrobacterium tumefaciens,* microprojectile-mediated delivery, DNA injection, electroporation, and the like. See, for example, Horsch et al., *Science* 227:1229 (1985), Klein et al., *Biotechnology* 10:268 (1992), and Miki et al., "Procedures for Introducing Foreign DNA into Plants," in *Methods in Plant Molecular Biology and Biotechnology,* Glick et al. (eds.), pages 67–88 (CRC Press, 1993).

Alternatively, Zcyto13 genes can be expressed in prokaryotic host cells. Suitable promoters that can be used to express Zcyto13 polypeptides in a prokaryotic host are well-known to those of skill in the art and include promoters capable of recognizing the T4, T3, Sp6 and T7 polymerases, the $P_R$ and $P_L$ promoters of bacteriophage lambda, the trp, recA, heat shock, lacUV5, tac, lpp-lacSpr, phoA, and lacZ promoters of *E. coli,* promoters of *B. subtilis,* the promoters of the bacteriophages of Bacillus, Streptomyces promoters, the int promoter of bacteriophage lambda, the bla promoter of pBR322, and the CAT promoter of the chloramphenicol acetyl transferase gene. Prokaryotic promoters have been reviewed by Glick, *J. Ind. Microbiol.* 1:277 (1987), Watson et al., *Molecular Biology of the Gene,* 4th Ed. (Benjamin Cummins 1987), and by Ausubel et al. (1995).

Illustrative prokaryotic hosts include *E. coli* and *Bacillus subtilus.* Suitable strains of *E. coli* include BL21(DE3), BL21(DE3)pLysS, BL21(DE3)pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), *Molecular Biology Labfax* (Academic Press 1991)). Suitable strains of *Bacillus subtilus* include BR151, YB886, MI119, MI120, and B170 (see, for example, Hardy, "Bacillus Cloning Methods," in *DNA Cloning: A Practical Approach*, Glover (ed.) (IRL Press 1985)).

When expressing a Zcyto13 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Methods for expressing proteins in prokaryotic hosts are well-known to those of skill in the art (see, for example, Williams et al., "Expression of foreign proteins in *E. coli* using plasmid vectors and purification of specific polyclonal antibodies," in *DNA Cloning 2: Expression Systems, 2nd Edition*, Glover et al. (eds.), page 15 (Oxford University Press 1995), Ward et al., "Genetic Manipulation and Expression of Antibodies," in *Monoclonal Antibodies: Principles and Applications*, page 137 (Wiley-Liss, Inc. 1995), and Georgiou, "Expression of Proteins in Bacteria," in *Protein Engineering: Principles and Practice*, Cleland et al. (eds.), page 101 (John Wiley & Sons, Inc. 1996)).

Standard methods for introducing expression vectors into bacterial, yeast, insect, and plant cells are provided, for example, by Ausubel (1995).

General methods for expressing and recovering foreign protein produced by a mammalian cell system are provided by, for example, Etcheverry, "Expression of Engineered Proteins in Mammalian Cell Culture," in *Protein Engineering: Principles and Practice*, Cleland et al. (eds.), pages 163 (Wiley-Liss, Inc. 1996). Standard techniques for recovering protein produced by a bacterial system is provided by, for example, Grisshammner et al., "Purification of overproduced proteins from *E. coli* cells," in *DNA Cloning 2: Expression Systems, 2nd Edition*, Glover et al. (eds.), pages 59–92 (Oxford University Press 1995). Established methods for isolating recombinant proteins from a baculovirus system are described by Richardson (ed.), *Baculovirus Expression Protocols* (The Humana Press, Inc. 1995).

In particular, the art of producing interferon polypeptides from cultured cells is well-established due to the great interest in interferon pharmaceuticals. For example, recombinant interferons have been produced by bacteria, yeasts, plant cells, insect cells, vertebrate cells, as well as in cell-free systems (Horisberger and Di Marco, *Pharmac. Ther.* 66:507 (1995)). Reviews of methods for producing recombinant interferon are provided, for example, by Edge and Camble, *Biotechnol. Genet. Eng. Rev.* 2:215 (1984), Langer and Pestka, *J. Invest. Dermatol* 83:128s (1984), Pestka, *Semin. Hematol.* 23:27 (1986), Baron and Narula, *Crit. Rev. Biotechnol.* 10:179 (1990), and Croughan et al., *Bioprocess Technol* 21:377 (1995). The production of human interferon in Chinese hamster ovary (CHO) cells has been described by McCormick et al., U.S. Pat. No. 5,795,779, while Dorin et al., U.S. Pat. No. 5,814,485, teach methods for producing interferon in *E. coli*.

As an alternative, polypeptides of the present invention can be synthesized by exclusive solid phase synthesis, partial solid phase methods, fragment condensation or classical solution synthesis. These synthesis methods are well-known to those of skill in the art (see, for example, Merrifield, *J. Am. Chem. Soc.* 85:2149 (1963), Stewart et al., "Solid Phase Peptide Synthesis" (2nd Edition), (Pierce Chemical Co. 1984), Bayer and Rapp, *Chem. Pept. Prot.* 3:3 (1986), Atherton et al., *Solid Phase Peptide Synthesis: A Practical Approach* (RL Press 1989), Fields and Colowick, "Solid-Phase Peptide Synthesis," *Methods in Enzymology* Volume 289 (Academic Press 1997), and Lloyd-Williams et al., *Chemical Approaches to the Synthesis of Peptides and Proteins* (CRC Press, Inc. 1997)). Variations in total chemical synthesis strategies, such as "native chemical ligation" and "expressed protein ligation" are also standard (see, for example, Dawson et al., *Science* 266:776 (1994), Hackeng et al., *Proc. Nat'l Acad. Sci. USA* 94:7845 (1997), Dawson, *Methods Enzymol.* 287: 34 (1997), Muir et al, *Proc. Nat'l Acad. Sci. USA* 95:6705 (1998), and Severinov and Muir, *J. Biol. Chem.* 273:16205 (1998), and Kochendoerfer and Kent, *Curr. Opin Chem. Biol.* 3:665 (1999)).

7. Isolation of Zcyto13 Polypeptides

The polypeptides of the present invention can be purified to at least about 80% purity, to at least about 90% purity, to at least about 95% purity, or even greater than 95% purity with respect to contaminating macromolecules, particularly other proteins and nucleic acids, and free of infectious and pyrogenic agents. The polypeptides of the present invention may also be purified to a pharmaceutically pure state, which is greater than 99.9% pure. In certain preparations, a purified polypeptide is substantially free of other polypeptides, particularly other polypeptides of animal origin.

Fractionation and/or conventional purification methods can be used to obtain preparations of Zcyto13 purified from natural sources (e.g., heart, liver, brain, kidney, or spleen), and recombinant Zcyto13 polypeptides and fusion Zcyto13 polypeptides purified from recombinant host cells. In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. As an illustration, Beare et al., *Biochim. Biophys. Acta* 1310:81 (1996), describe the isolation of a murine interferon-α using a combination of Blue Sepharose chromatography, immunoaffinity exclusion, and Q Sepharose ion exchange fractionation.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Selection of a particular method for polypeptide isolation and purification is a matter of routine design and is determined in part by the properties of the chosen support. See, for example, *Affinity Chromatography: Principles & Methods* (Pharmacia LKB Biotechnology 1988), and Doonan, *Protein Purification Protocols* (The Humana Press 1996).

Additional variations in Zcyto13 isolation and purification can be devised by those of skill in the art. For example, anti-Zcyto13 antibodies, obtained as described below, can be used to isolate large quantities of protein by immunoaffinity purification. The use of monoclonal antibody columns to purify interferons from recombinant cells and from natural sources has been described, for example, by Staehelin et al., *J. Biol. Chem.* 256:9750 (1981), and by Adolf et al., *J. Biol. Chem.* 265:9290 (1990). Moreover, methods for binding ligands, such as Zcyto13, to receptor polypeptides bound to support media are well known in the art.

The polypeptides of the present invention can also be isolated by exploitation of particular properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1 (1985)). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (M. Deutscher, (ed.), *Meth. Enzymol.* 182:529 (1990)). For example, the interferon-γ isolation method of Rinderknecht et al., *J. Biol. Chem.* 259:6790 (1984), requires the binding of the interferon with concanavalin A-sepharose in one step. Within additional embodiments of the invention, a fusion of the polypeptide of interest and an affinity tag (e.g., maltose-binding protein, an immunoglobulin domain) may be constructed to facilitate purification.

Zcyto13 polypeptides or fragments thereof may also be prepared through chemical synthesis, as described below. Zcyto13 polypeptides may be monomers or multimers; glycosylated or non-glycosylated; PEGylated or non-PEGylated; and may or may not include an initial methionine amino acid residue.

8. Assays for Zcyto13, Its Analogs, and the Zcyto13 Receptor

As described above, the disclosed polypeptides can be used to construct Zcyto13 variants. A Zcyto13 variant may be functionally characterized by its ability to specifically bind with an anti-Zcyto13 antibody, or by a biological activity such as anti-viral activity, anti-proliferative activity, the ability to stimulate the expression of a gene known to be induced by murine interferon-α (e.g., a xanthine dehydrogenase gene of L929 fibroblastic cells, a 2'5'-oligoadenylate synthetase in quiescent BALB/c mouse 3T3 cells), or the ability to decrease the development of spontaneous diabetes and the passive transfer of diabetes in NOD mouse model of human IDDM. Illustrative activity assays are described below. A polypeptide produced by a Zcyto13 variant gene is considered to be a Zcyto13 agonist if the polypeptide exhibits a biological activity.

On the other hand, a Zcyto13 variant gene product that lacks biological activity may be a Zcyto13 antagonist. These biologically-inactive Zcyto13 variants can be initially identified on the basis of hybridization analysis, sequence identity determination, or by the ability to specifically bind anti-Zcyto13 antibody. A Zcyto13 antagonist can be further characterized by its ability to inhibit the biological response induced by Zcyto13 or by a Zcyto13 agonist. This inhibitory effect may result, for example, from the competitive or non-competitive binding of the antagonist to the Zcyto13 receptor.

Zcyto13, its agonists and antagonists are valuable in both in vivo and in vitro uses. As an illustration, cytokines can be used as components of defined cell culture media, alone or in combination with other cytokines and hormones, to replace serum that is commonly used in cell culture. In particular, interferons have been shown to stimulate the production of other biologically active polypeptides, such as interleukin-1, by cultured cells, which can be isolated from the culture (see, for example, Danis et al., *Clin. Exp. Immunol.* 80:435 (1990)). Interferons have also been shown to induce the expression of antigens by cultured cells (see, for example, Auth et al., *Hepatology* 18:546 (1993), Guadagni et al., *Int. J. Biol. Markers* 9:53 (1994), Girolomoni et al., *Eur. J. Immunol.* 25:2163 (1995), and Maciejewski et al., *Blood* 85:3183 (1995). This activity enhances the ability to identify new tumor associated antigens in vitro. Moreover, the ability of interferons to augment the level of expression of human tumor antigens indicates that interferons can be useful in an adjuvant setting for immunotherapy or immunoscintigraphy using anti-tumor antigen antibodies (Guadagni et al., *Cancer Immunol. Immunother.* 26:222 (1988); Guadagni et al., *Int. J. Biol. Markers* 9:53 (1994)).

Antagonists are also useful as research reagents for characterizing sites of interaction between Zcyto13 and its receptor. In a therapeutic setting, pharmaceutical compositions comprising Zcyto13 antagonists can be used to inhibit Zcyto13 activity.

One general class of Zcyto13 analogs are agonists or antagonists having an amino acid sequence that is a mutation of the amino acid sequences disclosed herein. Another general class of Zcyto13 analogs is provided by anti-idiotype antibodies, and fragments thereof, as described below. Moreover, recombinant antibodies comprising anti-idiotype variable domains can be used as analogs (see, for example, Monfardini et al., *Proc. Assoc. Am. Physicians* 108:420 (1996)). Since the variable domains of anti-idiotype Zcyto13 antibodies mimic Zcyto13, these domains can provide either Zcyto13 agonist or antagonist activity. As an illustration, Lim and Langer, *J. Interferon Res.* 13:295 (1993), describe anti-idiotypic interferon-α antibodies that have the properties of either interferon-α agonists or antagonists.

A third approach to identifying Zcyto13 analogs is provided by the use of combinatorial libraries. Methods for constructing and screening phage display and other combinatorial libraries are provided, for example, by Kay et al., *Phage Display of Peptides and Proteins* (Academic Press 1996), Verdine, U.S. Pat. No. 5,783,384, Kay, et. al., U.S. Pat. No. 5,747,334, and Kauffman et al., U.S. Pat. No. 5,723,323.

One assay that can be used to measure Zcyto13 biological activity is an interferon in vitro virus inhibition assay. For example, the anti-viral activity of variant Zcyto13 polypeptides can be assessed by a cytopathic effect reduction assay, in which mouse L929 cells are challenged with Mengo virus or vesicular stomatitis virus (Stewart, *The Interferon System* (Springer 1979); Zawatzky et al., *J. Gen. Virol.* 63:325 (1982); Van Heuvel et al., *J. Gen. Virol.* 67:2215 (1986)).

The anti-viral activity of a variant Zcyto13 can also be measured with murine cytomegalovirus-infected NIH 3T3 fibroblasts (Gribaudo et al., *Virology* 197:303 (1993)). Example 5 illustrates a method for testing anti-viral activity using encephalomyocarditis virus and murine L929 cells, as well as other methods for determining Zcyto13 activity.

Another approach to evaluating Zcyto13 activity is to use an assay that measures the inhibition of the proliferation of cultured murine cells. For example, the anti-proliferative activity of a variant Zcyto13 polypeptide can be determined with mouse B-16 melanoma cells (Fleischmann and Fleischmann, *J. Biol. Regul. Homeost. Agents* 2:173 (1988)).

In another approach, Zcyto13 activity is measured by the ability of the test polypeptide to stimulate the expression of a gene that is induced by murine interferon-α. Illustrative genes include a *xanthine dehydrogenase* gene of L929 fibroblastic cells, and a 2'5'-oligoadenylate synthetase in quiescent BALB/c mouse 3T3 cells (Falciani et al., *Biochem. J.* 285:1001 (1992); Yan et al., *Proc. Nat'l Acad. Sci USA* 86:2243 (1989)).

In yet another approach, the activity of a Zcyto13 variant is determined using an in vivo assay. For example, interferon-α administration decreases the development of spontaneous diabetes and the passive transfer of diabetes in NOD mouse model of human IDDM (Sobel and Ahvazi, *Diabetes* 47:1867 (1998)).

As a receptor ligand, the activity of Zcyto13 can be measured by a silicon-based biosensor microphysiometer, which measures the extracellular acidification rate or proton excretion associated with receptor binding and subsequent cellular responses. An exemplary device is the CYTOSENSOR Microphysiometer manufactured by Molecular Devices Corp. (Sunnyvale, Calif.). A variety of cellular responses, such as cell proliferation, ion transport, energy production, inflammatory response, regulatory and receptor activation, and the like, can be measured by this method (see, for example, McConnell et al., *Science* 257:1906 (1992), Pitchford et al., *Meth. Enzymol.* 228:84 (1997), Arimilli et al., *J. Immunol. Meth.* 212:49 (1998), and Van Liefde et al., *Eur. J. Pharmacol.* 346:87 (1998)). Moreover, the microphysiometer can be used for assaying adherent or non-adherent eukaryotic or prokaryotic cells.

Since energy metabolism is coupled with the use of cellular ATP, any event which alters cellular ATP levels, such as receptor activation and the initiation of signal transduction, will cause a change in cellular acid section. An early event in interferon signal transduction is protein phosphorylation, which requires ATP. By measuring extracellular acidification changes in cell media over time, therefore, the microphysiometer directly measures cellular responses to various stimuli, including Zcyto13, its agonists, or antagonists. A microphysiometer can be used to measure responses of a Zcyto13 responsive eukaryotic cell, compared to a control eukaryotic cell that does not respond to Zcyto13 polypeptide. Zcyto13 responsive eukaryotic cells comprise cells into which a receptor for Zcyto13 has been transfected to create a cell that is responsive to Zcyto13, or cells that are naturally responsive to Zcyto33. Examples of murine cells that respond to murine interferon-α members include embryonic stem cells, B-16 melanoma cells, $L_{929}$ fibroblastic cells, and 3T3 cells (see, for example, Fleischmann and Fleischmann, *J. Biol. Regul. Homeost. Agents* 2:173 (1988); Yan et al., *Proc. Nat'l Acad. Sci USA* 86:2243 (1989); Falciani et al., *Biochem. J.* 285:1001 (1992); Whyatt et al., *Mol. Cell Biol.* 13:7971 (1993)). Zcyto13 modulated cellular responses are measured by a change (e.g., an increase or decrease in extracellular acidification) in the response of cells exposed to Zcyto13, compared with control cells that have not been exposed to Zcyto13.

Accordingly, a microphysiometer can be used to identify cells, tissues, or cell lines which respond to a Zcyto13 stimulated pathway, and which express a functional Zcyto13 receptor. As an illustration, cells that express a functional Zcyto13 receptor can be identified by (a) providing test cells, (b) incubating a first portion of the test cells in the absence of Zcyto13, (c) incubating a second portion of the test cells in the presence of Zcyto13, and (d) detecting a change (e.g., an increase or decrease in extracellular acidification rate, as measured by a microphysiometer) in a cellular response of the second portion of the test cells, as compared to the first portion of the test cells, wherein such a change in cellular response indicates that the test cells express a functional Zcyto13 receptor. An additional negative control may be included in which a portion of the test cells is incubated with Zcyto13 and an anti-Zcyto13 antibody to inhibit the binding of Zcyto13 with its cognate receptor.

The microphysiometer also provides one means to identify Zcyto13 agonists. For example, agonists of Zcyto13 can be identified by a method, comprising the steps of (a) providing cells responsive to Zcyto13, (b) incubating a first portion of the cells in the absence of a test compound, (c) incubating a second portion of the cells in the presence of a test compound, and (d) detecting a change, for example, an increase or diminution, in a cellular response of the second portion of the cells as compared to the first portion of the cells, wherein such a change in cellular response indicates that the test compound is a Zcyto13 agonist. An illustrative change in cellular response is a measurable change in extracellular acidification rate, as measured by a microphysiometer. Moreover, incubating a third portion of the cells in the presence of Zcyto13 and in the absence of a test compound can be used as a positive control for the Zcyto13 responsive cells, and as a control to compare the agonist activity of a test compound with that of Zcyto13. An additional control may be included in which a portion of the cells is incubated with a test compound (or Zcyto13) and an anti-Zcyto13 antibody to inhibit the binding of the test compound (or Zcyto13) with the Zcyto13 receptor.

The microphysiometer also provides a means to identify Zcyto13 antagonists. For example, Zcyto13 antagonists can be identified by a method, comprising the steps of (a) providing cells responsive to Zcyto13, (b) incubating a first portion of the cells in the presence of Zcyto13 and in the absence of a test compound, (c) incubating a second portion of the cells in the presence of both Zcyto13 and the test compound, and (d) comparing the cellular responses of the first and second cell portions, wherein a decreased response by the second portion, compared with the response of the first portion, indicates that the test compound is a Zcyto13 antagonist. An illustrative change in cellular response is a measurable change extracellular acidification rate, as measured by a microphysiometer.

Zcyto13, its analogs, and anti-iodiotype Zcyto13 antibodies can be used to identify and to isolate Zcyto13 receptors. For example, proteins and peptides of the present invention can be immobilized on a column and used to bind receptor proteins from membrane preparations that are run over the column (Hermanson et al. (eds.), *Immobilized Affinity Ligand Techniques,* pages 195–202 (Academic Press 1992)). Radiolabeled or affinity labeled Zcyto13 polypeptides can also be used to identify or to localize Zcyto13 receptors in a biological sample (see, for example, Deutscher (ed.), *Methods in Enzymol., vol.* 182, pages 721–37 (Academic Press 1990); Brunner et al., *Ann. Rev. Biochem.* 62:483

(1993); Fedan et al., *Biochem. Pharmacol.* 33:1167 (1984)). Also see, Varthakavi and Minocha, *J. Gen. Virol.* 77:1875 (1996), who describe the use of anti-idiotype antibodies for receptor identification.

9. Production of Antibodies to Zcyto13 Proteins

Antibodies to Zcyto13 can be obtained, for example, using the product of a Zcyto13 expression vector or Zcyto13 isolated from a natural source as an antigen. Particularly useful anti-Zcyto13 antibodies "bind specifically" with Zcyto13. Antibodies are considered to be specifically binding if the antibodies exhibit at least one of the following two properties: (1) antibodies bind to Zcyto13 with a threshold level of binding activity, and (2) antibodies do not significantly cross-react with polypeptides related to Zcyto13.

With regard to the first characteristic, antibodies specifically bind if they bind to a Zcyto13 polypeptide, peptide or epitope with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, *Ann. NY Acad. Sci.* 51:660 (1949)). With regard to the second characteristic, antibodies do not significantly cross-react with related polypeptide molecules, for example, if they detect Zcyto13, but not known polypeptides using a standard Western blot analysis. Examples of known related polypeptides are orthologs and proteins from the same species that are members of a protein family. For example, specifically-binding anti-Zcyto13 antibodies bind with Zcyto13, but not with polypeptides such as other interferon-α polypeptides, interferon-β, interferon-γ, interferon-δ, interferon-ω, or interferon-τ. Suitable antibodies include antibodies that bind with Zcyto13 in regions having a low sequence similarity with other interferons.

Anti-Zcyto13 antibodies can be produced using antigenic Zcyto13 epitope-bearing peptides and polypeptides. Antigenic epitope-bearing peptides and polypeptides of the present invention contain a sequence of at least nine, or between 15 to about 30 amino acids contained within SEQ ID NO:2. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that bind with Zcyto13. It is desirable that the amino acid sequence of the epitope-bearing peptide is selected to provide substantial solubility in aqueous solvents (i.e., the sequence includes relatively hydrophilic residues, while hydrophobic residues are preferably avoided). Moreover, amino acid sequences containing proline residues may be also be desirable for antibody production.

As an illustration, potential antigenic sites in Zcyto13 were identified using the Jameson-Wolf method, Jameson and Wolf, *CABIOS* 4:181, (1988), as implemented by the PROTEAN program (version 3.14) of LASERGENE (DNASTAR; Madison, Wis.). Default parameters were used in this analysis.

The Jameson-Wolf method predicts potential antigenic determinants by combining six major subroutines for protein structural prediction. Briefly, the Hopp-Woods method, Hopp et al., *Proc. Nat'l Acad. Sci. USA* 78:3824 (1981), was first used to identify amino acid sequences representing areas of greatest local hydrophilicity (parameter: seven residues averaged). In the second step, Emini's method, Emini et al., *J. Virology* 55:836 (1985), was used to calculate surface probabilities (parameter: surface decision threshold (0.6)=1). Third, the Karplus-Schultz method, Karplus and Schultz, *Naturwissenschaften* 72:212 (1985), was used to predict backbone chain flexibility (parameter: flexibility threshold (0.2)=1). In the fourth and fifth steps of the analysis, secondary structure predictions were applied to the data using the methods of Chou-Fasman, Chou, "Prediction of Protein Structural Classes from Amino Acid Composition," in *Prediction of Protein Structure and the Principles of Protein Conformation,* Fasman (ed.), pages 549–586 (Plenum Press 1990), and Garnier-Robson, Garnier et al., *J. Mol. Biol.* 120:97 (1978) (Chou-Fasman parameters: conformation table=64 proteins; α region threshold=103; β region threshold=105; Garnier-Robson parameters: α and β decision constants=0). In the sixth subroutine, flexibility parameters and hydropathy/solvent accessibility factors were combined to determine a surface contour value, designated as the "antigenic index." Finally, a peak broadening function was applied to the antigenic index, which broadens major surface peaks by adding 20, 40, 60, or 80% of the respective peak value to account for additional free energy derived from the mobility of surface regions relative to interior regions. This calculation was not applied, however, to any major peak that resides in a helical region, since helical regions tend to be less flexible.

The results of this analysis indicated that the following amino acid sequences of SEQ ID NO:2 would provide suitable antigenic peptides: amino acids 51 to 61 ("antigenic peptide 1"), amino acids 68 to 73 ("antigenic peptide 2"), amino acids 90 to 96 ("antigenic peptide 3"), amino acids 97 to 136 ("antigenic peptide 4"), amino acids 104 to 110 ("antigenic peptide 5"), amino acids 120 to 136 ("antigenic peptide 6"), amino acids 156 to 161 ("antigenic peptide 7"), amino acids 179 to 185 ("antigenic peptide 8"), and amino acids 190 to 199 ("antigenic peptide 9"). The present invention contemplates the use of any one of antigenic peptides 1 to 9 to generate antibodies to Zcyto13. The present invention also contemplates polypeptides comprising at least one of antigenic peptides 1 to 9.

Polyclonal antibodies to recombinant Zcyto13 protein or to Zcyto13 isolated from natural sources can be prepared using methods well-known to those of skill in the art. See, for example, Green et al., "Production of Polyclonal Antisera," in *Immunochemical Protocols* (Manson, ed.), pages 1–5 (Humana Press 1992), and Williams et al., "Expression of foreign proteins in *E. coli* using plasmid vectors and purification of specific polyclonal antibodies," in *DNA Cloning 2: Expression Systems, 2nd Edition,* Glover et al. (eds.), page 15 (Oxford University Press 1995). The immunogenicity of a Zcyto13 polypeptide can be increased through the use of an adjuvant, such as alum (aluminum hydroxide) or Freund's complete or incomplete adjuvant. Polypeptides useful for immunization also include fusion polypeptides, such as fusions of Zcyto13 or a portion thereof with an immunoglobulin polypeptide or with maltose binding protein. The polypeptide immunogen may be a full-length molecule or a portion thereof. If the polypeptide portion is "hapten-like," such portion may be advantageously joined or linked to a macromolecular carrier (such as keyhole limpet hemocyanin (KLH), bovine serum albumin (BSA) or tetanus toxoid) for immnunization.

Although polyclonal antibodies are typically raised in animals such as horses, cows, dogs, chicken, rats, mice, rabbits, guinea pigs, goats, or sheep, an anti-Zcyto13 antibody of the present invention may also be derived from a subhuman primate antibody. General techniques for raising diagnostically and therapeutically useful antibodies in baboons may be found, for example, in Goldenberg et al., international patent publication No. WO 91/11465, and in Losman et al., *Int. J. Cancer* 46:310 (1990).

Alternatively, monoclonal anti-Zcyto13 antibodies can be generated. Rodent monoclonal antibodies to specific antigens may be obtained by methods known to those skilled in the art (see, for example, Kohler et al., *Nature* 256:495 (1975), Coligan et al. (eds.), *Current Protocols in Immunology*, Vol. 1, pages 2.5.1–2.6.7 (John Wiley & Sons 1991) ["Coligan"], Picksley et al., "Production of monoclonal antibodies against proteins expressed in *E. coli*," in *DNA Cloning 2: Expression Systems, 2nd Edition*, Glover et al. (eds.), page 93 (Oxford University Press 1995)).

Briefly, monoclonal antibodies can be obtained by injecting mice with a composition comprising a Zcyto13 gene product, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

In addition, an anti-Zcyto13 antibody of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13 (1994), Lonberg et al., *Nature* 368:856 (1994), and Taylor et al., *Int. Immun.* 6:579 (1994).

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1–2.7.12 and pages 2.9.1–2.9.3; Baines et al., "Purification of Immunoglobulin G (IgG)," in *Methods in Molecular Biology*, Vol. 10, pages 79–104 (The Humana Press, Inc. 1992)).

For particular uses, it may be desirable to prepare fragments of anti-Zcyto13 antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230 (1960), Porter, *Biochem. J.* 73:119 (1959), Edelman et al., in *Methods in Enzymology* Vol. 1, page 422 (Academic Press 1967), and by Coligan at pages 2.8.1–2.8.10 and 2.10.–2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., *Proc. Nat'l Acad. Sci. USA* 69:2659 (1972). Alternatively, the variable chains can be linked by an intermolecular disulfide bond or cross-linked by chemicals such as glutaraldehyde (see, for example, Sandhu, *Crit. Rev. Biotech.* 12:437 (1992)).

The Fv fragments may comprise $V_H$ and $V_L$ chains, which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing scFvs are described, for example, by Whitlow et al., *Methods: A Companion to Methods in Enzymology* 2:97 (1991) (also see, Bird et al., *Science* 242:423 (1988), Ladner et al., U.S. Pat. No. 4,946,778, Pack et al., *Bio/Technology* 11:1271 (1993), and Sandhu, supra).

As an illustration, an scFV can be obtained by exposing lymphocytes to Zcyto13 polypeptide in vitro, and selecting antibody display libraries in phage or similar vectors (for instance, through use of immobilized or labeled Zcyto13 protein or peptide). Genes encoding polypeptides having potential Zcyto13 polypeptide binding domains can be obtained by screening random peptide libraries displayed on phage (phage display) or on bacteria, such as E. coli. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., *Phage Display of Peptides and Proteins* (Academic Press, Inc. 1996)) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the Zcyto13 sequences disclosed herein to identify proteins which bind to Zcyto13.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106 (1991), Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995), and Ward et al., "Genetic Manipulation and Expression of Antibodies," in *Monoclonal Antibodies: Principles and Applications*, Birch et al., (eds.), page 137 (Wiley-Liss, Inc. 1995)).

Alternatively, an anti-Zcyto13 antibody may be derived from a "humanized" monoclonal antibody. Humanized monoclonal antibodies are produced by transferring mouse complementary determining regions from heavy and light variable chains of the mouse immunoglobulin into a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833 (1989). Techniques for producing humanized monoclonal antibodies are described, for example, by Jones et al., *Nature* 321:522 (1986), Carter et al., *Proc. Nat'l Acad. Sci. USA* 89:4285 (1992), Sandhu, *Crit. Rev. Biotech.* 12:437 (1992), Singer et al., *J. Immun.* 150:2844 (1993), Sudhir (ed.), *Antibody Engineering Protocols* (Humana Press, Inc. 1995), Kelley, "Engineering Therapeutic Antibodies," in *Protein Engineering: Principles and Practice,* Cleland et al. (eds.), pages 399–434 (John Wiley & Sons, Inc. 1996), and by Queen et al., U.S. Pat. No. 5,693,762 (1997).

Polyclonal anti-idiotype antibodies can be prepared by immunizing animals with anti-Zcyto13 antibodies or antibody fragments, using standard techniques. See, for example, Green et al., "Production of Polyclonal Antisera," in *Methods In Molecular Biology: Immunochemical Protocols,* Manson (ed.), pages 1–12 (Humana Press 1992). Also, see Coligan at pages 2.4.1–2.4.7. Alternatively, monoclonal anti-idiotype antibodies can be prepared using anti-Zcyto13 antibodies or antibody fragments as immunogens with the techniques, described above. As another alternative, humanized anti-idiotype antibodies or subhuman primate anti-idiotype antibodies can be prepared using the above-described techniques. Methods for producing anti-idiotype antibodies are described, for example, by Irie, U.S. Pat. No. 5,208,146, Greene, et. al., U.S. Pat. No. 5,637,677, and Varthakavi and Minocha, *J. Gen. Virol.* 77:1875 (1996).

10. Use of Zcyto13 Nucleotide Sequences to Detect Zcyto13 Gene Expression and to Examine Zcyto13 Gene Structure Nucleic acid molecules can be used to detect the expression of a Zcyto13 gene in a biological sample. Suitable probe molecules include double-stranded nucleic acid molecules comprising the nucleotide sequence of SEQ ID NO:1, or a portion thereof, as well as single-stranded nucleic acid molecules having the complement of the nucleotide sequence of SEQ ID NO:1, or a portion thereof. Probe molecules may be DNA, RNA, oligonucleotides, and the like. As used herein, the term "portion" refers to at least eight nucleotides to at least 20 or more nucleotides. Certain probes bind with regions of the Zcyto13 gene that have a low sequence similarity to comparable regions in other interferons.

In a basic assay, a single-stranded probe molecule is incubated with RNA, isolated from a biological sample, under conditions of temperature and ionic strength that promote base pairing between the probe and target Zcyto13 RNA species. After separating unbound probe from hybridized molecules, the amount of hybrids is detected.

Well-established hybridization methods of RNA detection include northern analysis and dot/slot blot hybridization (see, for example, Ausubel (1995) at pages 4–1 to 4–27, and Wu et al. (eds.), "Analysis of Gene Expression at the RNA Level," in *Methods in Gene Biotechnology,* pages 225–239 (CRC Press, Inc. 1997)). Nucleic acid probes can be detectably labeled with radioisotopes such as $^{32}P$ or $^{35}S$.

Alternatively, Zcyto13 RNA can be detected with a nonradioactive hybridization method (see, for example, Isaac (ed.), *Protocols for Nucleic Acid Analysis by Nonradioactive Probes* (Humana Press, Inc. 1993)). Typically, nonradioactive detection is achieved by enzymatic conversion of chromogenic or chemiluminescent substrates. Illustrative nonradioactive moieties include biotin, fluorescein, and digoxigenin.

Zcyto13 oligonucleotide probes are also useful for in vivo diagnosis. As an illustration, $^{18}BF$-abeled oligonucleotides can be administered to a subject and visualized by positron emission tomography (Tavitian et al., *Nature Medicine* 4:467 (1998)).

Numerous diagnostic procedures take advantage of the polymerase chain reaction (PCR) to increase sensitivity of detection methods. Standard techniques for performing PCR are well-known (see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)).

PCR primers can be designed to amplify a portion of the Zcyto13 gene that has a low sequence similarity to a comparable region in other interferons.

One variation of PCR for diagnostic assays is reverse transcriptase-PCR (RT-PCR). In the RT-PCR technique, RNA is isolated from a biological sample, reverse transcribed to cDNA, and the cDNA is incubated with Zcyto13 primers (see, for example, Wu et al. (eds.), "Rapid Isolation of Specific cDNAs or Genes by PCR," in *Methods in Gene Biotechnology,* pages 15–28 (CRC Press, Inc. 1997)). PCR is then performed and the products are analyzed using standard techniques.

As an illustration, RNA is isolated from biological sample using, for example, the gunadinium-thiocyanate cell lysis procedure described above. Alternatively, a solid-phase technique can be used to isolate mRNA from a cell lysate. A reverse transcription reaction can be primed with the isolated RNA using random oligonucleotides, short homopolymers of dT, or Zcyto13 anti-sense oligomers. Oligo-dT primers offer the advantage that various mRNA nucleotide sequences are amplified that can provide control target sequences. Zcyto13 sequences are amplified by the polymerase chain reaction using two flanking oligonucleotide primers that are typically 20 bases in length.

PCR amplification products can be detected using a variety of approaches. For example, PCR products can be fractionated by gel electrophoresis, and visualized by ethidium bromide staining. Alternatively, fractionated PCR products can be transferred to a membrane, hybridized with a detectably-labeled Zcyto13 probe, and examined by autoradiography. Additional alternative approaches include the use of digoxigenin-labeled deoxyribonucleic acid triphosphates to provide chemiluminescence detection, and the C-TRAK colorimetric assay.

Another approach for detection of Zcyto13 expression is cycling probe technology (CPT), in which a single-stranded DNA target binds with an excess of DNA-RNA-DNA chimeric probe to form a complex, the RNA portion is cleaved with RNAase H, and the presence of cleaved chimeric probe is detected (see, for example, Beggs et al., *J. Clin. Microbiol.* 34:2985 (1996), Bekkaoui et al., *Biotechniques* 20:240 (1996)). Alternative methods for detection of Zcyto13 sequences can utilize approaches such as nucleic acid sequence-based amplification (NASBA), cooperative amplification of templates by cross-hybridization (CATCH), and the ligase chain reaction (LCR) (see, for example, Marshall et al., U.S. Pat. No. 5,686,272 (1997), Dyer et al., *J. Virol. Methods* 60:161 (1996), Ehricht et al., *Eur. J. Biochem.* 243:358 (1997), and Chadwick et al., *J. Virol. Methods* 70:59 (1998)). Other standard methods are known to those of skill in the art.

Zcyto13 probes and primers can also be used to detect and to localize Zcyto13 gene expression in tissue samples. Methods for such in situ hybridization are well-known to those of skill in the art (see, for example, Choo (ed.), *In Situ Hybridization Protocols* (Humana Press, Inc. 1994), Wu et al. (eds.), "Analysis of Cellular DNA or Abundance of mRNA by Radioactive In Situ Hybridization (RISH)," in *Methods in Gene Biotechnology*, pages 259–278 (CRC Press, Inc. 1997), and Wu et al. (eds.), "Localization of DNA or Abundance of mRNA by Fluorescence In Situ Hybridization (RISH)," in *Methods in Gene Biotechnology*, pages 279–289 (CRC Press, Inc. 1997)). Various additional diagnostic approaches are well-known to those of skill in the art (see, for example, Mathew (ed.), *Protocols in Human Molecular Genetics* (Humana Press, Inc. 1991), Coleman and Tsongalis, *Molecular Diagnostics* (Humana Press, Inc. 1996), and Elles, *Molecular Diagnosis of Genetic Diseases* (Humana Press, Inc., 1996)).

Nucleic acid molecules comprising Zcyto13 nucleotide sequences can also be used to determine whether a subject's chromosomes contain a mutation in the Zcyto13 gene. Detectable chromosomal aberrations at the Zcyto13 gene locus include, but are not limited to, aneuploidy, gene copy number changes, insertions, deletions, restriction site changes and rearrangements. Of particular interest are genetic alterations that inactivate the Zcyto13 gene.

Aberrations associated with the Zcyto13 locus can be detected using nucleic acid molecules of the present invention by employing molecular genetic techniques, such as restriction fragment length polymorphism analysis, short tandem repeat analysis employing PCR techniques, amplification-refractory mutation system analysis, single-strand conformation polymorphism detection, RNase cleavage methods, denaturing gradient gel electrophoresis, fluorescence-assisted mismatch analysis, and other genetic analysis techniques known in the art (see, for example, Mathew (ed.), *Protocols in Human Molecular Genetics* (Humana Press, Inc. 1991), Marian, *Chest* 108:255 (1995), Coleman and Tsongalis, *Molecular Diagnostics* (Human Press, Inc. 1996), Elles (ed.) *Molecular Diagnosis of Genetic Diseases* (Humana Press, Inc. 1996), Landegren (ed.), *Laboratory Protocols for Mutation Detection* (Oxford University Press 1996), Birren et al. (eds.), *Genome Analysis, Vol. 2: Detecting Genes* (Cold Spring Harbor Laboratory Press 1998), Dracopoli et al. (eds.), *Current Protocols in Human Genetics* (John Wiley & Sons 1998), and Richards and Ward, "Molecular Diagnostic Testing," in *Principles of Molecular Medicine*, pages 83–88 (Humana Press, Inc. 1998)).

The protein truncation test is also useful for detecting the inactivation of a gene in which translation-terminating mutations produce only portions of the encoded protein (see, for example, Stoppa-Lyonnet et al., *Blood* 91:3920 (1998)). According to this approach, RNA is isolated from a biological sample, and used to synthesize cDNA. PCR is then used to amplify the Zcyto13 target sequence and to introduce an RNA polymerase promoter, a translation initiation sequence, and an in-frame ATG triplet. PCR products are transcribed using an RNA polymerase, and the transcripts are translated in vitro with a T7-coupled reticulocyte lysate system. The translation products are then fractionated by SDS-PAGE to determine the lengths of the translation products. The protein truncation test is described, for example, by Dracopoli et al. (eds.), *Current Protocols in Human Genetics*, pages 9.11.1–9.11.18 (John Wiley & Sons 1998).

The present invention also contemplates kits for performing a diagnostic assay for Zcyto13 gene expression or to detect mutations in the Zcyto13 gene. Such kits comprise nucleic acid probes, such as double-stranded nucleic acid molecules comprising the nucleotide sequence of SEQ ID NO:1, or a portion thereof, as well as single-stranded nucleic acid molecules having the complement of the nucleotide sequence of SEQ ID NO:1, or a portion thereof. Probe molecules may be DNA, RNA, oligonucleotides, and the like. Kits may comprise nucleic acid primers for performing PCR.

Such a kit can contain all the necessary elements to perform a nucleic acid diagnostic assay described above. A kit will comprise at least one container comprising a Zcyto13 probe or primer. The kit may also comprise a second container comprising one or more reagents capable of indicating the presence of Zcyto13 sequences. Examples of such indicator reagents include detectable labels such as radioactive labels, fluorochromes, chemiluminescent agents, and the like. A kit may also comprise a means for conveying to the user that the Zcyto13 probes and primers are used to detect Zcyto13 gene expression. For example, written instructions may state that the enclosed nucleic acid molecules can be used to detect either a nucleic acid molecule that encodes Zcyto13, or a nucleic acid molecule having a nucleotide sequence that is complementary to a Zcyto13-encoding nucleotide sequence. The written material can be applied directly to a container, or the written material can be provided in the form of a packaging insert.

11. Use of Anti-Zcyto13 Antibodies to Detect Zcyto13 Protein

The present invention contemplates the use of anti-Zcyto13 antibodies to screen biological samples in vitro for the presence of Zcyto13. In one type of in vitro assay, anti-Zcyto13 antibodies are used in liquid phase. For example, the presence of Zcyto13 in a biological sample can be tested by mixing the biological sample with a trace amount of labeled Zcyto13 and an anti-Zcyto13 antibody under conditions that promote binding between Zcyto13 and its antibody. Complexes of Zcyto13 and anti-Zcyto13 in the sample can be separated from the reaction mixture by contacting the complex with an immobilized protein which binds with the antibody, such as an Fc antibody or Staphylococcus protein A. The concentration of Zcyto13 in the biological sample will be inversely proportional to the amount of labeled Zcyto13 bound to the antibody and directly related to the amount of free labeled Zcyto13.

Alternatively, in vitro assays can be performed in which anti-Zcyto13 antibody is bound to a solid-phase carrier. For example, antibody can be attached to a polymer, such as amninodextran, in order to link the antibody to an insoluble support such as a polymer-coated bead, a plate or a tube. Other suitable in vitro assays will be readily apparent to those of skill in the art.

In another approach, anti-Zcyto13 antibodies can be used to detect Zcyto13 in tissue sections prepared from a biopsy specimen. Such immunochemical detection can be used to determine the relative abundance of Zcyto13 and to determine the distribution of Zcyto13 in the examined tissue. General immunochemistry techniques are well established (see, for example, Ponder, "Cell Marking Techniques and Their Application," in *Mammalian Development: A Practical Approach,* Monk (ed.), pages 115–38 (IRL Press 1987), Coligan at pages 5.8.1–5.8.8, Ausubel (1995) at pages 14.6.1 to 14.6.13 (Wiley Interscience 1990), and Manson (ed.), *Methods In Molecular Biology, Vol.* 10: *Immunochemical Protocols* (The Humana Press, Inc. 1992)).

Immunochemical detection can be performed by contacting a biological sample with an anti-Zcyto13 antibody, and then contacting the biological sample with a detectably labeled molecule which binds to the antibody. For example, the detectably labeled molecule can comprise an antibody moiety that binds to anti-Zcyto13 antibody. Alternatively, the anti-Zcyto13 antibody can be conjugated with avidin/streptavidin (or biotin) and the detectably labeled molecule can comprise biotin (or avidin/streptavidin). Numerous variations of this basic technique are well-known to those of skill in the art.

Alternatively, an anti-Zcyto13 antibody can be conjugated with a detectable label to form an anti-Zcyto13 immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^3H$, $^{125}I$, $^{131}I$, $^{135}S$ and $^{14}C$.

Anti-Zcyto13 immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, anti-Zcyto13 immunoconjugates can be detectably labeled by coupling an antibody component to a chemiluminescent compound. The presence of the chemilurninescent-tagged imnuunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-Zcyto13 immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-Zcyto13 immunoconjugates can be detectably labeled by linking an anti-Zcyto13 antibody component to an enzyme. When the anti-Zcyto13-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the present invention. The binding of marker moieties to anti-Zcyto13 antibodies can be accomplished using standard techniques known to the art. Typical methodology in this regard is described by Kennedy et al., *Clin. Chim. Acta* 70:1 (1976), Schurs et al., *Clin. Chim. Acta* 81:1 (1977), Shih et al., *Int'l J. Cancer* 46:1101 (1990), Stein et al., *Cancer Res.* 50:1330 (1990), and Coligan, supra, Moreover, the convenience and versatility of immunochemical detection can be enhanced by using anti-Zcyto13 antibodies that have been conjugated with avidin, streptavidin, and biotin (see, for example, Wilchek et al. (eds.), "Avidin-Biotin Technology," *Methods In Enzymology, Vol.* 184 (Academic Press 1990), and Bayer et al., "Immunochemical Applications of Avidin-Biotin Technology," in *Methods In Molecular Biology, Vol.* 10, Manson (ed.), pages 149–162 (The Humana Press, Inc. 1992).

Methods for performing immunoassays are well-established. See, for example, Cook and Self, "Monoclonal Antibodies in Diagnostic Immunoassays," in *Monoclonal Antibodies: Production, Engineering, and Clinical Application,* Ritter and Ladyman (eds.), pages 180–208, (Cambridge University Press, 1995), Perry, "The Role of Monoclonal Antibodies in the Advancement of Immunoassay Technology," in *Monoclonal Antibodies: Principles and Applications,* Birch and Lennox (eds.), pages 107–120 (Wiley-Liss, Inc. 1995), and Diamandis, *Immunoassay* (Academic Press, Inc. 1996).

In a related approach, biotin- or FITC-labeled Zcyto13 can be used to identify cells that bind Zcyto13. Such can binding can be detected, for example, using flow cytometry.

The present invention also contemplates kits for performing an immunological diagnostic assay for Zcyto13 gene expression. Such kits comprise at least one container comprising an anti-Zcyto13 antibody, or antibody fragment. A kit may also comprise a second container comprising one or more reagents capable of indicating the presence of Zcyto13 antibody or antibody fragments. Examples of such indicator reagents include detectable labels such as a radioactive label, a fluorescent label, a chemiluminescent label, an enzyme label, a bioluminescent label, colloidal gold, and the like. A kit may also comprise a means for conveying to the user that Zcyto13 antibodies or antibody fragments are used to detect Zcyto13 protein. For example, written instructions may state that the enclosed antibody or antibody fragment can be used to detect Zcyto13. The written material can be applied directly to a container, or. the written material can be provided in the form of a packaging insert.

12. Therapeutic Uses of Polypeptides Having Zcyto13 Activity

Interferons are known to be potent cytokines that possess antiviral, immunomodulating, and anti-proliferative activities. Therefore, the present invention includes the use of proteins, polypeptides, and peptides having Zcyto13 activity (such as Zcyto13 polypeptides, Zcyto13 analogs, and Zcyto13 fusion proteins) to provide antiviral, immunomodulatory, or anti-proliferative activity. The present invention contemplates the use of these molecules for either veterinary or for human therapeutic uses.

Both recombinant interferons and interferons isolated from natural sources have been approved in the United States for treatment of autoimmune diseases, renal cell carcinoma, basal cell carcinoma, malignant melanoma, condylomata acuminata, chronic hepatitis B, hepatitis C, chronic hepatitis D, chronic non-A, non-B/C hepatitis, bladder carcinoma, multiple myeloma, chronic myelogenous leukemia, non-Hodgkin's lymphoma, cervical carcinoma, laryngeal papilloma, fungoides mycosis, Kaposi's sarcoma in patients infected with human immunodeficiency virus, hairy cell leukemia, and multiple sclerosis. In addition, Zcyto13 may be used to treat forms of arteriosclerosis, such as atherosclerosis, by inhibiting cell proliferation, or to treat retinopathy. Accordingly, the present invention contemplates the use of proteins, polypeptides, and peptides having Zcyto13 activity to treat such conditions.

In addition, interferons are known to augment the level of expression of human tumor antigens, as discussed above. Thus, the present invention includes the use of proteins, polypeptides and peptides having Zcyto13 activity as an adjuvant for immunotherapy or immunoscintigraphy using anti-tumor antigen antibodies.

Generally, the dosage of administered Zcyto13 (or Zcyto13 analog or fusion protein) will vary depending upon such factors as the subject's age, weight, height, sex, general medical condition and previous medical history. Typically, it is desirable to provide the recipient with a dosage of Zcyto13, which is in the range of from about 1 pg/kg to 10 mg/kg (amount of agent/body weight of subject), although a lower or higher dosage also may be administered as circumstances dictate.

Administration of a molecule having Zcyto13 activity to a subject can be intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses.

Additional routes of administration include oral, mucosal-membrane, pulmonary, and transcutaneous. Oral delivery is suitable for polyester microspheres, zein microspheres, proteinoid microspheres, polycyanoacrylate microspheres, and lipid-based systems (see, for example, DiBase and Morrel, "Oral Delivery of Microencapsulated Proteins," in *Protein Delivery: Physical Systems,* Sanders and Hendren (eds.), pages 255–288 (Plenum Press 1997)). The feasibility of an intranasal delivery is exemplified by such a mode of insulin administration (see, for example, Hinchcliffe and Illum, *Adv. Drug Deliv. Rev.* 35:199 (1999)). Dry or liquid particles comprising Zcyto13 can be prepared and inhaled with the aid of dry-powder dispersers, liquid aerosol generators, or nebulizers (e.g., Pettit and Gombotz, *TIBTECH* 16:343 (1998); Patton et al., *Adv. Drug Deliv. Rev.* 35:235 (1999)). This approach is illustrated by the AERX diabetes management system, which is a hand-held electronic inhaler that delivers aerosolized insulin into the lungs. Studies have shown that proteins as large as 48,000 kDa have been delivered across skin at therapeutic concentrations with the aid of low-frequency ultrasound, which illustrates the feasibility of trascutaneous administration (Mitragotri et al., *Science* 269:850 (1995)). Transdermal delivery using electroporation provides another means to administer a molecule having Zcyto13 activity (Potts et al., *Pharm. Biotechnol.* 10:213 (1997)).

A pharmaceutical composition comprising a protein, polypeptide, or peptide having Zcyto13 activity can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient subject. Sterile phosphate-buffered saline is one example of a pharmaceutically acceptable carrier. Other suitable carriers are well-known to those in the art. See, for example, Gennaro (ed.), *Remington's Pharmaceutical Sciences,* 19th Edition (Mack Publishing Company 1995).

For purposes of therapy, molecules having Zcyto13 activity and a pharmaceutically acceptable carrier are administered to a subject in a therapeutically effective amount. A combination of a protein, polypeptide, or peptide having Zcyto13 activity and a pharmaceutically acceptable carrier is said to be administered in a "therapeutically effective amount" if the amount administered is physiologically significant. An agent is physiologically significant if its presence results in a detectable change in the physiology of a recipient subject. In the present context, an agent is physiologically significant if its presence results in the inhibition of the growth of tumor cells or in the inhibition of a viral infection. An inhibition of tumor growth may be indicated, for example, by a decrease in the number of tumor cells, decreased metastasis, a decrease in the size of a solid tumor, or increased necrosis of a tumor. Indicators of viral infection inhibition include decreased viral titer, a decrease in detectable viral antigen, or an increase in anti-viral antibody titer.

A pharmaceutical composition comprising Zcyto13 (or Zcyto13 analog or fusion protein) can be furnished in liquid form, in an aerosol, or in solid form. Liquid forms, are illustrated by injectable solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems,* Ranade and Hollinger (eds.), pages 95–123 (CRC Press 1995); Bremer et al., "Protein Delivery with Infusion Pumps," in *Protein Delivery: Physical Systems,* Sanders and Hendren (eds.), pages 239–254 (Plenum Press 1997); Yewey et al., "Delivery of Proteins from a Controlled Release Injectable Implant," in *Protein Delivery: Physical Systems,* Sanders and Hendren (eds.), pages 93–117 (Plenum Press 1997)). For example, Cleland and Jones, *Pharm. Res.* 13:1464 (1996), describe a method for producing interferon-γ encapsulated in polylactic-coglycolic microspheres.

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (*Suppl.* 1):S61 (1993), Kim, *Drugs* 46:618 (1993), and Ranade, "Site-Specific Drug Delivery Using Liposomes as Carriers," in *Drug Delivery Systems,* Ranade and Hollinger (eds.), pages 3–24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 μm to greater than 10 μm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N.Y Acad. Sci.* 446:368 (1985)). After intravenous administration, small liposomes (0.1 to 1.0 μm) are typically taken up by cells of the reticuloendothelial system, located principally in the liver and spleen, whereas liposomes larger than 3.0 μm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., *Biochim. Biophys. Acta* 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta* 1068:133 (1991); Allen et al., *Biochim. Biophys. Acta* 1150:9 (1993)).

Liposomes can also be prepared to target particular cells or organs by varying phospholipid composition or by inserting receptors or ligands into the liposomes. For example, liposomes, prepared with a high content of a nonionic surfactant, have been used to target the liver (Hayakawa et al., Japanese Patent 04-244,018; Kato et al., *Biol. Pharm. Bull.* 16:960 (1993)). These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., *Biol. Pharm. Bull.* 20:881 (1997)).

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drug Carrier Syst.* 14:287 (1997); Murahashi et al., *Biol. Pharm. Bull.*20:259 (1997)). Similarly, Wu et al., *Hepatology* 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.*20:259 (1997)). Polyaconitylated human serum albumin liposomes provide another approach for targeting liposomes to liver cells (Kamps et al., *Proc. Nat'l Acad. Sci. USA* 94:11681 (1997)). Moreover, Geho, et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a ligand expressed by the target cell (Harasym et al., *Adv. Drug Deliv. Rev.* 32:99 (1998)). After plasma elimination of free antibody, streptavidin-conjugated liposomes are administered. In another approach, targeting antibodies are directly attached to liposbmes (Harasym et al., *Adv. Drug Deliv. Rev.* 32:99 (1998)).

Polypeptides having Zcyto13 activity can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome Technology,* 2nd Edition, Vol. III, Gregoriadis (ed.), page 317 (CRC Press 1993), Wassef et al., *Meth. Enzymol.* 149:124 (1987)). As noted above, therapeutically useful liposomes may contain a variety of components. For example, liposomes may comprise lipid derivatives of poly (ethylene glycol) (Allen et al., *Biochim. Biophys. Acta* 1150:9 (1993)).

Degradable polymer microspheres have been designed to maintain high systemic levels of therapeutic proteins. Microspheres are prepared from degradable polymers such as poly(lactide-co-glycolide) (PLG), polyanhydrides, poly (ortho esters), nonbiodegradable ethylvinyl acetate polymers, in which proteins are entrapped in the polymer (Gombotz and Pettit, *Bioconjugate Chem.* 6:332 (1995); Ranade, "Role of Polymers in Drug Delivery," in *Drug Delivery Systems,* Ranade and Hollinger (eds.), pages 51–93 (CRC Press 1995); Roskos and Maskiewicz, "Degradable Controlled Release Systems Useful for Protein Delivery," in *Protein Delivery: Physical Systems,* Sanders and Hendren (eds.), pages 45–92 (Plenum Press 1997); Bartus et al., *Science* 281:1161 (1998); Putney and Burke, *Nature Biotechnology* 16:153 (1998); Putney, *Curr. Opin. Chem. Biol.* 2:548 (1998)). Polyethylene glycol (PEG)-coated nanospheres can also provide carriers for intravenous administration of therapeutic proteins (see, for example, Gref et al., *Pharm. Biotechnol.* 10:167 (1997)).

The present invention also contemplates chemically modified polypeptides having Zcyto13 activity and Zcyto13 antagonists, in which a polypeptide is linked with a polymer, as discussed above.

Other dosage forms can be devised by those skilled in the art, as shown, for example, by Ansel and Popovich, *Pharmaceutical Dosage Forms and Drug Delivery Systems, 5$^{th}$* Edition (Lea & Febiger 1990), Gennaro (ed.), *Remington's Pharmaceutical Sciences,* 19$^{th}$ Edition (Mack Publishing Company 1995), and by Ranade and Hollinger, *Drug Delivery Systems* (CRC Press 1996).

As an illustration, pharmaceutical compositions may be supplied as a kit comprising a container that comprises a molecule having Zcyto13 activity or a Zcyto13 antagonist. Therapeutic polypeptides can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide. Such a kit may further comprise written information on indications and usage of the pharmaceutical composition. Moreover, such information may include a statement that the Zcyto13 composition is contraindicated in subjects with known hypersensitivity to Zcyto13.

13. Therapeutic Uses of Zcyto13 Nucleotide Sequences

Immunomodulator genes can be introduced into a subject to enhance immunological responses. As an illustration "immunomodulator gene therapy" has been examined in model systems using vectors that express IL-2, IL-3, IL4, IL-6, IL-10, IL-12, IL-15, interferon-γ, tumor necrosis factor-α, or granulocyte-macrophage colony-stimulating factor (see, for example, Cao et al., *J. Gastroenterol. Hepatol.* 11:1053 (1996), Tahara et al., *Ann. N. Y. Acad. Sci.* 795:275 (1996), Rakhmilevich et al., *Hum. Gene Ther.* 8:1303 (1997), and Cao et al., *Transplantation* 65:325 (1998)). The present invention includes the use of Zcyto13 nucleotide sequences to augment an immunological response to a tumor or viral infection in a subject. In addition, a therapeutic expression vector can be provided that inhibits Zcyto13 gene expression, such as an anti-sense molecule, a ribozyme, or an external guide sequence molecule.

There are numerous approaches to introduce a Zcyto13 gene to a subject, including the use of recombinant host cells that express Zcyto13, delivery of naked nucleic acid encoding Zcyto13, use of a cationic lipid carrier with a nucleic acid molecule that encodes Zcyto13, and the use of viruses that express Zcyto13, such as recombinant retroviruses, recombinant adeno-associated viruses, recombinant adenoviruses, and recombinant Herpes simplex viruses [HSV] (see, for example, Mulligan, *Science* 260:926 (1993), Rosenberg et al., *Science* 242:1575 (1988), LaSalle et al., *Science* 259:988 (1993), Wolff et al., *Science* 247:1465 (1990), Breakfield and Deluca, *The New Biologist* 3:203 (1991)). In an ex vivo approach, for example, cells are isolated from a subject, transfected with a vector that expresses a Zcyto13 gene, and then transplanted into the subject.

In order to effect expression of a Zcyto13 gene, an expression vector is constructed in which a nucleotide sequence encoding a Zcyto13 gene is operably linked to a core promoter, and optionally a regulatory element, to control gene transcription. The general requirements of an expression vector are described above.

Alternatively, a Zcyto13 gene can be delivered using recombinant viral vectors, including for example, adenoviral vectors (e.g., Kass-Eisler et al., *Proc. Nat'l Acad. Sci. USA* 90:11498 (1993), Kolls et al., *Proc. Nat'l Acad. Sci. USA* 91:215 (1994), Li et al., *Hum. Gene Ther.* 4:403 (1993), Vincent et al., *Nat. Genet.* 5:130 (1993), and Zabner et al., *Cell* 75:207 (1993)), adenovirus-associated viral vectors (Flotte et al., *Proc. Nat'l Acad. Sci. USA* 90:10613 (1993)), alphaviruses such as Semliki Forest Virus and Sindbis Virus (Hertz and Huang, *J. Vir.* 66:857 (1992), Raju and Huang, *J. Vir.* 65:2501 (1991), and Xiong et al., *Science* 243:1188 (1989)), herpes viral vectors (e.g., U.S. Pat. Nos. 4,769,331, 4,859,587, 5,288,641 and 5,328,688), parvovirus vectors (Koering et al., *Hum. Gene Therap.* 5:457 (1994)), pox virus vectors (Ozaki et al., *Biochem. Biophys. Res. Comm.* 193:653 (1993), Panicali and Paoletti, *Proc. Nat'l Acad. Sci. USA* 79:4927 (1982)), pox viruses, such as canary pox virus or vaccinia virus (Fisher-Hoch et al., *Proc. Nat'l Acad Sci. USA* 86:317 (1989), and Flexner et al., *Ann. N.Y. Acad. Sci.* 569:86 (1989)), and retroviruses (e.g., Baba et al., *J. Neurosurg* 79:729 (1993), Ram et al., *Cancer Res.* 53:83 (1993), Takamiya et al., *J. Neurosci. Res* 33:493 (1992), Vile and Hart, *Cancer Res.* 53:962 (1993), Vile and Hart, *Cancer Res.* 53:3860 (1993), and Anderson et al., U.S. Pat. No. 5,399, 346). Within various embodiments, either the viral vector itself, or a viral particle which contains the viral vector may be utilized in the methods and compositions described below.

As an illustration of one system, adenovirus, a double-stranded DNA virus, is a well-characterized gene transfer vector for delivery of a heterologous nucleic acid molecule (for a review, see Becker et al., *Meth. Cell Biol.* 43:161 (1994); Douglas and Curiel, *Science & Medicine* 4:44 (1997)). The adenovirus system offers several advantages including: (i) the ability to accommodate relatively large DNA inserts, (ii) the ability to be grown to high-titer, (iii) the ability to infect a broad range of mammalian cell types, and (iv) the ability to be used with many different promoters including ubiquitous, tissue specific, and regulatable promoters. In addition, adenoviruses can be administered by intravenous injection, because the viruses are stable in the bloodstream.

Using adenovirus vectors where portions of the adenovirus genome are deleted, inserts are incorporated into the viral DNA by direct ligation or by homologous recombination with a co-transfected plasmid. In an exemplary system, the essential E1 gene is deleted from the viral vector, and the virus will not replicate unless the E1 gene is provided by the host cell. When intravenously administered to intact animals, adenovirus primarily targets the liver. Although an adenoviral delivery system with an E1 gene deletion cannot replicate in the host cells, the host's tissue will express and process an encoded heterologous protein. Host cells will also secrete the heterologous protein if the corresponding gene includes a secretory signal sequence. Secreted proteins will enter the circulation from tissue that expresses the heterologous gene (e.g., the highly vascularized liver).

Moreover, adenoviral vectors containing various deletions of viral genes can be used to reduce or eliminate immune responses to the vector. Such adenoviruses are E1-deleted, and in addition, contain deletions of E2A or E4 (Lusky et al., *J. Virol.* 72:2022 (1998); Raper et al., *Human Gene Therapy* 9:671 (1998)). The deletion of E2b has also been reported to reduce immune responses (Amalfitano et al., *J. Virol.* 72:926 (1998)). By deleting the entire adenovirus genome, very large inserts of heterologous DNA can be accommodated. Generation of so called "gutless" adenoviruses, where all viral genes are deleted, are particularly advantageous for insertion of large inserts of heterologous DNA (for a review, see Yeh. and Perricaudet, *FASEB J.* 11:615 (1997)).

High titer stocks of recombinant viruses capable of expressing a therapeutic gene can be obtained from infected mammalian cells using standard methods. For example, recombinant HSV can be prepared in Vero cells, as described by Brandt et al., *J. Gen. Virol.* 72:2043 (1991), Herold et al., *J. Gen. Virol.* 75:1211 (1994), Visalli and Brandt, *Virology* 185:419 (1991), Grau et al., *Invest. Ophthalmol. Vis. Sci.* 30:2474 (1989), Brandt et al., *J. Virol. Meth.* 36:209 (1992), and by Brown and MacLean (eds.), *HSV Virus Protocols* (Humana Press 1997).

Alternatively, an expression vector comprising a Zcyto13 gene can be introduced into a subject's cells by lipofection in vivo using liposomes. Synthetic cationic lipids can be used to prepare liposomes for in vivo transfection of a gene encoding a marker (Felgner et al., *Proc. Nat'l Acad. Sci. USA* 84:7413 (1987); Mackey et al., *Proc. Nat'l Acad. Sci. USA* 85:8027 (1988)). The use of lipofection to introduce exogenous genes into specific organs in vivo has certain practical advantages. Liposomes can be used to direct transfection to particular cell types, which is particularly advantageous in a tissue with cellular heterogeneity, such as the pancreas, liver, kidney, and brain. Lipids may be chemically coupled to other molecules for the purpose of targeting. Targeted peptides (e.g, hormones or neurotransmitters), proteins such as antibodies, or non-peptide molecules can be coupled to liposomes chemically.

Electroporation is another alternative mode of administration. For example, Aihara and Miyazaki, *Nature Biotechnology* 16:867 (1998), have demonstrated the use of in vivo electroporation for gene transfer into muscle.

In an alternative approach to gene therapy, a therapeutic gene may encode a Zcyto13 anti-sense RNA that inhibits the expression of Zcyto13. Suitable sequences for anti-sense molecules can be derived from the nucleotide sequences of Zcyto13 disclosed herein.

Alternatively, an expression vector can be constructed in which a regulatory element is operably linked to a nucleotide sequence that encodes a ribozyme. Ribozymes can be designed to express endonuclease activity that is directed to a certain target sequence in a mRNA molecule (see, for example, Draper and Macejak, U.S. Pat. No. 5,496,698, McSwiggen, U.S. Pat. No. 5,525,468, Chowrira and McSwiggen, U.S. Pat. No. 5,631,359, and Robertson and Goldberg, U.S. Pat. No. 5,225,337). In the context of the present invention, ribozymes include nucleotide sequences that bind with Zcyto13 mRNA.

In another approach, expression vectors can be constructed in which a regulatory element directs the production of RNA transcripts capable of promoting RNase P-mediated cleavage of mRNA molecules that encode a Zcyto13 gene. According to this approach, an external guide sequence can be constructed for directing the endogenous ribozyme, RNase P, to a particular species of intracellular mRNA, which is subsequently cleaved by the cellular ribozyme (see, for example, Altman et al., U.S. Pat. No. 5,168,053, Yuan et al., Science 263:1269 (1994), Pace et al., international publication No. WO 96/18733, George et al., international publication No. WO 96/21731, and Werner et al., international publication No. WO 97/33991). Preferably, the external guide sequence comprises a ten to fifteen nucleotide sequence complementary to Zcyto13 mRNA, and a 3'-NCCA nucleotide sequence, wherein N is preferably a purine. The external guide sequence transcripts bind to the targeted mRNA species by the formation of base pairs between the mRNA and the complementary external guide sequences, thus promoting cleavage of mRNA by RNase P at the nucleotide located at the 5'-side of the base-paired region.

In general, the dosage of a composition comprising a therapeutic vector having a Zcyto13 nucleotide acid sequence, such as a recombinant virus, will vary depending upon such factors as the subject's age, weight, height, sex, general medical condition and previous medical history. Suitable routes of administration of therapeutic vectors include intravenous injection, intraarterial injection, intraperitoneal injection, intramuscular injection, intratumoral injection, and injection into a cavity that contains a tumor. As an illustration, Horton et al., Proc. Nat'l Acad Sci. USA 96:1553 (1999), demonstrated that intramuscular injection of plasmid DNA encoding interferon-α produces potent antitumor effects on primary and metastatic tumors in a murine model.

A composition comprising viral vectors, non-viral vectors, or a combination of viral and non-viral vectors of the present invention can be formulated according to known methods to prepare pharmaceutically useful compositions, whereby vectors or viruses are combined in a mixture with a pharmaceutically acceptable carrier. As noted above, a composition, such as phosphate-buffered saline is said to be a "pharmaceutically acceptable carrier" if its administration can be tolerated by a recipient subject. Other suitable carriers are well-known to those in the art (see, for example, Remington's Pharmaceutical Sciences, 19th Ed (Mack Publishing Co. 1995), and Gilman's the Pharmacological Basis of Therapeutics, 7th Ed. (MacMillan Publishing Co. 1985)).

For purposes of therapy, a therapeutic gene expression vector, or a recombinant virus comprising such a vector, and a pharmaceutically acceptable carrier are administered to a subject in a therapeutically effective amount. A combination of an expression vector (or virus) and a pharmaceutically acceptable carrier is said to be administered in a "therapeutically effective amount" if the amount administered is physiologically significant. An agent is physiologically significant if its presence results in a detectable change in the physiology of a recipient subject. In the present context, an agent is physiologically significant if its presence inhibits the growth of tumor cells or inhibits viral infection. An inhibition of tumor growth may be indicated, for example, by a decrease in the number of tumor cells, decreased metastasis, a decrease in the size of a solid tumor, or increased necrosis of a tumor. Indicators of viral infection inhibition include decreased viral titer, a decrease in detectable viral antigen, or an increase in anti-viral antibody titer.

When the subject treated with a therapeutic gene expression vector or a recombinant virus is a human, then the therapy is preferably somatic cell gene therapy. That is, the preferred treatment of a human with a therapeutic gene expression vector or a recombinant virus does not entail introducing into cells a nucleic acid molecule that can form part of a human germ line and be passed onto successive generations (i.e., human germ line gene therapy).

14. Production of Transgenic Mice

Transgenic mice can be engineered to over-express the Zcyto13 gene in all tissues or under the control of a tissue-specific or tissue-preferred regulatory element. These over-producers of Zcyto13 can be used to characterize the phenotype that results from over-expression, and the transgenic animals can serve as models for human disease caused by excess Zcyto13. Transgenic mice that over-express Zcyto13 also provide model bioreactors for production of Zcyto13 in the milk or blood of larger animals. Methods for producing transgenic mice are well-known to those of skill in the art (see, for example, Jacob, "Expression and Knock-out of Interferons in Transgenic Mice," in Overexpression and Knockout of Cytokines in Transgenic Mice, Jacob (ed.), pages 111–124 (Academic Press, Ltd. 1994), Monastersky and Robl (eds.), Strategies in Transgenic Animal Science (ASM Press 1995), and Abbud and Nilson, "Recombinant Protein Expression in Transgenic Mice," in Gene Expression Systems: Using Nature for the Art of Expression, Fernandez and Hoeffier (eds.), pages 367–397 (Academic Press, Inc. 1999)).

For example, a method for producing a transgenic mouse that expresses a Zcyto13 gene can begin with adult, fertile males (studs) (B6C3fl, 2–8 months of age (Taconic Farms, Germantown, N.Y.)), vasectomized males (duds) (B6D2fl, 2–8 months, (Taconic Farms)), prepubescent fertile females (donors) (B6C3fl, 4–5 weeks, (Taconic Farms)) and adult fertile females (recipients) (B6D2fl, 2–4 months, (Taconic Farms)). The donors are acclimated for one week and then injected with approximately 8 IU/mouse of Pregnant Mare's Serum gonadotrophin (Sigma Chemical Company; St. Louis, Mo.) I.P., and 46–47 hours later, 8 IU/mouse of human Chorionic Gonadotropin (hCG (Sigma)) I.P. to induce superovulation. Donors are mated with studs subsequent to hormone injections. Ovulation generally occurs within 13 hours of hCG injection. Copulation is confirmed by the presence of a vaginal plug the morning following mating.

Fertilized eggs are collected under a surgical scope. The oviducts are collected and eggs are released into urinanalysis slides containing hyaluronidase (Sigma). Eggs are washed once in hyaluronidase, and twice in Whitten's W640 medium (described, for example, by Menino and O'Claray, Biol. Reprod. 77:159 (1986), and Dienhart and Downs, Zygote 4:129 (1996)) that has been incubated with 5% $CO_2$, 5% $O_2$, and 90% $N_2$ at 37° C. The eggs are then stored in a 37° C./5% $CO_2$ incubator until microinjection.

Ten to twenty micrograms of plasmid DNA containing a Zcyto13 encoding sequence is linearized, gel-purified, and resuspended in 10 mM Tris-HCl (pH 7.4), 0.25 mM EDTA (pH 8.0), at a final concentration of 5–10 nanograms per microliter for microinjection. For example, the Zcyto13 encoding sequences can encode amino acid residues 22 to 199 of SEQ ID NO:2.

Plasmid DNA is microinjected into harvested eggs contained in a drop of W640 medium overlaid by warm, $CO_2$-equilibrated mineral oil. The DNA is drawn into an injection needle (pulled from a 0.75 mm ID, 1 mm OD borosilicate glass capillary), and injected into individual eggs. Each egg is penetrated with the injection needle, into one or both of the haploid pronuclei.

Picoliters of DNA are injected into the pronuclei, and the injection needle withdrawn without coming into contact with the nucleoli. The procedure is repeated until all the eggs are injected. Successfully microinjected eggs are transferred into an organ tissue-culture dish with pre-gassed W640 medium for storage overnight in a 37° C./5% $CO_2$ incubator.

The following day, two-cell embryos are transferred into pseudopregnant recipients. The recipients are identified by the presence of copulation plugs, after copulating with vasectomized duds. Recipients are anesthetized and shaved on the dorsal left side and transferred to a surgical microscope. A small incision is made in the skin and through the muscle wall in the middle of the abdominal area outlined by the ribcage, the saddle, and the hind leg, midway between knee and spleen. The reproductive organs are exteriorized onto a small surgical drape. The fat pad is stretched out over the surgical drape, and a baby serrefine (Roboz, Rockville, Md.) is attached to the fat pad and left hanging over the back of the mouse, preventing the organs from sliding back in.

With a fine transfer pipette containing mineral oil followed by alternating W640 and air bubbles, 12–17 healthy two-cell embryos from the previous day's injection are transferred into the recipient. The swollen ampulla is located and holding the oviduct between the ampulla and the bursa, a nick in the oviduct is made with a 28 g needle close to the bursa, making sure not to tear the ampulla or the bursa.

The pipette is transferred into the nick in the oviduct, and the embryos are blown in, allowing the first air bubble to escape the pipette. The fat pad is gently pushed into the peritoneum, and the reproductive organs allowed to slide in. The peritoneal wall is closed with one suture and the skin closed with a wound clip. The mice recuperate on a 37° C. slide warmer for a minimum of four hours.

The recipients are returned to cages in pairs, and allowed 19–21 days gestation. After birth, 19–21 days postpartum is allowed before weaning. The weanlings are sexed and placed into separate sex cages, and a 0.5 cm biopsy (used for genotyping) is snipped off the tail with clean scissors.

Genomic DNA is prepared from the tail snips using, for example, a QIAGEN DNEASY kit following the manufacturer's instructions. Genomic DNA is analyzed by PCR using primers designed to amplify a Zcyto13 gene or a selectable marker gene that was introduced in the same plasmid. Illustrative primers suitable for amplifying Zcyto13 are described in the Examples, below. After animals are confirmed to be transgenic, they are back-crossed into an inbred strain by placing a transgenic female with a wild-type male, or a transgenic male with one or two wild-type female(s). As pups are born and weaned, the sexes are separated, and their tails snipped for genotyping.

To check for expression of a transgene in a live animal, a partial hepatectomy is performed. A surgical prep is made of the upper abdomen directly below the zyphoid process. Using sterile technique, a small 1.5–2 cm incision is made below the sternum and the left lateral lobe of the liver exteriorized. Using 4–0 silk, a tie is made around the lower lobe securing it outside the body cavity. An atraumatic clamp is used to hold the tie while a second loop of absorbable Dexon (American Cyanamid; Wayne, N.J.) is placed proximal to the first tie. A distal cut is made from the Dexon tie and approximately 100 mg of the excised liver tissue is placed in a sterile petri dish. The excised liver section is transferred to a 14 ml polypropylene round bottom tube and snap frozen in liquid nitrogen and then stored on dry ice. The surgical site is closed with suture and wound clips, and the animal's cage placed on a 37° C. heating pad for 24 hours post operatively. The animal is checked daily post operatively and the wound clips removed 7–10 days after surgery. The expression level of Zcyto13 mRNA is examined for each transgenic mouse using an RNA solution hybridization assay or polymerase chain reaction.

This general approach was used to produce transgenic mice comprising a Zcyto13 expression vector. The vector contained a Zcyto13 gene that was synthesized with PCR primers ZC22243 (5' CGT ACG GGC CGG CCA CCA TGA CTC CAA AGT TT 3'; SEQ ID NO:14) and ZC22244 (5' CGC GCG GGC GCG CCC TAT TTA AGT TCT TGC TT 3'; SEQ ID NO:15). A preliminary study was performed with a male transgenic mouse, which expressed Zcyto13 in its liver. Flow cytometry analysis of spleen- and bone marrow-derived cells indicated that Zcyto13 may affect the development of the myeloid lineage in bone marrow.

In addition to producing transgenic mice that over-express Zcyto13, it is useful to engineer transgenic mice with either abnormally low or no expression of the gene. Such transgenic mice provide useful models for diseases associated with a lack of Zcyto13. As discussed above, Zcyto13 gene expression can be inhibited using anti-sense genes, ribozyme genes, or external guide sequence genes. To produce transgenic mice that under-express the Zcyto13 gene, such inhibitory sequences are targeted to Zcyto13 mRNA. Methods for producing transgenic mice that have abnormally low expression of a particular gene are known to those in the art (see, for example, Wu et al., "Gene Underexpression in Cultured Cells and Animals by Antisense DNA and RNA Strategies," in *Methods in Gene Biotechnology*, pages 205–224 (CRC Press 1997)).

An alternative approach to producing transgenic mice that have little or Zcyto13 gene expression is to generate mice having at least one normal Zcyto13 allele replaced by a nonfunctional Zcyto13 gene. One method of designing a nonfunctional Zcyto13 gene is to insert another gene, such as a selectable marker gene, within a nucleic acid molecule that encodes Zcyto13. Standard methods for producing these so-called "knockout mice" are known to those skilled in the art (see, for example, Jacob, "Expression and Knockout of Interferdns in Transgenic Mice," in *Overexpression and Knockout of Cytokines in Transgenic Mice*, Jacob (ed.), pages 111–124 (Academic Press, Ltd. 1994), and Wu et al., "New Strategies for Gene Knockout," in *Methods in Gene Biotechnology*, pages 339–365 (CRC Press 1997)).

The present invention, thus generally described, will be understood more readily by reference to the following examples, which is provided by way of illustration and is not intended to be limiting of the present invention.

EXAMPLE 1

Construction of a Nucleic Acid Molecule Encoding Zcyto13

5' RACE was performed to obtain a 5' sequence from an expressed sequence tag. The 5' RACE was performed as follows: 3 μl of 1/100 diluted placenta marathon cDNA, 20 pmoles each of oligonucleotide primers ZC9739 (5' CCA TCC TAA TAC GAC TCA CTA TAG GGC 3'; SEQ ID NO:5) and ZC20980 (5' ACT GCA CTG CCT TGA ACC CTG A 3'; SEQ ID NO:6), and 1 U of mixture of ExTaq/Taq antibody (1:1) were combined in 25 μl reactions. The reactions were run as follows: 94° C. for 2 minutes, then 30 cycles of 94° C. for 20 seconds, 64° C. for 30 seconds, 72° C. for 45 seconds, and the reaction was stopped with a 2 minute incubation at 72° C. One microliter each of 1/30 diluted first PCR product was used as template for a nested PCR. Twenty picomoles each of oligonucleotide primers ZC9719 (5' ACT CAC TAT AGG GCT CGA GCG GC 3'; SEQ ID NO:7) and ZC20981 (5' GTT CTT GCT TGA AGG TGG GTG ATT 3'; SEQ ID NO:8) and 1 U of mixture of ExTaq/Taq antibody (1:1) were combined in 25 μl reactions. The reactions were run as follows: 94° C. for 2 minutes, then 35 cycles of 94° C. for 20 seconds, 63° C. for 30 seconds, 72° C. for 45 seconds, and the reaction was stopped with a 4 minute incubation at 72° C. The PCR products were fractionated on an agarose gel. Obvious bands were obtained in placenta, purified with QIAquick (QIAGEN Inc.; Valencia, Calif.) and ligated into a pCR2.1 vector using TA cloning kit (Invitrogen). Clones with inserts were sequenced, and the results indicated that the 5' RACE product contained the 5' stop codon, first Met and signal peptide information for a full length cDNA.

New primers ZC21590 (5' ATA CTA AGC ACC AGG GTT GAG AAT G 3'; SEQ ID NO:9) and ZC21591 (5' AGG TAG CAT TAG CAG CAT CCT GGT A 3'; SEQ ID NO:10) were designed according to the new 5' sequence information on the clone. PCR was used to amplify entire coding sequence with the primer pair above, and RNA samples from placenta, testis and 7d embryo tissues were used as templates. Three microliters of 1/100 diluted marathon cDNAs, 20 pmoles of each oligonucleotide primers, and 1 U of mixture of ExTaq/Taq antibody (1:1) were used in 25 μl reactions. The reactions were run as follows: 94° C. for 2 minutes, then 35 cycles of 94° C. for 20 seconds, 61° C. for 30 seconds, 72° C. for 30 seconds, and the reactions were stopped with a 4 minute incubation at 72° C. PCR products were separated on an agarose gel and purified with QIAquick (QIAGEN Inc.). Purified PCR products were then ligated into pCR2.1 vector using TA cloning kit (Invitrogen) and inserts were sequenced.

EXAMPLE 2

Expression of the Zcyto13 Gene

Northern analyses were performed using a Mouse Multiple Tissue Northern Blot, a Mouse Embryo Multiple Tissue Northern Blot, and a Mouse RNA Master Blot (dot blot) (CLONTECH Laboratories, Inc., Palo Alto, Calif.). The hybridization probe was generated from a gel purified PCR amplification product. The probe was made using ZC20979 (5' CTG ACA GTC TAC CTG GAG TTG GG 3'; SEQ ID NO:11) and ZC20980 as primers and mouse seven-day embryo Marathon Ready cDNA as template. The probe length was 310 base pairs. The probe was a radioactively labeled using the REDIPRIME II labeling kit (AMERSHAM PHARMACIA BIOTECH, Inc.; Piscataway, N.J.) according to the manufacturer's protocol. The probe was purified using a NUCTRAP push column (STRATAGENE, La Jolla, Calif.). EXPRESSHYB (CLONTECH) solution was used for the prehybridization and hybridization solutions for the Northern blots. Hybridization took place overnight at 65° C. Following hybridization, the blots were washed in 2×SSC, 0.1% SDS at room temperature, followed by a wash in 0.1×SSC and 0.1% SDS at 50° C. The blots were exposed to Kodak BioMax film. Bands at 6.5 kilobases and 2.8 kilobases were clearly visible in he, brain, liver, kidney, and seven-day embryo on the Northern blots. Faint bands at the same size were also visible in lung and testes. The RNA Master Blot showed positive signals from heart, submaxillary gland, epididymus, and seven-day embryo.

EXAMPLE 3

Southern Analysis of the Zcyto13 Gene

Southern analysis was performed using a commercially prepared Interspecies Zoo-Blot from CLONTECH Laboratories, Inc. The Southern blot contained EcoRI-digested DNA. The hybridization probe was generated as described for Example 2. The probe was a radioactively labeled using the REDIPRIME II labeling kit (AMERSHAM PHARMACIA BIOTECH, Inc.; Piscataway, N.J.) according to the manufacturer's protocol, and the probe was purified using a NUCTRAP push column (STRATAGENE, La Jolla, Calif.). EXPRESSHYB (CLONTECH) solution was used for th e prehybridization and hybridization solutions for the Southern blots. The blot was hybridized overnight at 65° C., and then, the blots were washed in 2×SSC, 0.1% SDS at room temperature, followed by a wash in 0.1×SSC and 0.1% SDS at 50° C. After washing, the blot s were exposed to Kodak BioMax film. The mouse genomic DNA s ample contained hybridizing fragments at approximately 5.65 and 4.8 kilobases, while the rat sample contained hybridizing fragments at approximately 5.2 and 2.1 kilobases.

EXAMPLE 4

Expression of the Zcyto13 Gene Using Adenovirus Constructs

1. Generation of Untagged Zyctol 3 Recombinant Adenovirus

The protein coding region of murine Zcyto13 was amplified by PCR using primers that added FseI and AscI restriction s ties at the 5' and 3' termini respectively. PCR primers ZC21924 (5' CAC ACA GGC CGG CCA CCA TRA CTC CAA AGT TTT TAT GGC 3'; SEQ ID NO:12) and ZC21923 (5' CAC ACA GGC GCG CCT CTA TTT AAG TTC TTG CTT GAA GGT GGG 3'; SEQ ID NO:13) were used with template pCr2.1 plasmid containing the fill-length murine Zcyto13 cDNA in a PCR reaction as follows: one cycle at 95° C. for 5 minutes, followed by 15 cycles at 95° C. for 0.5 minute, 58° C. for 0.5 minute, and 72° C. for 0.5 minute, followed by 72° C. for 7 minutes, followed by a 4° C. soak. The PCR reaction product was loaded onto a 1.2% (low melt) SEAPLAQUE OTO (FMC BioProducts; Rockland, Me.) gel in TAE buffer. The Zcyto13 PCR product was excised from the gel, melted at 65°, phenol extracted twice and then ethanol precipitated. The PCR product was then digested with FseI-AscI, phenol/chloroform extracted, ethanol precipitated, and rehydrated in 20 μl TE (Tris/EDTA, pH 8).

The 600 base pair Zcyto13 fragment was then ligated into the FseI-AscI sites of a modified pAdTrack CMV (He et al., Proc. Nat'l Acad. Sci. USA 95:2509 (1998)). This construct also contains the green fluorescent protein (GFP) marker gene. The CMV promoter driving GFP expression was replaced with the SV40 promoter and the SV40 polyadenylation signal was replaced with the human growth hormone polyadenylation signal. In addition, the native polylinker was replaced with FseI, EcoRV, and AscI sites. This modified form of pAdTrack CMV was named pZyTrack. Ligation was performed using the FAST-LINK DNA ligation and screening kit (EPICENTRE TECHNOLOGIES; Madison, Wis.). Clones containing the Zcyto13 cDNA were identified by standard mini prep procedures. In order to linearize the plasmid, approximately 5 µg of the pZyTrack Zcyto13 plasmid were digested with PmeI. Approximately 1 µg of the linearized plasmid was cotransformed with 200 ng of supercoiled pAdEasy (He et al., Proc. Nat'l Acad. Sci. USA 95–2509 (1998)) into BJ5183 cells. The co-transformation was performed with a BIO-RAD GENE PULSER (BIO-RAD laboratories, Inc.; Hercules, Calif.) at 2.5 kV, 200 ohms and 25 mFa. The entire co-transformation was plated on four LB plates containing 25 µg/ml kanarnycin. The smallest colonies were picked and expanded in LB/kanamycin and recombinant adenovirus DNA identified by standard DNA miniprep procedures. Digestion of the recombinant adenovirus DNA with FseI-AscI confirmed the presence of Zcyto13. The recombinant adenovirus miniprep DNA was transformed into DH10B competent cells and DNA prepared using a QIAGEN maxi prep kit as per kit instructions.

2. Transfection of 293A Cells with Recombinant DNA

Approximately 5 µg of recombinant adenoviral DNA were digested with PacI enzyme for three hours at 37° C. in a reaction volume of 100 µl containing 20–30 U of PacI. The digested DNA was extracted twice with an equal volume of phenol/chloroform and precipitated with ethanol. The DNA pellet was resuspended in 5 µl distilled water. QBI-293A cells (Quantum Biotechnologies, Inc.; Montreal, Quebec, Canada), inoculated the day before and grown to 60–70% confluence in a T25 flask, were transfected with the PacI digested DNA. The PacI-digested DNA was diluted up to a total volume of 50 µl with sterile HBS (150 mM NaCl, 20 mM HEPES). In a separate tube, 25 µl DOTAP (1 mg/ml; Roche Molecular Biochemicals; Indianapolis, Ind.) were diluted to a total volume of 100 µl with HBS. The DNA was added to the DOTAP, mixed gently by pipeting up and down, and left at room temperature for 15 minutes. The medium was removed from the 293A cells and washed with 5 ml serum-free MEMalpha (LIFE TECHNOLOGIES, Inc; Rockville, Md.) containing 1 mM sodium pyruvate (LIFE TECHNOLOGIES, Inc), 0.1 mM MEM non-essential amino acids (LIFE TECHNOLOGIES, Inc) and 25 mM HEPES buffer (LIFE TECHNOLOGIES, Inc). Five milliliters of serum-free MEM were added to the 293A cells and held at 37° C. The DNA/lipid mixture was added drop-wise to the T25 flask of 293A cells, mixed gently and incubated at 37° C. for 4 hours. After four hours, the medium containing the DNA/lipid mixture was aspirated, and replaced with 5 ml complete MEM containing 5% fetal bovine serum. The transfected cells were monitored for green fluorescent protein (GFP) expression and formation of foci.

Seven days after transfection of 293A cells with the recombinant adenoviral DNA, the cells expressed the GFP protein and started to form foci. These foci are viral "plaques." The crude viral lysate was collected using a cell scraper to collect all of the 293A cells. The lysate was transferred to a 50 ml conical tube. To release most of the virus particles from the cells, three freeze/thaw cycles were performed in a dry ice/ethanol bath and a 37° water bath.

3. Amplification of Recombinant Adenovirus (rAdV)

The crude lysate was amplified ("primary amplification") to obtain a working stock of Zcyto13 rAdV lysate. Two hundred milliliters of crude rAdV lysate were added to each of ten 10 cm plates of nearly confluent (80–90%) 293A cells, which had been set up 20 hours previously. The plates were monitored for 48 to 72 hours for cytopathic effect under the white light microscope and expression of GFP under the fluorescent microscope. When all of the 293A cells showed cytopathic effect, this primary amplification stock lysate was collected and freeze/thaw cycles performed as described above.

Secondary amplification of Zcyto13 rAdV was obtained as follows. Twenty 15 cm tissue culture dishes of 293A cells were prepared so that the cells were 80–90% confluent. All but 20 milliliters of 5% MEM media was removed, and each dish was inoculated with 300–500 ml primary amplified rAdv lysate. After 48 hours, the 293A cells were lysed from virus production and this lysate was collected into 250 ml polypropylene centrifuge bottles and the rAdV purified.

4. AdV/cDNA Purification

NP-40 detergent was added to a final concentration of 0.5% to the bottles of crude lysate to lyse all cells. Bottles were placed on a rotating platform for 10 minutes, agitating as fast as possible without displacing the bottles. The debris was pelleted by centrifugation at 20,000×g for 15 minutes. The supernatant was transferred to 250 ml polycarbonate centrifuge bottles, and 0.5 volume of 20% PEG8000/2.5 M NaCl solution was added. The bottles were shaken overnight on ice. The bottles were centrifuged at 20,000×g for 15 minutes and supernatant discarded into a bleach solution. The precipitated virus/PEG appeared as a white precipitate located in two vertical lines along the wall of the bottle on either side of the spin mark. Using a sterile cell scraper, the precipitate from two bottles was resuspended in 2.5 ml PBS. The virus solution was placed in 2 ml microcentrifuge tubes and centrifuged at 14,000×g in the microfuge for 10 minutes to remove any additional cell debris. The supernatant from the 2 ml microcentrifuge tubes was transferred into a 15 ml polypropylene snapcap tube and adjusted to a density of 1.34 g/ml with cesium chloride (CsCl). The volume of the virus solution was estimated and 0.55 g/ml of was CsCl added. The CsCl was dissolved and 1 ml of this solution weighed 1.34 g. The solution was transferred to polycarbonate thick-walled centrifuge tubes, and centrifuged at 80,000 rpm (348,000×g) for 3–4 hours at 25° C. in a Beckman Optima TLX micro-ultracentrifuge with the TLA-100.4 rotor. The virus formed a white band. Using wide-bore pipette tips, the virus band was collected.

The virus from the gradient has a large amount of CsCl which must be removed before it can be used with cells. Pharmacia PD-10 columns prepacked with SEPHADEX G-25M (Amersham Pharmacia Biotech, Inc; Piscataway, N.J.) were used to desalt the virus preparation. The column was equilibrated with 20 ml of PBS. The virus was loaded and allowed to run into the column. Five milliliters of PBS were added to the column and fractions of 8–10 drops collected. The optical densities of 1:50 dilutions of each fraction were determined at 260 nm on a spectrophotometer. A clear absorbance peak was present between fractions 7–12. These fractions were pooled and the optical density (OD) of a 1:25 dilution determined. The following formula was used to convert OD into virus concentration: (OD at 260 nm)(25)($1.1 \times 10^{12}$)=virions/ml. The OD of a 1:25 dilution of the Zcyto13 rAdV was 0.059, giving a virus concentration of $4.9 \times 10^{12}$ virions/ml.

To store the virus, glycerol was added to the purified virus to a final concentration of 15%, mixed gently but effectively, and stored in aliquots at −80° C.

5. Viral Titration Assay

A protocol developed by Quantum Biotechnologies, Inc. (Montreal, Quebec, Canada) was followed to measure recombinant virus infectivity. Briefly, two 96-well tissue culture plates were seeded with 1×10⁴ 293A cells per well in MEM containing 2% fetal bovine serum for each recombinant virus assayed. After 24 hours, 10-fold dilutions of each virus from $1\times10^{-2}$ to $1\times10^{-14}$ were made in MEM containing 2% fetal bovine serum. One hundred microliters of each dilution were placed in each of 20 wells. After five days at 37° C., wells were read either positive or negative for cytopathic effect, and a value for "plaque forming units/ml" (PFU) is calculated.

The tissue culture infectious dose at 50% cytopathic effect ($TCID_{50}$) was produced as per Quantum Biotechnologies, Inc., above. The titer is determined from a plate in which virus is diluted from $10^{-2}$ to $10^{-14}$, and read five days after the infection. At each dilution a ratio (R) of positive wells for cytopathic effect per the total number of wells is determined.

To calculate the titer of the undiluted virus sample, factor "F" was first calculated, as 1+d(S-0.5), where "S" is the sum of the ratios (R), and "d" is $\log_{10}$ of the dilution series (e.g., "d" is equal to one for a ten-fold dilution series). The titer of the undiluted sample is calculated as: $10^{(1+F)}=TCID_{50}$/ml. To convert $TCID_{50}$/ml to pfu/ml, 0.7 is subtracted from the exponent in the calculation for titer (T). Using this method, the Zcyto13 adenovirus had a titer of $4.0\times10^9$ pfu/ml.

EXAMPLE 5

Biological Acivity of Zcyto13 Protein

1. Stimulation of Expression from an Interferon-Responsive Promoter

In one series of experiments, conditioned medium (CM) containing Zcyto13m protein was generated by infecting 293A cells with recombinant adenovirus containing the cDNA for Zcyto13m (AdZy-zcyto13m) at a multiplicity of infection of 400 particles per cell. CM was harvested at time points between 40 hours post infection and stored at −20° C. CM was also generated from an infection with a recombinant adenovirus lacking a cDNA (AdZy-parental). Prior to use, a portion of the CM was concentrated 14 fold in a Millipore Ultrafree-15 (5,000 nominal molecular weight limit) centrifugal filter and then, filtered through a Millipore Ultrafree-15 (100,000 nominal molecular weight limit) centrifugal filter to reduce the amount of viral particles present in the media, and finally filtered through a Millipore 0.2 μm syringe filter to sterilize the CM. Concentrated CM samples were diluted 1:2 in binding buffer and incubated with cells from a murine cell line for 5 hours at 37° C. CM containing Zcyto13 protein stimulated a 17-fold increase in gene expression from an interferon-responsive promoter, while control CM, appeared to stimulate gene expression by 1.4 fold. These results indicate that Zcyto13 induces expression from an interferon-responsive promoter.

2. Anti-Viral Activity of Zcyto13

Another series of experiments examined the anti-viral activity of Zcyto13. In these studies, the anti-viral assay was performed by plating L929 cells (ATCC No. CCL-1) in growth media RPMI medium 1640 containing 10% fetal bovine serum, penicillin, streptomycin, and L-glutamine in 96-well format at 50,000 cells per well. Adenovirus CM from 293A cells infected with either AdZy-zcyto13m or AdZy-parental, as described above, was incubated with cells overnight. A positive control in the assay was provided by murine interferon-α serially diluted 1:10, starting at 100 ng/ml. L929 cells with growth media alone provided the negative control. Treated cells were incubated for 24 hours. The media were discarded, fresh medium was added, and encephalomyocarditis virus (ATCC No. vr129b) was introduced at a multiplicity of infection of 0.1 (i.e., one virus particle for every ten L929 cells). The cells were incubated in the presence of the virus for 24 hours, and then, the wells were scored for percent cytopathic effect (CPE). As shown in Table 5, conditioned medium containing Zcyto13 effectively inhibited viral infection of the cells.

TABLE 5

| Treatment | Observed Cytopathic Effect |
| --- | --- |
| medium alone | none |
| encephalomyocarditis virus (EMCV) | >90% |
| interferon-α + EMCV | none |
| AdZy-parental + EMCV | >80% |
| AdZy-Zcyto13 + EMCV | none |

3. Mediation of Biological Activity Through the Human Interferon Receptor

Baf3, an interleukin-3 dependent pre-B cell line, was transfected with two chimeric receptors containing the extracellular domains of human interferon receptor and the signaling domains of murine MPL. The presence of the interferon-α/murine MPL and human interferon-β/murine MPL receptors was selected with zeocin (at 2 mg/ml) and puromycin (at 2 μg/ml).

Baby hamster kidney (BHK) cells were stably transfected with an expression vector containing the CMV promoter plus intron A upstream of either the murine Zcyto13 cDNA, or an unrelated cDNA, encoding "Zα30," using BRL lipofectamine. Stably transfected cells were seeded in a cell factory with serum free medium and allowed to grow for three days before conditioned media were harvested and concentrated in a 5K filter to 10×. Concentrated conditioned medium was stored at 4° C.

The assay to test for proliferation of Baf3 cells via signaling through the chimeric receptor was performed as follows. In a 96 well plate eight 1:2 serial dilutions of growth medium alone (RPMI 1640, 10% fetal bovine serum, 1 mM sodium pyruvate, 2 mM L-glutamine), murine interleukin-3 (starting at 50 pg/ml in growth medium), human interferon-α (starting at 100 ng/ml in growth medium), human interferon-β (starting at 100 ng/ml in growth medium), murine interferon-α (starting at 100 ng/ml in growth medium), murine interferon-β (starting at 100 ng/ml in growth medium), murine Zcyto13 (starting at 5× in assay) with and without anti-human interferon receptor chain 2 at 5 μg/ml per well (diluted in growth medium), and murine Zα30 (starting at 5× in assay). The final volume of each dilutions was 100 μl.

The Baf3 parental cell line and Baf3 cells transfected with human interferon/murine MPL receptor were washed three times in growth media (see above), pellets were resuspended in growth medium, and cells were counted and diluted in growth media to 5,000 cells/100 μl. One hundred microliters of diluted cells were added to each dilution of samples. The assay plate was incubated in a 37° C. incubator for three to four days. A 20 μl aliquot of Alomar blue was added to each well and the plate was incubated overnight at 37° C. The plates were read on the fluorescent plate reader at excitation wavelength of 544 and emission wavelength 590. The data demonstrated that interferon-α and -β are able to stimulate the Baf3 cells transfected with the chimeric receptors to proliferate. Zcyto13 was also able to stimulate proliferation in the transfected Baf3 cells, thus demonstrating that Zcyto13 signals through the human interferon receptor.

4. Antiproliferation Assay Using a BAF3 Cell Line

Baf3 was used to determine if Zcyto13 has antiproliferative properties. Baby hamster kidney (BHK) cells were stably transfected with an expression vector containing the CMV promoter plus intron A upstream of the murine Zcyto13 cDNA or an unrelated cDNA, called Zα30, using BRL lipofectamine. Stably transfected cells were seeded in a cell factory in serum free media and allowed to grow for three days before conditioned media was harvested and concentrated in a 5K filter to 10×. Concentrated conditioned medium samples were stored at 4° C.

The following assay was used to test for anti-proliferation of Baf3. In a 96 well plate, eight 1:2 serial dilutions were made of growth media alone (RPMI 1640, 10% fetal bovine serum, lmM sodium pyruvate, 2 mM L-glutamine), or murine IL-3 (starting at 50 pg/ml in growth medium) with final volume of 100 µl. Fifty microliters of the following were added to both growth media alone or mIL-3 diluted lanes: human interferon-α (100 ng/ml, 10 ng/ml, or 1 ng/ml diluted in growth medium), human interferon-β (100 ng/ml, 10 ng/ml, or 1 ng/ml diluted in growth medium), murine interferon-α (100 ng/ml, 10 ng/ml, or 1 ng/ml diluted in growth medium), murine interferon-β (100 ng/ml, 10 ng/ml, or 1 ng/ml diluted in growth medium), murine Zcyto13 (at 2.5×, 0.5×, or 0.1×), and murine Zα30 (at 2.5×, 0.5×, or 0.1×).

The Baf3cell line was washed three times in growth medium, pellets were resuspended in growth medium, cells were counted and diluted in growth medium to 5,000 cells/50 µl. Fifty microliters of diluted cells were then added to each dilution of samples. Assay plates were incubated in a 37° C. incubator for three to four days. Twenty microliters of Alomar blue were then added to each well and the plate were incubated overnight at 37° C. The plates were read on the fluorescent plate reader at excitation wavelength of 544 and emission wavelength 590. The results demonstrated that α-interferon and Zcyto13 inhibited proliferation of Baf3 cells.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated polypeptide comprising the amino acid sequence consisting of amino acid residues 22 to 199 of SEQ ID NO:2.

2. The isolated polypeptide of claim 1, wherein the polypeptide further comprises a signal secretory sequence that resides in an amino-terminal position relative to the amino acid sequence, wherein the signal secretory sequence comprises amino acid residues 1 to 21 of the amino acid sequence of SEQ ID NO:2.

3. A composition, comprising the isolated polypeptide of claim 1, and a carrier.

4. The composition of claim 3, wherein the isolated polypeptide comprises the amino acid sequence of SEQ ID NO:2.

5. An isolated polypeptide comprising an amino acid sequence that is a variant of amino acid residues 22 to 199 of SEQ ID NO:2, wherein any difference between amino acid residues 22 to 199 of SEQ ID NO:2 and the corresponding amino acid sequence of the variant is due to a conservative amino acid substitution, and wherein the isolated polypeptide exhibits anti-viral activity or anti-proliferative activity.

6. The isolated polypeptide of claim 5, wherein the amino acid sequence of the isolated polypeptide is characterized by at least one amino acid substitution within SEQ IS NO:2 selected from the group consisting of: (a) an alanine for glycine$^{39}$, (b) a valine for leucine$^{63}$, (c) a threonine for serine$^{81}$, (d) a valine for isoleucine$^{105}$, and (e) a leucine for valine$^{113}$.

7. An isolated polypeptide having an amino acid sequence consisting of the amino acid sequence SEQ ID NO:2.

\* \* \* \* \*

SEQUENCE LISTING

<160> NUMBER OF SEQ ID NOS: 22

<210> SEQ ID NO 1
<211> LENGTH: 768
<212> TYPE: DNA
<213> ORGANISM: mouse
<220> FEATURE:
<221> NAME/KEY: CDS
<222> LOCATION: (23)...(619)

<400> SEQUENCE: 1

```
atactaagca ccagggttga ga atg act cca aag ttt tta tgg ctg gtg gcc          52
                         Met Thr Pro Lys Phe Leu Trp Leu Val Ala
                          1               5                  10 ctt gtg gct cta tac att ccg ccc atc caa tct ctg aac tgt gtt tac         100
Leu Val Ala Leu Tyr Ile Pro Pro Ile Gln Ser Leu Asn Cys Val Tyr
             15                  20                  25 ctg gat gat agc atc ttg gaa aat gtg aaa ctt ctg ggc agt acc atg         148
Leu Asp Asp Ser Ile Leu Glu Asn Val Lys Leu Leu Gly Ser Thr Met
         30                  35                  40 acc ggc ttt ccc tta aga tgt cta aaa gat atc aca gat ttt aag ttt         196
Thr Gly Phe Pro Leu Arg Cys Leu Lys Asp Ile Thr Asp Phe Lys Phe
     45                  50                  55 cct aaa gag att ttg cca tac atc cag cat atg aaa agg gag ata aac         244
Pro Lys Glu Ile Leu Pro Tyr Ile Gln His Met Lys Arg Glu Ile Asn
 60                  65                  70 gcc gtc tcc tat cgt ata tcc tct ctg gca cta act atc ttc aat ctt         292
Ala Val Ser Tyr Arg Ile Ser Ser Leu Ala Leu Thr Ile Phe Asn Leu
75                  80                  85                  90 aaa ggc tcc atc cct cca gtg aca gag gaa cac tgg gaa cgt atc aga         340
Lys Gly Ser Ile Pro Pro Val Thr Glu Glu His Trp Glu Arg Ile Arg
                 95                 100                 105 tcg gga ctt ttc aaa caa gtg cgg caa gct caa gag tgc ttc atg gac         388
Ser Gly Leu Phe Lys Gln Val Arg Gln Ala Gln Glu Cys Phe Met Asp
            110                 115                 120 gag gag aaa gag aac agg gaa cat cct cac tcc gag gac ttc ctg aca         436
Glu Glu Lys Glu Asn Arg Glu His Pro His Ser Glu Asp Phe Leu Thr
        125                 130                 135 gtc tac ctg gag ttg ggc aag tat ttc ttc aga atc aaa aag ttc ctg         484
Val Tyr Leu Glu Leu Gly Lys Tyr Phe Phe Arg Ile Lys Lys Phe Leu
```

```
                   140                 145                 150
ata aat aag aaa tac agt ttc tgt gca tgg aag att gtc aca gtg gaa        532
Ile Asn Lys Lys Tyr Ser Phe Cys Ala Trp Lys Ile Val Thr Val Glu
155                 160                 165                 170 ata aga aga tgt ttc att ata ttt tcc aag tcc aga aaa cta ctc aaa        580
Ile Arg Arg Cys Phe Ile Ile Phe Ser Lys Ser Arg Lys Leu Leu Lys
                175                 180                 185 atg ata tca gaa tca ccc acc ttc aag caa gaa ctt aaa tagaagctgc         629
Met Ile Ser Glu Ser Pro Thr Phe Lys Gln Glu Leu Lys
                190                 195 aattgctcaa atgtctccaa gaacgcttta ttctaaagcc attaccagga tgctgctaat     689
gctaccttca gatgcaagac ttttcaagtt cagggttcaa ggcagtgcag tcaaagaaag     749
tcttaagcaa aagatgaac                                                  768

<210> SEQ ID NO 2
<211> LENGTH: 199
<212> TYPE: PRT
<213> ORGANISM: mouse

<400> SEQUENCE: 2

Met Thr Pro Lys Phe Leu Trp Leu Val Ala Leu Val Ala Leu Tyr Ile
1               5                   10                  15

Pro Pro Ile Gln Ser Leu Asn Cys Val Tyr Leu Asp Asp Ser Ile Leu
            20                  25                  30

Glu Asn Val Lys Leu Leu Gly Ser Thr Met Thr Gly Phe Pro Leu Arg
        35                  40                  45

Cys Leu Lys Asp Ile Thr Asp Phe Lys Phe Pro Lys Glu Ile Leu Pro
    50                  55                  60

Tyr Ile Gln His Met Lys Arg Glu Ile Asn Ala Val Ser Tyr Arg Ile
65                  70                  75                  80

Ser Ser Leu Ala Leu Thr Ile Phe Asn Leu Lys Gly Ser Ile Pro Pro
                85                  90                  95

Val Thr Glu Glu His Trp Glu Arg Ile Arg Ser Gly Leu Phe Lys Gln
            100                 105                 110

Val Arg Gln Ala Gln Glu Cys Phe Met Asp Glu Glu Lys Glu Asn Arg
        115                 120                 125

Glu His Pro His Ser Glu Asp Phe Leu Thr Val Tyr Leu Glu Leu Gly
    130                 135                 140

Lys Tyr Phe Phe Arg Ile Lys Lys Phe Leu Ile Asn Lys Lys Tyr Ser
145                 150                 155                 160

Phe Cys Ala Trp Lys Ile Val Thr Val Glu Ile Arg Arg Cys Phe Ile
                165                 170                 175

Ile Phe Ser Lys Ser Arg Lys Leu Leu Lys Met Ile Ser Glu Ser Pro
            180                 185                 190

Thr Phe Lys Gln Glu Leu Lys
        195

<210> SEQ ID NO 3
<211> LENGTH: 597
<212> TYPE: DNA
<213> ORGANISM: Artificial Sequence
<220> FEATURE:
<223> OTHER INFORMATION: This degenerate sequence encodes the amino acid
      sequence of SEQ ID NO:2.
<221> NAME/KEY: misc_feature
<222> LOCATION: (1)...(597)
<223> OTHER INFORMATION: n = A,T,C or G
```

-continued

<400> SEQUENCE: 3

```
atgacnccna arttyytntg gytngtngcn ytngtngcny tntayathcc nccnathcar     60
wsnytnaayt gygtntayyt ngaygaywsn athytngara aygtnaaryt nytnggnwsn    120
acnatgacng gnttyccnyt nmgntgyytn aargayatha cngayttyaa rttyccnaar    180
garathytnc cntayathca rcayatgaar mgngaratha aygcngtnws ntaymgnath    240
wsnwsnytng cnytnacnat httyaayytn aarggnwsna thccnccngt nacngargar    300
caytgggarm gnathmgnws nggnytntty aarcargtnm gncargcnca rgartgytty    360
atggaygarg araargaraa ymgngarcay ccncaywsng argayttyyt nacngtntay    420
ytngarytng gnaartaytt yttymgnath aaraarttyy tnathaayaa raartaywsn    480
ttytgygcnt ggaarathgt nacngtngar athmgnmgnt gyttyathat httywsnaar    540
wsnmgnaary tnytnaarat gathwsngar wsnccnacnt tyaarcarga rytnaar       597
```

<210> SEQ ID NO 4
<211> LENGTH: 16
<212> TYPE: PRT
<213> ORGANISM: Artificial Sequence
<220> FEATURE:
<223> OTHER INFORMATION: Peptide linker

<400> SEQUENCE: 4

```
Gly Gly Ser Gly Gly Ser Gly Gly Gly Gly Ser Gly Gly Gly Gly Ser
 1               5                  10                  15
```

<210> SEQ ID NO 5
<211> LENGTH: 27
<212> TYPE: DNA
<213> ORGANISM: Artificial Sequence
<220> FEATURE:
<223> OTHER INFORMATION: PCR primer

<400> SEQUENCE: 5

```
ccatcctaat acgactcact atagggc                                         27
```

<210> SEQ ID NO 6
<211> LENGTH: 22
<212> TYPE: DNA
<213> ORGANISM: Artificial Sequence
<220> FEATURE:
<223> OTHER INFORMATION: PCR primer

<400> SEQUENCE: 6

```
actgcactgc cttgaaccct ga                                              22
```

<210> SEQ ID NO 7
<211> LENGTH: 23
<212> TYPE: DNA
<213> ORGANISM: Artificial Sequence
<220> FEATURE:
<223> OTHER INFORMATION: PCR primer

<400> SEQUENCE: 7

```
actcactata gggctcgagc ggc                                             23
```

<210> SEQ ID NO 8
<211> LENGTH: 24
<212> TYPE: DNA
<213> ORGANISM: Artificial Sequence
<220> FEATURE:
<223> OTHER INFORMATION: PCR primer -continued

```
<400> SEQUENCE: 8
gttcttgctt gaaggtgggt gatt                                            24

<210> SEQ ID NO 9
<211> LENGTH: 25
<212> TYPE: DNA
<213> ORGANISM: Artificial Sequence
<220> FEATURE:
<223> OTHER INFORMATION: PCR primer

<400> SEQUENCE: 9
atactaagca ccagggttga gaatg                                           25

<210> SEQ ID NO 10
<211> LENGTH: 25
<212> TYPE: DNA
<213> ORGANISM: Artificial Sequence
<220> FEATURE:
<223> OTHER INFORMATION: PCR primer

<400> SEQUENCE: 10
aggtagcatt agcagcatcc tggta                                           25

<210> SEQ ID NO 11
<211> LENGTH: 23
<212> TYPE: DNA
<213> ORGANISM: Artificial Sequence
<220> FEATURE:
<223> OTHER INFORMATION: PCR primer

<400> SEQUENCE: 11
ctgacagtct acctggagtt ggg                                             23

<210> SEQ ID NO 12
<211> LENGTH: 39
<212> TYPE: DNA
<213> ORGANISM: Artificial Sequence
<220> FEATURE:
<223> OTHER INFORMATION: PCR primer.

<400> SEQUENCE: 12
cacacaggcc ggccaccatg actccaaagt ttttatggc                            39

<210> SEQ ID NO 13
<211> LENGTH: 42
<212> TYPE: DNA
<213> ORGANISM: Artificial Sequence
<220> FEATURE:
<223> OTHER INFORMATION: PCR primer.

<400> SEQUENCE: 13
cacacaggcg cgcctctatt taagttcttg cttgaaggtg gg                        42

<210> SEQ ID NO 14
<211> LENGTH: 32
<212> TYPE: DNA
<213> ORGANISM: Artificial Sequence
<220> FEATURE:
<223> OTHER INFORMATION: PCR primer.

<400> SEQUENCE: 14
cgtacgggcc ggccaccatg actccaaagt tt                                   32

<210> SEQ ID NO 15
<211> LENGTH: 32
```

<212> TYPE: DNA
<213> ORGANISM: Artificial Sequence
<220> FEATURE:
<223> OTHER INFORMATION: PCR primer.

<400> SEQUENCE: 15
cgcgcgggcg cgccctattt aagttcttgc tt                32

<210> SEQ ID NO 16
<211> LENGTH: 15
<212> TYPE: PRT
<213> ORGANISM: Artificial Sequence
<220> FEATURE:
<223> OTHER INFORMATION: Amino acid motif.
<221> NAME/KEY: VARIANT
<222> LOCATION: (1)...(1)
<223> OTHER INFORMATION: Xaa is Phe, Ser, Pro, or Asn.
<221> NAME/KEY: VARIANT
<222> LOCATION: (2)...(2)
<223> OTHER INFORMATION: Xaa is Pro, Phe, or Gly.
<221> NAME/KEY: VARIANT
<222> LOCATION: (3)...(3)
<223> OTHER INFORMATION: Xaa is Leu or Lys.
<221> NAME/KEY: VARIANT
<222> LOCATION: (4)...(4)
<223> OTHER INFORMATION: Xaa is Arg, Ser, or Ile.
<221> NAME/KEY: VARIANT
<222> LOCATION: (5)...(5)
<223> OTHER INFORMATION: Xaa is Cys or Asn
<221> NAME/KEY: VARIANT
<222> LOCATION: (7)...(7)
<223> OTHER INFORMATION: Xaa is Lys or Thr.
<221> NAME/KEY: VARIANT
<222> LOCATION: (8)...(8)
<223> OTHER INFORMATION: Xaa is Asp or Tyr.
<221> NAME/KEY: VARIANT
<222> LOCATION: (9)...(9)
<223> OTHER INFORMATION: Xaa is Ile or Arg.
<221> NAME/KEY: VARIANT
<222> LOCATION: (10)...(10)
<223> OTHER INFORMATION: Xaa is Thr, Gln, Lys, or Ala.
<221> NAME/KEY: VARIANT
<222> LOCATION: (13)...(13)
<223> OTHER INFORMATION: Xaa is Gly or Lys.
<221> NAME/KEY: VARIANT
<222> LOCATION: (14)...(14)
<223> OTHER INFORMATION: Xaa is Phe or Ile.

<400> SEQUENCE: 16

Xaa Xaa Xaa Xaa Xaa Leu Xaa Xaa Xaa Xaa Asp Phe Xaa Xaa Pro
 1               5                  10                  15

<210> SEQ ID NO 17
<211> LENGTH: 19
<212> TYPE: PRT
<213> ORGANISM: Artificial Sequence
<220> FEATURE:
<223> OTHER INFORMATION: Amino acid motif.
<221> NAME/KEY: VARIANT
<222> LOCATION: (1)...(1)
<223> OTHER INFORMATION: Xaa is Lys, Val, or Arg.
<221> NAME/KEY: VARIANT
<222> LOCATION: (2)...(2)
<223> OTHER INFORMATION: Xaa is Phe or Tyr.
<221> NAME/KEY: VARIANT
<222> LOCATION: (4)...(4)
<223> OTHER INFORMATION: Xaa is Ile, Arg, or Lys.
<221> NAME/KEY: VARIANT
<222> LOCATION: (5)...(5)
<223> OTHER INFORMATION: Xaa is Asn, Glu, Lys, or Leu.
<221> NAME/KEY: VARIANT
<222> LOCATION: (6)...(6)
<223> OTHER INFORMATION: Xaa is Lys or Met.
<221> NAME/KEY: VARIANT
<222> LOCATION: (8)...(8)

```
<223> OTHER INFORMATION: Xaa is Tyr or His.
<221> NAME/KEY: VARIANT
<222> LOCATION: (9)...(9)
<223> OTHER INFORMATION: Xaa is Ser or Asn.
<221> NAME/KEY: VARIANT
<222> LOCATION: (10)...(10)
<223> OTHER INFORMATION: Xaa is Phe, Pro, Leu, or Ser.
<221> NAME/KEY: VARIANT
<222> LOCATION: (11)...(11)
<223> OTHER INFORMATION: Xaa is Cys or Tyr.
<221> NAME/KEY: VARIANT
<222> LOCATION: (14)...(14)
<223> OTHER INFORMATION: Xaa is Lys, Glu, or Met.
<221> NAME/KEY: VARIANT
<222> LOCATION: (15)...(15)
<223> OTHER INFORMATION: Xaa is Ile or Val.
<221> NAME/KEY: VARIANT
<222> LOCATION: (16)...(16)
<223> OTHER INFORMATION: Xaa is Ile or Val.
<221> NAME/KEY: VARIANT
<222> LOCATION: (17)...(17)
<223> OTHER INFORMATION: Xaa is Thr or Arg.
<221> NAME/KEY: VARIANT
<222> LOCATION: (18)...(18)
<223> OTHER INFORMATION: Xaa is Val or Ala.

<400> SEQUENCE: 17

Xaa Xaa Leu Xaa Xaa Xaa Lys Xaa Xaa Xaa Xaa Ala Trp Xaa Xaa Xaa
 1               5                  10                  15

Xaa Xaa Glu

<210> SEQ ID NO 18
<211> LENGTH: 9
<212> TYPE: DNA
<213> ORGANISM: Artificial Sequence
<220> FEATURE:
<223> OTHER INFORMATION: Nucleotide sequence.

<400> SEQUENCE: 18 atgcacggg                                                                9

<210> SEQ ID NO 19
<211> LENGTH: 9
<212> TYPE: DNA
<213> ORGANISM: Artificial Sequence
<220> FEATURE:
<223> OTHER INFORMATION: Nucleotide sequence.

<400> SEQUENCE: 19 cccgtgcat                                                                9

<210> SEQ ID NO 20
<211> LENGTH: 9
<212> TYPE: DNA
<213> ORGANISM: Artificial Sequence
<220> FEATURE:
<223> OTHER INFORMATION: Nucleotide sequence.

<400> SEQUENCE: 20 atggagctt                                                                9

<210> SEQ ID NO 21
<211> LENGTH: 9
<212> TYPE: DNA
<213> ORGANISM: Artificial Sequence
<220> FEATURE:
<223> OTHER INFORMATION: Nucleotide sequence.

<400> SEQUENCE: 21
```

```
agcttgagt                                                                  9

<210> SEQ ID NO 22
<211> LENGTH: 9
<212> TYPE: DNA
<213> ORGANISM: Artificial Sequence
<220> FEATURE:
<223> OTHER INFORMATION: Nucleotide sequence.

<400> SEQUENCE: 22 tcgactacc                                                                  9
```